US010787671B2

(12) United States Patent
Coleman et al.

(10) Patent No.: US 10,787,671 B2
(45) Date of Patent: Sep. 29, 2020

(54) **METHOD FOR PRODUCTION OF RECOMBINANT *ERWINIA ASPARAGINASE***

(71) Applicant: Pfenex Inc., San Diego, CA (US)

(72) Inventors: Russell J. Coleman, San Diego, CA (US); Torben Bruck, Lakeside, CA (US)

(73) Assignee: Pfenex Inc., San Diego, CA (US)

( * ) Notice: Subject to any disclaimer, the term of this patent is extended or adjusted under 35 U.S.C. 154(b) by 60 days.

(21) Appl. No.: 16/163,382

(22) Filed: Oct. 17, 2018

(65) Prior Publication Data

US 2019/0127742 A1 May 2, 2019

Related U.S. Application Data

(60) Provisional application No. 62/578,305, filed on Oct. 27, 2017.

(51) Int. Cl.
*C12N 9/82* (2006.01)
*C12N 15/78* (2006.01)
*C12N 15/67* (2006.01)
*C12R 1/39* (2006.01)

(52) U.S. Cl.
CPC ............... *C12N 15/78* (2013.01); *C12N 9/82* (2013.01); *C12N 15/67* (2013.01); *C12Y 305/01001* (2013.01); *C12R 1/39* (2013.01)

(58) Field of Classification Search
CPC ........................ C12N 15/78; C12Y 305/01001
See application file for complete search history.

(56) References Cited

U.S. PATENT DOCUMENTS

| | | | |
|---|---|---|---|
| 7,807,436 | B2 | 10/2010 | Filpula et al. |
| 2008/0193974 | A1 | 8/2008 | Coleman et al. |
| 2010/0273236 | A1 | 10/2010 | Filpula et al. |
| 2011/0020868 | A1 | 1/2011 | Coleman et al. |
| 2015/0361405 | A1 | 12/2015 | Retallack et al. |
| 2016/0060613 | A1 | 3/2016 | Abribat |
| 2016/0159877 | A1 | 6/2016 | Retallack et al. |
| 2016/0348085 | A1 | 12/2016 | Alves et al. |
| 2017/0044224 | A1 | 2/2017 | Kim et al. |

OTHER PUBLICATIONS

International Application No. PCT/US2018/056374 International Search Report and Written Opinion dated Jan. 11, 2019.
International Application No. PCT/US2018/056375 International Search Report and Written Opinion dated Jan. 17, 2019.
International Application No. PCT/US2018/056376 International Search Report and Written Opinion dated Feb. 19, 2019.
Gervais et al.: RADAR (Research Archive and Digital Asset Repository); Validation of a 30-year-old process for the manufacture of L-asparaginase from Erwinia Chrysanthemi; Bioprocess and Biosystems Engineering; 36(4); pp. 27 (2013).
Glazyrina et al.: High cell density cultivation and recombinant protein production with *Escherichia coli* in a rocking-motion-type bioreactor; Microbial Cell Factories; 9:42 (2010).
Huser et al.: Cloning, sequence analysis, and expression of ansB from Pseudomonas fluorescens, encoding periplasmic glutaminase/asparaginase; FEMS microbiology letters; vol. 178, No. 1, pp. 327-335 (Sep. 1, 1999).
Latifi et al.: The Cytoplasmic and Periplasmic Expression Levels and Folding of Organophosphorus Hydrolase Enzyme in *Escherichia coli*; Jundishapur J Microbiol.; 8(12);1-5 (2015).
Nakamura et al.: On the Productivity and Properties of L-Asparaginase from *Escherichia coli* A-1-3 ; Agr. Biol. Chem., vol. 36, No. 12, p. 2251-2253 (1972).
Roberts et al.: New Procedures for Purification of L-Asparaginase with High Yield from *Escherichia coli*; Journal of Bacteriology; vol. 95, No. 6; pp. 2117-2123 (1968).
PCTUS2018056376 PCT Invitation to Pay Additional Fees dated Dec. 18, 2018.
Genbank Acccession No. CP001836 "Dickeya zeae Ech586 chromosome, complete genome" Aug. 30, 2017: https://www.ncbi.nlm.nih.gov/nuccore/CP001836.
GenBank Accession No. LM996150, May 9, 2015: https://www.ncbi.nlm.nih.gov/nuccore/LM996150.
UniProtKB Accession No. A0A120G5C7_PSEFL, Apr. 13, 2016: https://www.uniprot.org/uniprot/A0A120G5C7.
UniProtKB Accession No. A0A109LCE2 "Asparaginase from Pseudomonas fluorescens" (Apr. 13, 2016) [Retrieved from the internet on Mar. 6, 2019—<https://www.uniprot.org/uniprot/A0A109LCE2].
Wink, et al.: "Comparison between Two Erwinia carotovora L-Asparaginase II Constructions: cloning, Heterologous Expression, Purification, and Kinetic Characterization" JMBT vol. 2 Issue 1 (7 pages).
Bochtler et al.: Crystal structure of heat shock locus V (HslV) from *Escherichia coli*; Proc. Natl. Acad. Sci. USA; vol. 94, pp. 6070-6074 (1997).
Einsfeldt et al.: Recombinant L-Asparaginase from Zymomonas mobilis: A Potential New Antileukemic Agent Produced in *Escherichia coli*; PLOS One; 1-18 (2016).
Elspar (asparaginase): Highlights of Prescribing Information; Reference ID: 3341544; 7 pages (2013).
Erwinaze: Highlights of Prescribing Information; Reference ID: 3909112; 9 pages (2016).
European Medicines Agency: Science Medicines Health; List of nationally authorised medicinal products; 2 pages (2016).
Gilbert et al.: Cloning and Expression of the Erwinia chrysanthemi Asparaginase Gene in *Escherichia coli* and Erwinia carotovora; Journal of General Microbiology, 132, 151-160 (1986).

(Continued)

*Primary Examiner* — Tekchand Saidha
(74) *Attorney, Agent, or Firm* — Wilson Sonsini Goodrich & Rosati

(57) ABSTRACT

Provided herein are methods of production of recombinant *Erwinia* asparaginase. Methods herein produce asparaginase having high expression levels in the periplasm or the cytoplasm of the host cell having activity comparable to commercially available asparaginase preparations.

29 Claims, 7 Drawing Sheets

Specification includes a Sequence Listing.

(56) References Cited

OTHER PUBLICATIONS

Maita et al.: Amino Acid Sequence of L-Asparaginase from *Escherichia coli*; J. Biochem., 76, 1351-1354 (1974).

Nakamura et al.: On the Productivity and Properties of I-Asparaginase from *Escherichia coli* A-I-3; Agricultural and Biological Chemistry; 4 pages (1972).

Oncaspar (pegaspargase): Highlights of Prescribing Information; Reference ID: 3996411; 11 pages (2014).

Oncaspar: Product Information; Annex I-Annex III; Summary of Product Characteristics 1-50 (2019) http://www.ema.europa.eu.

Ramachandran et al.: Functional interactions of HsIV (ClpQ) with the ATPase HsIU (ClpY); Proc. Natl. Acad. Sci.; vol. 99, No. 11, pp. 7396-7401 (2002).

Spectrila: Product Inforamtion; Annex I-Annex III; Summary of Product Characteristics 1-31 (2019) http://www.ema.europa.eu.

Wang et al.: Crystal Structures of the HsIVU Peptidase-ATPase Complex Reveal an ATP-Dependent Proteolysis Mechanism; Structure, vol. 9, 177-184 (2001).

U.S. Appl. No. 16/163,398 Office Action dated Nov. 7, 2019.

743 soluble sonicates, reduced SDS-CGE

```
          SapI
                        A  D  K  L  P  N  I  V  I  L  A  T  G  G  T  I  A  G  S  A  A  T
  1   ATATGCTCTT CAGCCGCAGA CAAACTCCCT AACATCGTAA TCCTCGCAAC TGGTGGTACC ATCGCAGGCA GCGCCGCCAC
      TATACGAGAA GTCGGCGTCT GTTTGAGGGA TTGTAGCATT AGGAGCGTTG ACCACCATGG TAGCGTCCGT CGCGGCGGTG

      T  G  T  Q  T  T  G  Y  K  A  G  A  L  G  V  D  T  L  I  N  A  V  P  E  V  K  K  L
 81   CGGCACGCAG ACCACTGGCT ACAAGGCCGG CGCGCTGGGC GTAGACACGC TGATCAACGC CGTCCCGGAA GTGAAGAAAC
      GCCGTGCGTC TGGTGACCGA TGTTCCGGCC GCGCGACCCG CATCTGTGCG ACTAGTTGCG GCAGGGCCTT CACTTCTTTG

      L  A  N  V  K  G  E  Q  F  S  N  M  A  S  E  N  M  T  G  D  V  V  L  K  L  S  Q
161   TGGCCAACGT CAAGGGTGAG CAATTCTCCA ACATGGCCAG CGAGAACATG ACTGGCGATG TGGTACTGAA GCTCTCGCAG
      ACCGGTTGCA GTTCCCACTC GTTAAGAGGT TGTACCGGTC GCTCTTGTAC TGACCGCTAC ACCATGACTT CGAGAGCGTC

      R  V  N  E  L  L  A  R  D  D  V  D  G  V  V  I  T  H  G  T  D  T  V  E  E  S  A
241   CGCGTGAACG AACTGCTCGC CCGCGACGAC GTGGACGGCG TGGTGATCAC CCACGGCACT GATACCGTCG AAGAGTCGGC
      GCGCACTTGC TTGACGAGCG GGCGCTGCTG CACCTGCCGC ACCACTAGTG GGTGCCGTGA CTATGGCAGC TTCTCAGCCG

      A  Y  F  L  H  L  T  V  K  S  D  K  P  V  V  F  V  A  A  M  R  P  A  T  A  I  S  A
321   GTACTTTCTC CACCTGACCG TGAAGTCCGA TAAGCCCGTG GTGTTTGTCG CCGCGATGCG CCCGGCGACC GCCATCAGCG
      CATGAAAGAG GTGGACTGGC ACTTCAGGCT ATTCGGGCAC CACAAACAGC GGCGCTACGC GGGCCGCTGG CGGTAGTCGC

      A  D  G  P  M  N  L  L  E  A  V  R  V  A  G  D  K  Q  S  R  G  R  G  V  M  V  V
401   CCGACGGGCC GATGAATCTG TTGGAAGCCG TGCGCGTGGC GGGTGACAAG CAAAGCCGCG GTCGGGGCGT AATGGTCGTC
      GGCTGCCCGG CTACTTAGAC AACCTTCGGC ACGCGCACCG CCCACTGTTC GTTTCGGCGC CAGCCCCGCA TTACCAGCAG

      L  N  D  R  I  G  S  A  R  Y  I  T  K  T  N  A  S  T  L  D  T  F  K  A  N  E  E
481   CTGAACGATC GGATCGGTAG CGCGCGGTAC ATCACCAAGA CGAACGCCTC CACGCTGGAC ACCTTCAAGG CGAACGAAGA
      GACTTGCTAG CCTAGCCATC GCGCGCCATG TAGTGGTTCT GCTTGCGGAG GTGCGACCTG TGGAAGTTCC GCTTGCTTCT

      E  G  Y  L  G  V  I  I  G  N  R  I  Y  Y  Q  N  R  I  D  K  L  H  T  T  R  S  V  F
561   GGGGTACCTG GGGGTGATCA TTGGCAATCG TATCTATTAC CAGAACCGCA TCGACAAGCT GCACACCACC CGCTCGGTGT
      CCCCATGGAC CCCCACTAGT AACCGTTAGC ATAGATAATG GTCTTGGCGT AGCTGTTCGA CGTGTGGTGG GCGAGCCACA

      F  D  V  R  G  L  T  S  L  P  K  V  D  I  L  Y  G  Y  Q  D  D  P  E  Y  L  Y  D
641   TCGACGTGCG CGGTCTGACT AGCCTGCCCA AGGTCGACAT CCTGTACGGC TACCAAGACG ACCCGGAGTA CCTCTACGAC
      AGCTGCACGC GCCAGACTGA TCGGACGGGT TCCAGCTGTA GGACATGCCG ATGGTTCTGC TGGGCCTCAT GGAGATGCTG

      A  A  I  Q  H  G  V  K  G  I  V  Y  A  G  M  G  A  G  S  V  S  V  R  G  I  A  G
721   GCGGCGATCC AGCATGGCGT GAAGGGCATC GTCTACGCCG GTATGGGTGC CGGCTCGGTG TCGGTCCGCG GCATCGCGGG
      CGCCGCTAGG TCGTACCGCA CTTCCCGTAG CAGATGCGGC CATACCCACG GCCGAGCCAC AGCCAGGCGC CGTAGCGCCC

      G  M  R  K  A  M  E  K  G  V  V  V  I  R  S  T  R  T  G  N  G  I  V  P  P  D  E  E
801   TATGCGCAAG GCCATGGAGA AAGGCGTGGT CGTGATTCGC TCGACCCGGA CTGGCAATGG CATCGTACCG CCCGATGAAG
      ATACGCGTTC CGGTACCTCT TTCCGCACCA GCACTAAGCG AGCTGGGCCT GACCGTTACC GTAGCATGGC GGGCTACTTC

      E  L  P  G  L  V  S  D  S  L  N  P  A  H  A  R  I  L  L  M  L  A  L  T  R  T  S
881   AACTCCCGGG GCTCGTGAGC GATAGCCTCA ACCCCGCGCA CGCCCGGATC CTGCTGATGC TGGCGCTCAC GCGGACCAGC
      TTGAGGGCCC CGAGCACTCG CTATCGGAGT TGGGGCGCGT GCGGGCCTAG GACGACTACG ACCGCGAGTG CGCCTGGTCG

      D  P  K  V  I  Q  E  Y  F  H  T  Y
961   GACCCCAAGG TCATTCAAGA GTACTTCCAC ACCTACTGAT AATAGTTCAG AAGAGCATAT
      CTGGGGTTCC AGTAAGTTCT CATGAAGGTG TGGATGACTA TTATCAAGTC TTCTCGTATA
                                                          SapI
```

FIG. 2

SEQUENCE LISTING

```
<160> NUMBER OF SEQ ID NOS: 63

<210> SEQ ID NO 1
<211> LENGTH: 327
<212> TYPE: PRT
<213> ORGANISM: Erwinia chrysanthemi

<400> SEQUENCE: 1

Ala Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Glu Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
    130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
        195                 200                 205

Phe Asp Val Arg Gly Leu Thr Ser Leu Pro Lys Val Asp Ile Leu Tyr
    210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Ser Val Ser
                245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
        275                 280                 285

Glu Leu Pro Gly Leu Val Ser Asp Ser Leu Asn Pro Ala His Ala Arg
    290                 295                 300

Ile Leu Leu Met Leu Ala Leu Thr Arg Thr Ser Asp Pro Lys Val Ile
305                 310                 315                 320

Gln Glu Tyr Phe His Thr Tyr
```

325

<210> SEQ ID NO 2
<211> LENGTH: 981
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2

```
gcagacaaac tccctaacat cgtaatcctc gcaactggtg gtaccatcgc aggcagcgcc     60

gccaccggca cgcagaccac tggctacaag gccggcgcgc tgggcgtaga cacgctgatc    120

aacgccgtcc cggaagtgaa gaaactggcc aacgtcaagg gtgagcaatt ctccaacatg    180

gccagcgaga acatgactgg cgatgtggta ctgaagctct cgcagcgcgt gaacgaactg    240

ctcgcccgcg acgacgtgga cggcgtggtg atcacccacg gcactgatac cgtcgaagag    300

tcggcgtact ttctccacct gaccgtgaag tccgataagc ccgtggtgtt tgtcgccgcg    360

atgcgcccgg cgaccgccat cagcgccgac gggccgatga atctgttgga agccgtgcgc    420

gtggcgggtg acaagcaaag ccgcggtcgg ggcgtaatgg tcgtcctgaa cgatcggatc    480

ggtagcgcgc ggtacatcac caagacgaac gcctccacgc tggacacctt caaggcgaac    540

gaagaggggt acctgggggt gatcattggc aatcgtatct attaccagaa ccgcatcgac    600

aagctgcaca ccacccgctc ggtgttcgac gtgcgcggtc tgactagcct gcccaaggtc    660

gacatcctgt acggctacca agacgacccg gagtacctct acgacgcggc gatccagcat    720

ggcgtgaagg gcatcgtcta cgccggtatg ggtgccggct cggtgtcggt ccgcggcatc    780

gcgggtatgc gcaaggccat ggagaaaggc gtggtcgtga ttcgctcgac ccggactggc    840

aatggcatcg taccgcccga tgaagaactc ccggggctcg tgagcgatag cctcaacccc    900

gcgcacgccc ggatcctgct gatgctggcg ctcacgcgga ccagcgaccc caaggtcatt    960

caagagtact tccacaccta c                                              981
```

<210> SEQ ID NO 3
<211> LENGTH: 22
<212> TYPE: PRT
<213> ORGANISM: Pseudomonas fluorescens

<400> SEQUENCE: 3

```
Met Arg Asn Leu Ile Leu Ser Ala Ala Leu Val Thr Ala Ser Leu Phe
1               5                   10                  15

Gly Met Thr Ala Gln Ala
            20
```

<210> SEQ ID NO 4
<211> LENGTH: 66
<212> TYPE: DNA
<213> ORGANISM: Pseudomonas fluorescens

<400> SEQUENCE: 4

```
atgcgtaatc tgatcctcag cgccgctctc gtcactgcca gcctcttcgg catgaccgca     60

caagct                                                                66
```

<210> SEQ ID NO 5
<211> LENGTH: 20
<212> TYPE: PRT
<213> ORGANISM: Pseudomonas fluorescens

<400> SEQUENCE: 5

```
Met Phe Ala Lys Leu Val Ala Val Ser Leu Leu Thr Leu Ala Ser Gly
1               5                   10                  15

Gln Leu Leu Ala
            20
```

<210> SEQ ID NO 6
<211> LENGTH: 60
<212> TYPE: DNA
<213> ORGANISM: Pseudomonas fluorescens

<400> SEQUENCE: 6

```
atgtttgcca aactcgttgc tgtttccctg ctgactctgg cgagcggcca gttgcttgct     60
```

<210> SEQ ID NO 7
<211> LENGTH: 23
<212> TYPE: PRT
<213> ORGANISM: Pseudomonas fluorescens

<400> SEQUENCE: 7

```
Met Gln Asn Tyr Lys Lys Phe Leu Leu Ala Ala Ala Val Ser Met Ala
1               5                   10                  15

Phe Ser Ala Thr Ala Met Ala
            20
```

<210> SEQ ID NO 8
<211> LENGTH: 69
<212> TYPE: DNA
<213> ORGANISM: Pseudomonas fluorescens

<400> SEQUENCE: 8

```
atgcagaact ataaaaaatt ccttctggcc gcggccgtct cgatggcgtt cagcgccacg     60

gccatggca                                                             69
```

<210> SEQ ID NO 9
<211> LENGTH: 31
<212> TYPE: PRT
<213> ORGANISM: Pseudomonas fluorescens

<400> SEQUENCE: 9

```
Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30
```

<210> SEQ ID NO 10
<211> LENGTH: 93
<212> TYPE: DNA
<213> ORGANISM: Pseudomonas fluorescens

<400> SEQUENCE: 10

```
atgatccgtg acaaccgact caagacatcc cttctgcgcg gcctgaccct caccctactc     60

agcctgaccc tgctctcgcc cgcggcccat gcc                                  93
```

<210> SEQ ID NO 11
<211> LENGTH: 21
<212> TYPE: PRT
<213> ORGANISM: Pseudomonas fluorescens

<400> SEQUENCE: 11

```
Met Arg Asn Leu Leu Arg Gly Met Leu Val Val Ile Cys Cys Met Ala
```

```
1               5                   10                  15

Gly Ile Ala Ala Ala
            20


<210> SEQ ID NO 12
<211> LENGTH: 63
<212> TYPE: DNA
<213> ORGANISM: Pseudomonas fluorescens

<400> SEQUENCE: 12

atgagaaacc ttcttcgagg aatgcttgtc gttatttgct gtatggcagg gatagcggcg     60

gcc                                                                   63


<210> SEQ ID NO 13
<211> LENGTH: 21
<212> TYPE: PRT
<213> ORGANISM: Pseudomonas fluorescens

<400> SEQUENCE: 13

Met Asn Arg Ser Ser Ala Leu Leu Leu Ala Phe Val Phe Leu Ser Gly
1               5                   10                  15

Cys Gln Ala Met Ala
            20


<210> SEQ ID NO 14
<211> LENGTH: 63
<212> TYPE: DNA
<213> ORGANISM: Pseudomonas fluorescens

<400> SEQUENCE: 14

atgaatagat cttccgcgtt gctcctcgct tttgtcttcc tcagcggctg ccaggccatg     60

gcc                                                                   63


<210> SEQ ID NO 15
<211> LENGTH: 33
<212> TYPE: PRT
<213> ORGANISM: Pseudomonas fluorescens

<400> SEQUENCE: 15

Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala


<210> SEQ ID NO 16
<211> LENGTH: 99
<212> TYPE: DNA
<213> ORGANISM: Pseudomonas fluorescens

<400> SEQUENCE: 16

atgcaaaacc gcactgtgga aatcggtgtc ggccttttct tgctggctgg catcctggct     60

ttactgttgt tggccctgcg agtcagcggc ctttcggcc                            99


<210> SEQ ID NO 17
<211> LENGTH: 21
<212> TYPE: PRT
<213> ORGANISM: Pseudomonas fluorescens

<400> SEQUENCE: 17
```

```
Met Lys Phe Lys Gln Leu Met Ala Met Ala Leu Leu Leu Ala Leu Ser
1               5                   10                  15

Ala Val Ala Gln Ala
            20


<210> SEQ ID NO 18
<211> LENGTH: 63
<212> TYPE: DNA
<213> ORGANISM: Pseudomonas fluorescens

<400> SEQUENCE: 18

atgaagttca aacagctgat ggcgatggcg cttttgttgg ccttgagcgc tgtggcccag      60

gcc                                                                    63


<210> SEQ ID NO 19
<211> LENGTH: 23
<212> TYPE: PRT
<213> ORGANISM: Pseudomonas fluorescens

<400> SEQUENCE: 19

Met Pro Pro Arg Ser Ile Ala Ala Cys Leu Gly Leu Leu Gly Leu Leu
1               5                   10                  15

Met Ala Thr Gln Ala Ala Ala
            20


<210> SEQ ID NO 20
<211> LENGTH: 69
<212> TYPE: DNA
<213> ORGANISM: Pseudomonas fluorescens

<400> SEQUENCE: 20

atgccgcctc gttctatcgc cgcatgtctg gggctgctgg gcttgctcat ggctacccag      60

gccgccgcc                                                              69


<210> SEQ ID NO 21
<211> LENGTH: 24
<212> TYPE: PRT
<213> ORGANISM: Pseudomonas fluorescens

<400> SEQUENCE: 21

Met Leu Phe Arg Thr Leu Leu Ala Ser Leu Thr Phe Ala Val Ile Ala
1               5                   10                  15

Gly Leu Pro Ser Thr Ala His Ala
            20


<210> SEQ ID NO 22
<211> LENGTH: 72
<212> TYPE: DNA
<213> ORGANISM: Pseudomonas fluorescens

<400> SEQUENCE: 22

atgctttttc gcacattact ggcgagcctt acctttgctg tcatcgccgg cttaccgtcc      60

acggcccacg cg                                                          72


<210> SEQ ID NO 23
<211> LENGTH: 24
<212> TYPE: PRT
<213> ORGANISM: Pseudomonas fluorescens

<400> SEQUENCE: 23

Met Lys Leu Lys Arg Leu Met Ala Ala Met Thr Phe Val Ala Ala Gly
```

```
1               5                   10                  15

Val Ala Thr Ala Asn Ala Val Ala
            20


<210> SEQ ID NO 24
<211> LENGTH: 72
<212> TYPE: DNA
<213> ORGANISM: Pseudomonas fluorescens

<400> SEQUENCE: 24

atgaaactga aacgtttgat ggcggcaatg acttttgtcg ctgctggcgt tgcgaccgcc     60

aacgcggtgg cc                                                         72


<210> SEQ ID NO 25
<211> LENGTH: 24
<212> TYPE: PRT
<213> ORGANISM: Pseudomonas fluorescens

<400> SEQUENCE: 25

Met Lys Leu Lys Arg Leu Met Ala Ala Met Thr Phe Val Ala Ala Gly
1               5                   10                  15

Val Ala Thr Val Asn Ala Val Ala
            20


<210> SEQ ID NO 26
<211> LENGTH: 72
<212> TYPE: DNA
<213> ORGANISM: Pseudomonas fluorescens

<400> SEQUENCE: 26

atgaaactga aacgtttgat ggcggcaatg acttttgtcg ctgctggcgt tgcgaccgtc     60

aacgcggtgg cc                                                         72


<210> SEQ ID NO 27
<211> LENGTH: 21
<212> TYPE: PRT
<213> ORGANISM: Pseudomonas fluorescens

<400> SEQUENCE: 27

Met Arg Leu Thr Gln Ile Ile Ala Ala Ala Ala Ile Ala Leu Val Ser
1               5                   10                  15

Thr Phe Ala Leu Ala
            20


<210> SEQ ID NO 28
<211> LENGTH: 63
<212> TYPE: DNA
<213> ORGANISM: Pseudomonas fluorescens

<400> SEQUENCE: 28

atgcgcttga cccagattat tgccgccgca gccattgcgt tggtttccac ctttgcgctc     60

gcc                                                                   63


<210> SEQ ID NO 29
<211> LENGTH: 21
<212> TYPE: PRT
<213> ORGANISM: Pseudomonas fluorescens

<400> SEQUENCE: 29

Met Lys Lys Ser Thr Leu Ala Val Ala Val Thr Leu Gly Ala Ile Ala
1               5                   10                  15
```

```
Gln Gln Ala Gly Ala
            20


<210> SEQ ID NO 30
<211> LENGTH: 63
<212> TYPE: DNA
<213> ORGANISM: Pseudomonas fluorescens

<400> SEQUENCE: 30

atgaagaagt ccaccttggc tgtggctgta acgttgggcg caatcgccca gcaagcaggc     60

gct                                                                   63


<210> SEQ ID NO 31
<211> LENGTH: 29
<212> TYPE: PRT
<213> ORGANISM: Pseudomonas fluorescens

<400> SEQUENCE: 31

Met Gln Ser Leu Pro Phe Ser Ala Leu Arg Leu Leu Gly Val Leu Ala
1               5                   10                  15

Val Met Val Cys Val Leu Leu Thr Thr Pro Ala Arg Ala
            20                  25


<210> SEQ ID NO 32
<211> LENGTH: 87
<212> TYPE: DNA
<213> ORGANISM: Pseudomonas fluorescens

<400> SEQUENCE: 32

atgcaaagcc tgccgttctc tgcgttacgc ctgctcggtg tgctggcagt catggtctgc     60

gtgctgttga cgacgccagc ccgtgcc                                         87


<210> SEQ ID NO 33
<211> LENGTH: 18
<212> TYPE: PRT
<213> ORGANISM: Pseudomonas fluorescens

<400> SEQUENCE: 33

Met Arg Gln Leu Phe Phe Cys Leu Met Leu Met Val Ser Leu Thr Ala
1               5                   10                  15

His Ala


<210> SEQ ID NO 34
<211> LENGTH: 54
<212> TYPE: DNA
<213> ORGANISM: Pseudomonas fluorescens

<400> SEQUENCE: 34

atgcgacaac tatttttctg tttgatgctg atggtgtcgc tcacggcgca cgcc           54


<210> SEQ ID NO 35
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Lys Phe Lys Gln Leu Met Ala Met Ala Leu Leu Leu Ala Leu Ser
1               5                   10                  15
```

```
Ala Val Ala Gln Ala Ala Asp Lys Leu Pro Asn Ile Val Ile Leu Ala
            20                  25                  30

Thr Gly Gly Thr Ile Ala Gly Ser Ala Ala Thr Gly Thr Gln Thr Thr
        35                  40                  45

Gly Tyr Lys Ala Gly Ala Leu Gly Val Asp Thr Leu Ile Asn Ala Val
    50                  55                  60

Pro Glu Val Lys Lys Leu Ala Asn Val Lys Gly Glu Gln Phe Ser Asn
65                  70                  75                  80

Met Ala Ser Glu Asn Met Thr Gly Asp Val Val Leu Lys Leu Ser Gln
                85                  90                  95

Arg Val Asn Glu Leu Leu Ala Arg Asp Asp Val Asp Gly Val Val Ile
            100                 105                 110

Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
                165                 170                 175

Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Val Ile Arg Ser Thr Arg Thr Gly Asn Gly Ile
    290                 295                 300

Val Pro Pro Asp Glu Glu Leu Pro Gly Leu Val Ser Asp Ser Leu Asn
305                 310                 315                 320

Pro Ala His Ala Arg Ile Leu Leu Met Leu Ala Leu Thr Arg Thr Ser
                325                 330                 335

Asp Pro Lys Val Ile Gln Glu Tyr Phe His Thr Tyr
            340                 345
```

<210> SEQ ID NO 36
<211> LENGTH: 345
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Met Arg Gln Leu Phe Phe Cys Leu Met Leu Met Val Ser Leu Thr Ala
1               5                   10                  15

His Ala Ala Asp Lys Leu Pro Asn Ile Val Ile Leu Ala Thr Gly Gly
            20                  25                  30
```

```
Thr Ile Ala Gly Ser Ala Ala Thr Gly Thr Gln Thr Thr Gly Tyr Lys
        35                  40                  45

Ala Gly Ala Leu Gly Val Asp Thr Leu Ile Asn Ala Val Pro Glu Val
    50                  55                  60

Lys Lys Leu Ala Asn Val Lys Gly Glu Gln Phe Ser Asn Met Ala Ser
65                  70                  75                  80

Glu Asn Met Thr Gly Asp Val Val Leu Lys Leu Ser Gln Arg Val Asn
                85                  90                  95

Glu Leu Leu Ala Arg Asp Asp Val Asp Gly Val Val Ile Thr His Gly
            100                 105                 110

Thr Asp Thr Val Glu Glu Ser Ala Tyr Phe Leu His Leu Thr Val Lys
        115                 120                 125

Ser Asp Lys Pro Val Val Phe Val Ala Ala Met Arg Pro Ala Thr Ala
    130                 135                 140

Ile Ser Ala Asp Gly Pro Met Asn Leu Leu Glu Ala Val Arg Val Ala
145                 150                 155                 160

Gly Asp Lys Gln Ser Arg Gly Arg Gly Val Met Val Val Leu Asn Asp
                165                 170                 175

Arg Ile Gly Ser Ala Arg Tyr Ile Thr Lys Thr Asn Ala Ser Thr Leu
            180                 185                 190

Asp Thr Phe Lys Ala Asn Glu Glu Gly Tyr Leu Gly Val Ile Ile Gly
        195                 200                 205

Asn Arg Ile Tyr Tyr Gln Asn Arg Ile Asp Lys Leu His Thr Thr Arg
    210                 215                 220

Ser Val Phe Asp Val Arg Gly Leu Thr Ser Leu Pro Lys Val Asp Ile
225                 230                 235                 240

Leu Tyr Gly Tyr Gln Asp Asp Pro Glu Tyr Leu Tyr Asp Ala Ala Ile
                245                 250                 255

Gln His Gly Val Lys Gly Ile Val Tyr Ala Gly Met Gly Ala Gly Ser
            260                 265                 270

Val Ser Val Arg Gly Ile Ala Gly Met Arg Lys Ala Met Glu Lys Gly
        275                 280                 285

Val Val Val Ile Arg Ser Thr Arg Thr Gly Asn Gly Ile Val Pro Pro
    290                 295                 300

Asp Glu Glu Leu Pro Gly Leu Val Ser Asp Ser Leu Asn Pro Ala His
305                 310                 315                 320

Ala Arg Ile Leu Leu Met Leu Ala Leu Thr Arg Thr Ser Asp Pro Lys
                325                 330                 335

Val Ile Gln Glu Tyr Phe His Thr Tyr
            340                 345


<210> SEQ ID NO 37
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Arg Leu Thr Gln Ile Ile Ala Ala Ala Ala Ile Ala Leu Val Ser
1               5                   10                  15

Thr Phe Ala Leu Ala Ala Asp Lys Leu Pro Asn Ile Val Ile Leu Ala
            20                  25                  30

Thr Gly Gly Thr Ile Ala Gly Ser Ala Ala Thr Gly Thr Gln Thr Thr
```

```
        35                  40                  45

Gly Tyr Lys Ala Gly Ala Leu Gly Val Asp Thr Leu Ile Asn Ala Val
    50                  55                  60

Pro Glu Val Lys Lys Leu Ala Asn Val Lys Gly Glu Gln Phe Ser Asn
65                  70                  75                  80

Met Ala Ser Glu Asn Met Thr Gly Asp Val Val Leu Lys Leu Ser Gln
                85                  90                  95

Arg Val Asn Glu Leu Leu Ala Arg Asp Asp Val Asp Gly Val Val Ile
            100                 105                 110

Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
                165                 170                 175

Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Val Ile Arg Ser Thr Arg Thr Gly Asn Gly Ile
    290                 295                 300

Val Pro Pro Asp Glu Glu Leu Pro Gly Leu Val Ser Asp Ser Leu Asn
305                 310                 315                 320

Pro Ala His Ala Arg Ile Leu Leu Met Leu Ala Leu Thr Arg Thr Ser
                325                 330                 335

Asp Pro Lys Val Ile Gln Glu Tyr Phe His Thr Tyr
            340                 345


<210> SEQ ID NO 38
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala Ala
            20                  25                  30

Asp Lys Leu Pro Asn Ile Val Ile Leu Ala Thr Gly Gly Thr Ile Ala
        35                  40                  45
```

```
Gly Ser Ala Ala Thr Gly Thr Gln Thr Thr Gly Tyr Lys Ala Gly Ala
    50                  55                  60

Leu Gly Val Asp Thr Leu Ile Asn Ala Val Pro Glu Val Lys Lys Leu
65                  70                  75                  80

Ala Asn Val Lys Gly Glu Gln Phe Ser Asn Met Ala Ser Glu Asn Met
                85                  90                  95

Thr Gly Asp Val Val Leu Lys Leu Ser Gln Arg Val Asn Glu Leu Leu
            100                 105                 110

Ala Arg Asp Asp Val Asp Gly Val Val Ile Thr His Gly Thr Asp Thr
        115                 120                 125

Val Glu Glu Ser Ala Tyr Phe Leu His Leu Thr Val Lys Ser Asp Lys
    130                 135                 140

Pro Val Val Phe Val Ala Ala Met Arg Pro Ala Thr Ala Ile Ser Ala
145                 150                 155                 160

Asp Gly Pro Met Asn Leu Leu Glu Ala Val Arg Val Ala Gly Asp Lys
                165                 170                 175

Gln Ser Arg Gly Arg Gly Val Met Val Val Leu Asn Asp Arg Ile Gly
            180                 185                 190

Ser Ala Arg Tyr Ile Thr Lys Thr Asn Ala Ser Thr Leu Asp Thr Phe
        195                 200                 205

Lys Ala Asn Glu Glu Gly Tyr Leu Gly Val Ile Ile Gly Asn Arg Ile
    210                 215                 220

Tyr Tyr Gln Asn Arg Ile Asp Lys Leu His Thr Thr Arg Ser Val Phe
225                 230                 235                 240

Asp Val Arg Gly Leu Thr Ser Leu Pro Lys Val Asp Ile Leu Tyr Gly
                245                 250                 255

Tyr Gln Asp Asp Pro Glu Tyr Leu Tyr Asp Ala Ala Ile Gln His Gly
            260                 265                 270

Val Lys Gly Ile Val Tyr Ala Gly Met Gly Ala Gly Ser Val Ser Val
        275                 280                 285

Arg Gly Ile Ala Gly Met Arg Lys Ala Met Glu Lys Gly Val Val Val
    290                 295                 300

Ile Arg Ser Thr Arg Thr Gly Asn Gly Ile Val Pro Pro Asp Glu Glu
305                 310                 315                 320

Leu Pro Gly Leu Val Ser Asp Ser Leu Asn Pro Ala His Ala Arg Ile
                325                 330                 335

Leu Leu Met Leu Ala Leu Thr Arg Thr Ser Asp Pro Lys Val Ile Gln
            340                 345                 350

Glu Tyr Phe His Thr Tyr
        355


<210> SEQ ID NO 39
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gln Ser Leu Pro Phe Ser Ala Leu Arg Leu Leu Gly Val Leu Ala
1               5                   10                  15

Val Met Val Cys Val Leu Leu Thr Thr Pro Ala Arg Ala Ala Asp Lys
            20                  25                  30

Leu Pro Asn Ile Val Ile Leu Ala Thr Gly Gly Thr Ile Ala Gly Ser
        35                  40                  45
```

```
Ala Ala Thr Gly Thr Gln Thr Thr Gly Tyr Lys Ala Gly Ala Leu Gly
    50                  55                  60

Val Asp Thr Leu Ile Asn Ala Val Pro Glu Val Lys Lys Leu Ala Asn
65                  70                  75                  80

Val Lys Gly Glu Gln Phe Ser Asn Met Ala Ser Glu Asn Met Thr Gly
                85                  90                  95

Asp Val Val Leu Lys Leu Ser Gln Arg Val Asn Glu Leu Leu Ala Arg
            100                 105                 110

Asp Asp Val Asp Gly Val Val Ile Thr His Gly Thr Asp Thr Val Glu
        115                 120                 125

Glu Ser Ala Tyr Phe Leu His Leu Thr Val Lys Ser Asp Lys Pro Val
    130                 135                 140

Val Phe Val Ala Ala Met Arg Pro Ala Thr Ala Ile Ser Ala Asp Gly
145                 150                 155                 160

Pro Met Asn Leu Leu Glu Ala Val Arg Val Ala Gly Asp Lys Gln Ser
                165                 170                 175

Arg Gly Arg Gly Val Met Val Val Leu Asn Asp Arg Ile Gly Ser Ala
            180                 185                 190

Arg Tyr Ile Thr Lys Thr Asn Ala Ser Thr Leu Asp Thr Phe Lys Ala
        195                 200                 205

Asn Glu Glu Gly Tyr Leu Gly Val Ile Ile Gly Asn Arg Ile Tyr Tyr
    210                 215                 220

Gln Asn Arg Ile Asp Lys Leu His Thr Thr Arg Ser Val Phe Asp Val
225                 230                 235                 240

Arg Gly Leu Thr Ser Leu Pro Lys Val Asp Ile Leu Tyr Gly Tyr Gln
                245                 250                 255

Asp Asp Pro Glu Tyr Leu Tyr Asp Ala Ala Ile Gln His Gly Val Lys
            260                 265                 270

Gly Ile Val Tyr Ala Gly Met Gly Ala Gly Ser Val Ser Val Arg Gly
        275                 280                 285

Ile Ala Gly Met Arg Lys Ala Met Glu Lys Gly Val Val Val Ile Arg
    290                 295                 300

Ser Thr Arg Thr Gly Asn Gly Ile Val Pro Pro Asp Glu Glu Leu Pro
305                 310                 315                 320

Gly Leu Val Ser Asp Ser Leu Asn Pro Ala His Ala Arg Ile Leu Leu
                325                 330                 335

Met Leu Ala Leu Thr Arg Thr Ser Asp Pro Lys Val Ile Gln Glu Tyr
            340                 345                 350

Phe His Thr Tyr
        355


<210> SEQ ID NO 40
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asn Arg Ser Ser Ala Leu Leu Leu Ala Phe Val Phe Leu Ser Gly
1               5                   10                  15

Cys Gln Ala Met Ala Ala Asp Lys Leu Pro Asn Ile Val Ile Leu Ala
            20                  25                  30

Thr Gly Gly Thr Ile Ala Gly Ser Ala Ala Thr Gly Thr Gln Thr Thr
```

```
        35                  40                  45

Gly Tyr Lys Ala Gly Ala Leu Gly Val Asp Thr Leu Ile Asn Ala Val
    50                  55                  60

Pro Glu Val Lys Lys Leu Ala Asn Val Lys Gly Glu Gln Phe Ser Asn
65                  70                  75                  80

Met Ala Ser Glu Asn Met Thr Gly Asp Val Val Leu Lys Leu Ser Gln
                85                  90                  95

Arg Val Asn Glu Leu Leu Ala Arg Asp Asp Val Asp Gly Val Val Ile
            100                 105                 110

Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
                165                 170                 175

Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Val Ile Arg Ser Thr Arg Thr Gly Asn Gly Ile
    290                 295                 300

Val Pro Pro Asp Glu Glu Leu Pro Gly Leu Val Ser Asp Ser Leu Asn
305                 310                 315                 320

Pro Ala His Ala Arg Ile Leu Leu Met Leu Ala Leu Thr Arg Thr Ser
                325                 330                 335

Asp Pro Lys Val Ile Gln Glu Tyr Phe His Thr Tyr
            340                 345


<210> SEQ ID NO 41
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala Ala Asp Lys Leu Pro Asn Ile Val Ile Leu Ala Thr Gly Gly Thr
        35                  40                  45
```

```
Ile Ala Gly Ser Ala Ala Thr Gly Thr Gln Thr Thr Gly Tyr Lys Ala
    50                  55                  60

Gly Ala Leu Gly Val Asp Thr Leu Ile Asn Ala Val Pro Glu Val Lys
65                  70                  75                  80

Lys Leu Ala Asn Val Lys Gly Glu Gln Phe Ser Asn Met Ala Ser Glu
                85                  90                  95

Asn Met Thr Gly Asp Val Val Leu Lys Leu Ser Gln Arg Val Asn Glu
            100                 105                 110

Leu Leu Ala Arg Asp Asp Val Asp Gly Val Val Ile Thr His Gly Thr
        115                 120                 125

Asp Thr Val Glu Glu Ser Ala Tyr Phe Leu His Leu Thr Val Lys Ser
    130                 135                 140

Asp Lys Pro Val Val Phe Val Ala Ala Met Arg Pro Ala Thr Ala Ile
145                 150                 155                 160

Ser Ala Asp Gly Pro Met Asn Leu Leu Glu Ala Val Arg Val Ala Gly
                165                 170                 175

Asp Lys Gln Ser Arg Gly Arg Gly Val Met Val Val Leu Asn Asp Arg
            180                 185                 190

Ile Gly Ser Ala Arg Tyr Ile Thr Lys Thr Asn Ala Ser Thr Leu Asp
        195                 200                 205

Thr Phe Lys Ala Asn Glu Glu Gly Tyr Leu Gly Val Ile Ile Gly Asn
    210                 215                 220

Arg Ile Tyr Tyr Gln Asn Arg Ile Asp Lys Leu His Thr Thr Arg Ser
225                 230                 235                 240

Val Phe Asp Val Arg Gly Leu Thr Ser Leu Pro Lys Val Asp Ile Leu
                245                 250                 255

Tyr Gly Tyr Gln Asp Asp Pro Glu Tyr Leu Tyr Asp Ala Ala Ile Gln
            260                 265                 270

His Gly Val Lys Gly Ile Val Tyr Ala Gly Met Gly Ala Gly Ser Val
        275                 280                 285

Ser Val Arg Gly Ile Ala Gly Met Arg Lys Ala Met Glu Lys Gly Val
    290                 295                 300

Val Val Ile Arg Ser Thr Arg Thr Gly Asn Gly Ile Val Pro Pro Asp
305                 310                 315                 320

Glu Glu Leu Pro Gly Leu Val Ser Asp Ser Leu Asn Pro Ala His Ala
                325                 330                 335

Arg Ile Leu Leu Met Leu Ala Leu Thr Arg Thr Ser Asp Pro Lys Val
            340                 345                 350

Ile Gln Glu Tyr Phe His Thr Tyr
        355                 360


<210> SEQ ID NO 42
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Leu Phe Arg Thr Leu Leu Ala Ser Leu Thr Phe Ala Val Ile Ala
1               5                   10                  15

Gly Leu Pro Ser Thr Ala His Ala Ala Asp Lys Leu Pro Asn Ile Val
            20                  25                  30

Ile Leu Ala Thr Gly Gly Thr Ile Ala Gly Ser Ala Ala Thr Gly Thr
        35                  40                  45
```

```
Gln Thr Thr Gly Tyr Lys Ala Gly Ala Leu Gly Val Asp Thr Leu Ile
    50                  55                  60

Asn Ala Val Pro Glu Val Lys Lys Leu Ala Asn Val Lys Gly Glu Gln
65                  70                  75                  80

Phe Ser Asn Met Ala Ser Glu Asn Met Thr Gly Asp Val Val Leu Lys
                85                  90                  95

Leu Ser Gln Arg Val Asn Glu Leu Leu Ala Arg Asp Asp Val Asp Gly
            100                 105                 110

Val Val Ile Thr His Gly Thr Asp Thr Val Glu Glu Ser Ala Tyr Phe
        115                 120                 125

Leu His Leu Thr Val Lys Ser Asp Lys Pro Val Val Phe Val Ala Ala
    130                 135                 140

Met Arg Pro Ala Thr Ala Ile Ser Ala Asp Gly Pro Met Asn Leu Leu
145                 150                 155                 160

Glu Ala Val Arg Val Ala Gly Asp Lys Gln Ser Arg Gly Arg Gly Val
                165                 170                 175

Met Val Val Leu Asn Asp Arg Ile Gly Ser Ala Arg Tyr Ile Thr Lys
            180                 185                 190

Thr Asn Ala Ser Thr Leu Asp Thr Phe Lys Ala Asn Glu Glu Gly Tyr
        195                 200                 205

Leu Gly Val Ile Ile Gly Asn Arg Ile Tyr Tyr Gln Asn Arg Ile Asp
    210                 215                 220

Lys Leu His Thr Thr Arg Ser Val Phe Asp Val Arg Gly Leu Thr Ser
225                 230                 235                 240

Leu Pro Lys Val Asp Ile Leu Tyr Gly Tyr Gln Asp Asp Pro Glu Tyr
                245                 250                 255

Leu Tyr Asp Ala Ala Ile Gln His Gly Val Lys Gly Ile Val Tyr Ala
            260                 265                 270

Gly Met Gly Ala Gly Ser Val Ser Val Arg Gly Ile Ala Gly Met Arg
        275                 280                 285

Lys Ala Met Glu Lys Gly Val Val Val Ile Arg Ser Thr Arg Thr Gly
    290                 295                 300

Asn Gly Ile Val Pro Pro Asp Glu Glu Leu Pro Gly Leu Val Ser Asp
305                 310                 315                 320

Ser Leu Asn Pro Ala His Ala Arg Ile Leu Leu Met Leu Ala Leu Thr
                325                 330                 335

Arg Thr Ser Asp Pro Lys Val Ile Gln Glu Tyr Phe His Thr Tyr
            340                 345                 350


<210> SEQ ID NO 43
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Arg Asn Leu Leu Arg Gly Met Leu Val Val Ile Cys Cys Met Ala
1               5                   10                  15

Gly Ile Ala Ala Ala Ala Asp Lys Leu Pro Asn Ile Val Ile Leu Ala
            20                  25                  30

Thr Gly Gly Thr Ile Ala Gly Ser Ala Ala Thr Gly Thr Gln Thr Thr
        35                  40                  45

Gly Tyr Lys Ala Gly Ala Leu Gly Val Asp Thr Leu Ile Asn Ala Val
```

```
    50                  55                  60

Pro Glu Val Lys Lys Leu Ala Asn Val Lys Gly Glu Gln Phe Ser Asn
65                  70                  75                  80

Met Ala Ser Glu Asn Met Thr Gly Asp Val Val Leu Lys Leu Ser Gln
                85                  90                  95

Arg Val Asn Glu Leu Leu Ala Arg Asp Asp Val Asp Gly Val Val Ile
            100                 105                 110

Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
                165                 170                 175

Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Val Ile Arg Ser Thr Arg Thr Gly Asn Gly Ile
    290                 295                 300

Val Pro Pro Asp Glu Glu Leu Pro Gly Leu Val Ser Asp Ser Leu Asn
305                 310                 315                 320

Pro Ala His Ala Arg Ile Leu Leu Met Leu Ala Leu Thr Arg Thr Ser
                325                 330                 335

Asp Pro Lys Val Ile Gln Glu Tyr Phe His Thr Tyr
            340                 345


<210> SEQ ID NO 44
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Arg Asn Leu Ile Leu Ser Ala Ala Leu Val Thr Ala Ser Leu Phe
1               5                   10                  15

Gly Met Thr Ala Gln Ala Ala Asp Lys Leu Pro Asn Ile Val Ile Leu
            20                  25                  30

Ala Thr Gly Gly Thr Ile Ala Gly Ser Ala Ala Thr Gly Thr Gln Thr
        35                  40                  45

Thr Gly Tyr Lys Ala Gly Ala Leu Gly Val Asp Thr Leu Ile Asn Ala
    50                  55                  60
```

```
Val Pro Glu Val Lys Lys Leu Ala Asn Val Lys Gly Glu Gln Phe Ser
65                  70                  75                  80

Asn Met Ala Ser Glu Asn Met Thr Gly Asp Val Val Leu Lys Leu Ser
                85                  90                  95

Gln Arg Val Asn Glu Leu Leu Ala Arg Asp Asp Val Asp Gly Val Val
            100                 105                 110

Ile Thr His Gly Thr Asp Thr Val Glu Glu Ser Ala Tyr Phe Leu His
        115                 120                 125

Leu Thr Val Lys Ser Asp Lys Pro Val Val Phe Val Ala Ala Met Arg
    130                 135                 140

Pro Ala Thr Ala Ile Ser Ala Asp Gly Pro Met Asn Leu Leu Glu Ala
145                 150                 155                 160

Val Arg Val Ala Gly Asp Lys Gln Ser Arg Gly Arg Gly Val Met Val
                165                 170                 175

Val Leu Asn Asp Arg Ile Gly Ser Ala Arg Tyr Ile Thr Lys Thr Asn
            180                 185                 190

Ala Ser Thr Leu Asp Thr Phe Lys Ala Asn Glu Glu Gly Tyr Leu Gly
        195                 200                 205

Val Ile Ile Gly Asn Arg Ile Tyr Tyr Gln Asn Arg Ile Asp Lys Leu
    210                 215                 220

His Thr Thr Arg Ser Val Phe Asp Val Arg Gly Leu Thr Ser Leu Pro
225                 230                 235                 240

Lys Val Asp Ile Leu Tyr Gly Tyr Gln Asp Asp Pro Glu Tyr Leu Tyr
                245                 250                 255

Asp Ala Ala Ile Gln His Gly Val Lys Gly Ile Val Tyr Ala Gly Met
            260                 265                 270

Gly Ala Gly Ser Val Ser Val Arg Gly Ile Ala Gly Met Arg Lys Ala
        275                 280                 285

Met Glu Lys Gly Val Val Val Ile Arg Ser Thr Arg Thr Gly Asn Gly
    290                 295                 300

Ile Val Pro Pro Asp Glu Glu Leu Pro Gly Leu Val Ser Asp Ser Leu
305                 310                 315                 320

Asn Pro Ala His Ala Arg Ile Leu Leu Met Leu Ala Leu Thr Arg Thr
                325                 330                 335

Ser Asp Pro Lys Val Ile Gln Glu Tyr Phe His Thr Tyr
            340                 345
```

```
<210> SEQ ID NO 45
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Met Lys Leu Lys Arg Leu Met Ala Ala Met Thr Phe Val Ala Ala Gly
1               5                   10                  15

Val Ala Thr Val Asn Ala Val Ala Ala Asp Lys Leu Pro Asn Ile Val
            20                  25                  30

Ile Leu Ala Thr Gly Gly Thr Ile Ala Gly Ser Ala Ala Thr Gly Thr
        35                  40                  45

Gln Thr Thr Gly Tyr Lys Ala Gly Ala Leu Gly Val Asp Thr Leu Ile
    50                  55                  60

Asn Ala Val Pro Glu Val Lys Lys Leu Ala Asn Val Lys Gly Glu Gln
65                  70                  75                  80
```

```
Phe Ser Asn Met Ala Ser Glu Asn Met Thr Gly Asp Val Val Leu Lys
                85                  90                  95

Leu Ser Gln Arg Val Asn Glu Leu Leu Ala Arg Asp Asp Val Asp Gly
            100                 105                 110

Val Val Ile Thr His Gly Thr Asp Thr Val Glu Glu Ser Ala Tyr Phe
        115                 120                 125

Leu His Leu Thr Val Lys Ser Asp Lys Pro Val Val Phe Val Ala Ala
    130                 135                 140

Met Arg Pro Ala Thr Ala Ile Ser Ala Asp Gly Pro Met Asn Leu Leu
145                 150                 155                 160

Glu Ala Val Arg Val Ala Gly Asp Lys Gln Ser Arg Gly Arg Gly Val
                165                 170                 175

Met Val Val Leu Asn Asp Arg Ile Gly Ser Ala Arg Tyr Ile Thr Lys
            180                 185                 190

Thr Asn Ala Ser Thr Leu Asp Thr Phe Lys Ala Asn Glu Glu Gly Tyr
        195                 200                 205

Leu Gly Val Ile Ile Gly Asn Arg Ile Tyr Tyr Gln Asn Arg Ile Asp
    210                 215                 220

Lys Leu His Thr Thr Arg Ser Val Phe Asp Val Arg Gly Leu Thr Ser
225                 230                 235                 240

Leu Pro Lys Val Asp Ile Leu Tyr Gly Tyr Gln Asp Asp Pro Glu Tyr
                245                 250                 255

Leu Tyr Asp Ala Ala Ile Gln His Gly Val Lys Gly Ile Val Tyr Ala
            260                 265                 270

Gly Met Gly Ala Gly Ser Val Ser Val Arg Gly Ile Ala Gly Met Arg
        275                 280                 285

Lys Ala Met Glu Lys Gly Val Val Val Ile Arg Ser Thr Arg Thr Gly
    290                 295                 300

Asn Gly Ile Val Pro Pro Asp Glu Glu Leu Pro Gly Leu Val Ser Asp
305                 310                 315                 320

Ser Leu Asn Pro Ala His Ala Arg Ile Leu Leu Met Leu Ala Leu Thr
                325                 330                 335

Arg Thr Ser Asp Pro Lys Val Ile Gln Glu Tyr Phe His Thr Tyr
            340                 345                 350


<210> SEQ ID NO 46
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Pro Pro Arg Ser Ile Ala Ala Cys Leu Gly Leu Leu Gly Leu Leu
1               5                   10                  15

Met Ala Thr Gln Ala Ala Ala Ala Asp Lys Leu Pro Asn Ile Val Ile
            20                  25                  30

Leu Ala Thr Gly Gly Thr Ile Ala Gly Ser Ala Ala Thr Gly Thr Gln
        35                  40                  45

Thr Thr Gly Tyr Lys Ala Gly Ala Leu Gly Val Asp Thr Leu Ile Asn
    50                  55                  60

Ala Val Pro Glu Val Lys Lys Leu Ala Asn Val Lys Gly Glu Gln Phe
65                  70                  75                  80

Ser Asn Met Ala Ser Glu Asn Met Thr Gly Asp Val Val Leu Lys Leu
```

```
                85                  90                  95

Ser Gln Arg Val Asn Glu Leu Leu Ala Arg Asp Asp Val Asp Gly Val
            100                 105                 110

Val Ile Thr His Gly Thr Asp Thr Val Glu Glu Ser Ala Tyr Phe Leu
        115                 120                 125

His Leu Thr Val Lys Ser Asp Lys Pro Val Val Phe Val Ala Ala Met
    130                 135                 140

Arg Pro Ala Thr Ala Ile Ser Ala Asp Gly Pro Met Asn Leu Leu Glu
145                 150                 155                 160

Ala Val Arg Val Ala Gly Asp Lys Gln Ser Arg Gly Arg Gly Val Met
                165                 170                 175

Val Val Leu Asn Asp Arg Ile Gly Ser Ala Arg Tyr Ile Thr Lys Thr
            180                 185                 190

Asn Ala Ser Thr Leu Asp Thr Phe Lys Ala Asn Glu Glu Gly Tyr Leu
        195                 200                 205

Gly Val Ile Ile Gly Asn Arg Ile Tyr Tyr Gln Asn Arg Ile Asp Lys
    210                 215                 220

Leu His Thr Thr Arg Ser Val Phe Asp Val Arg Gly Leu Thr Ser Leu
225                 230                 235                 240

Pro Lys Val Asp Ile Leu Tyr Gly Tyr Gln Asp Asp Pro Glu Tyr Leu
                245                 250                 255

Tyr Asp Ala Ala Ile Gln His Gly Val Lys Gly Ile Val Tyr Ala Gly
            260                 265                 270

Met Gly Ala Gly Ser Val Ser Val Arg Gly Ile Ala Gly Met Arg Lys
        275                 280                 285

Ala Met Glu Lys Gly Val Val Val Ile Arg Ser Thr Arg Thr Gly Asn
    290                 295                 300

Gly Ile Val Pro Pro Asp Glu Glu Leu Pro Gly Leu Val Ser Asp Ser
305                 310                 315                 320

Leu Asn Pro Ala His Ala Arg Ile Leu Leu Met Leu Ala Leu Thr Arg
                325                 330                 335

Thr Ser Asp Pro Lys Val Ile Gln Glu Tyr Phe His Thr Tyr
            340                 345                 350


<210> SEQ ID NO 47
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gln Asn Tyr Lys Lys Phe Leu Leu Ala Ala Ala Val Ser Met Ala
1               5                   10                  15

Phe Ser Ala Thr Ala Met Ala Ala Asp Lys Leu Pro Asn Ile Val Ile
            20                  25                  30

Leu Ala Thr Gly Gly Thr Ile Ala Gly Ser Ala Ala Thr Gly Thr Gln
        35                  40                  45

Thr Thr Gly Tyr Lys Ala Gly Ala Leu Gly Val Asp Thr Leu Ile Asn
    50                  55                  60

Ala Val Pro Glu Val Lys Lys Leu Ala Asn Val Lys Gly Glu Gln Phe
65                  70                  75                  80

Ser Asn Met Ala Ser Glu Asn Met Thr Gly Asp Val Val Leu Lys Leu
                85                  90                  95
```

```
Ser Gln Arg Val Asn Glu Leu Leu Ala Arg Asp Asp Val Asp Gly Val
            100                 105                 110

Val Ile Thr His Gly Thr Asp Thr Val Glu Glu Ser Ala Tyr Phe Leu
        115                 120                 125

His Leu Thr Val Lys Ser Asp Lys Pro Val Val Phe Val Ala Ala Met
    130                 135                 140

Arg Pro Ala Thr Ala Ile Ser Ala Asp Gly Pro Met Asn Leu Leu Glu
145                 150                 155                 160

Ala Val Arg Val Ala Gly Asp Lys Gln Ser Arg Gly Arg Gly Val Met
                165                 170                 175

Val Val Leu Asn Asp Arg Ile Gly Ser Ala Arg Tyr Ile Thr Lys Thr
            180                 185                 190

Asn Ala Ser Thr Leu Asp Thr Phe Lys Ala Asn Glu Glu Gly Tyr Leu
        195                 200                 205

Gly Val Ile Ile Gly Asn Arg Ile Tyr Tyr Gln Asn Arg Ile Asp Lys
    210                 215                 220

Leu His Thr Thr Arg Ser Val Phe Asp Val Arg Gly Leu Thr Ser Leu
225                 230                 235                 240

Pro Lys Val Asp Ile Leu Tyr Gly Tyr Gln Asp Asp Pro Glu Tyr Leu
                245                 250                 255

Tyr Asp Ala Ala Ile Gln His Gly Val Lys Gly Ile Val Tyr Ala Gly
            260                 265                 270

Met Gly Ala Gly Ser Val Ser Val Arg Gly Ile Ala Gly Met Arg Lys
        275                 280                 285

Ala Met Glu Lys Gly Val Val Val Ile Arg Ser Thr Arg Thr Gly Asn
    290                 295                 300

Gly Ile Val Pro Pro Asp Glu Glu Leu Pro Gly Leu Val Ser Asp Ser
305                 310                 315                 320

Leu Asn Pro Ala His Ala Arg Ile Leu Leu Met Leu Ala Leu Thr Arg
                325                 330                 335

Thr Ser Asp Pro Lys Val Ile Gln Glu Tyr Phe His Thr Tyr
            340                 345                 350


<210> SEQ ID NO 48
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Lys Lys Ser Thr Leu Ala Val Ala Val Thr Leu Gly Ala Ile Ala
1               5                   10                  15

Gln Gln Ala Gly Ala Ala Asp Lys Leu Pro Asn Ile Val Ile Leu Ala
            20                  25                  30

Thr Gly Gly Thr Ile Ala Gly Ser Ala Ala Thr Gly Thr Gln Thr Thr
        35                  40                  45

Gly Tyr Lys Ala Gly Ala Leu Gly Val Asp Thr Leu Ile Asn Ala Val
    50                  55                  60

Pro Glu Val Lys Lys Leu Ala Asn Val Lys Gly Glu Gln Phe Ser Asn
65                  70                  75                  80

Met Ala Ser Glu Asn Met Thr Gly Asp Val Val Leu Lys Leu Ser Gln
                85                  90                  95

Arg Val Asn Glu Leu Leu Ala Arg Asp Asp Val Asp Gly Val Val Ile
            100                 105                 110
```

```
Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
                165                 170                 175

Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Val Ile Arg Ser Thr Arg Thr Gly Asn Gly Ile
    290                 295                 300

Val Pro Pro Asp Glu Glu Leu Pro Gly Leu Val Ser Asp Ser Leu Asn
305                 310                 315                 320

Pro Ala His Ala Arg Ile Leu Leu Met Leu Ala Leu Thr Arg Thr Ser
                325                 330                 335

Asp Pro Lys Val Ile Gln Glu Tyr Phe His Thr Tyr
            340                 345


<210> SEQ ID NO 49
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Lys Leu Lys Arg Leu Met Ala Ala Met Thr Phe Val Ala Ala Gly
1               5                   10                  15

Val Ala Thr Ala Asn Ala Val Ala Ala Asp Lys Leu Pro Asn Ile Val
            20                  25                  30

Ile Leu Ala Thr Gly Gly Thr Ile Ala Gly Ser Ala Ala Thr Gly Thr
        35                  40                  45

Gln Thr Thr Gly Tyr Lys Ala Gly Ala Leu Gly Val Asp Thr Leu Ile
    50                  55                  60

Asn Ala Val Pro Glu Val Lys Lys Leu Ala Asn Val Lys Gly Glu Gln
65                  70                  75                  80

Phe Ser Asn Met Ala Ser Glu Asn Met Thr Gly Asp Val Val Leu Lys
                85                  90                  95

Leu Ser Gln Arg Val Asn Glu Leu Leu Ala Arg Asp Asp Val Asp Gly
            100                 105                 110

Val Val Ile Thr His Gly Thr Asp Thr Val Glu Glu Ser Ala Tyr Phe
```

```
        115                 120                 125

Leu His Leu Thr Val Lys Ser Asp Lys Pro Val Val Phe Val Ala Ala
    130                 135                 140

Met Arg Pro Ala Thr Ala Ile Ser Ala Asp Gly Pro Met Asn Leu Leu
145                 150                 155                 160

Glu Ala Val Arg Val Ala Gly Asp Lys Gln Ser Arg Gly Arg Gly Val
                165                 170                 175

Met Val Val Leu Asn Asp Arg Ile Gly Ser Ala Arg Tyr Ile Thr Lys
            180                 185                 190

Thr Asn Ala Ser Thr Leu Asp Thr Phe Lys Ala Asn Glu Glu Gly Tyr
        195                 200                 205

Leu Gly Val Ile Ile Gly Asn Arg Ile Tyr Tyr Gln Asn Arg Ile Asp
    210                 215                 220

Lys Leu His Thr Thr Arg Ser Val Phe Asp Val Arg Gly Leu Thr Ser
225                 230                 235                 240

Leu Pro Lys Val Asp Ile Leu Tyr Gly Tyr Gln Asp Asp Pro Glu Tyr
                245                 250                 255

Leu Tyr Asp Ala Ala Ile Gln His Gly Val Lys Gly Ile Val Tyr Ala
            260                 265                 270

Gly Met Gly Ala Gly Ser Val Ser Val Arg Gly Ile Ala Gly Met Arg
        275                 280                 285

Lys Ala Met Glu Lys Gly Val Val Val Ile Arg Ser Thr Arg Thr Gly
    290                 295                 300

Asn Gly Ile Val Pro Pro Asp Glu Glu Leu Pro Gly Leu Val Ser Asp
305                 310                 315                 320

Ser Leu Asn Pro Ala His Ala Arg Ile Leu Leu Met Leu Ala Leu Thr
                325                 330                 335

Arg Thr Ser Asp Pro Lys Val Ile Gln Glu Tyr Phe His Thr Tyr
            340                 345                 350


<210> SEQ ID NO 50
<211> LENGTH: 6
<212> TYPE: DNA
<213> ORGANISM: Artificial Sequence
<220> FEATURE:
<223> OTHER INFORMATION: Description of Artificial Sequence: Synthetic
      consensus RBS sequence

<400> SEQUENCE: 50

aggagg                                                                  6


<210> SEQ ID NO 51
<211> LENGTH: 6
<212> TYPE: DNA
<213> ORGANISM: Unknown
<220> FEATURE:
<223> OTHER INFORMATION: Description of Unknown:
      RBS2 sequence

<400> SEQUENCE: 51

ggagcg                                                                  6


<210> SEQ ID NO 52
<211> LENGTH: 6
<212> TYPE: DNA
<213> ORGANISM: Unknown
<220> FEATURE:
<223> OTHER INFORMATION: Description of Unknown:
      RBS34 sequence
```

<400> SEQUENCE: 52 ggagcg 6

<210> SEQ ID NO 53
<211> LENGTH: 6
<212> TYPE: DNA
<213> ORGANISM: Unknown
<220> FEATURE:
<223> OTHER INFORMATION: Description of Unknown:
RBS41 sequence

<400> SEQUENCE: 53 aggagt 6

<210> SEQ ID NO 54
<211> LENGTH: 6
<212> TYPE: DNA
<213> ORGANISM: Unknown
<220> FEATURE:
<223> OTHER INFORMATION: Description of Unknown:
RBS43 sequence

<400> SEQUENCE: 54 ggagtg 6

<210> SEQ ID NO 55
<211> LENGTH: 6
<212> TYPE: DNA
<213> ORGANISM: Unknown
<220> FEATURE:
<223> OTHER INFORMATION: Description of Unknown:
RBS48 sequence

<400> SEQUENCE: 55 gagtaa 6

<210> SEQ ID NO 56
<211> LENGTH: 6
<212> TYPE: DNA
<213> ORGANISM: Unknown
<220> FEATURE:
<223> OTHER INFORMATION: Description of Unknown:
RBS1 sequence

<400> SEQUENCE: 56 agagag 6

<210> SEQ ID NO 57
<211> LENGTH: 6
<212> TYPE: DNA
<213> ORGANISM: Unknown
<220> FEATURE:
<223> OTHER INFORMATION: Description of Unknown:
RBS35 sequence

<400> SEQUENCE: 57 aaggca 6

<210> SEQ ID NO 58
<211> LENGTH: 6
<212> TYPE: DNA
<213> ORGANISM: Unknown
<220> FEATURE:
<223> OTHER INFORMATION: Description of Unknown:
RBS49 sequence

<400> SEQUENCE: 58

```
ccgaac                                                                 6


<210> SEQ ID NO 59
<211> LENGTH: 167
<212> TYPE: PRT
<213> ORGANISM: Pseudomonas fluorescens

<400> SEQUENCE: 59

Met Arg Lys Leu Thr Gln Leu Val Leu Leu Ala Thr Val Leu Val Thr
1               5                   10                  15

Thr Pro Ala Phe Ala Glu Met Lys Ile Ala Val Leu Asn Tyr Gln Met
            20                  25                  30

Ala Leu Leu Glu Ser Asp Ala Ala Lys Arg Tyr Ala Val Asp Ala Glu
        35                  40                  45

Lys Lys Phe Gly Pro Gln Leu Thr Lys Leu Lys Thr Leu Glu Ser Ser
    50                  55                  60

Ala Lys Gly Ile Gln Asp Arg Leu Val Ala Gly Gly Asp Lys Met Gln
65                  70                  75                  80

Gln Gly Glu Arg Glu Arg Leu Glu Leu Glu Phe Lys Gln Lys Ala Arg
                85                  90                  95

Asp Tyr Gln Phe Gln Ser Lys Glu Leu Asn Glu Ala Lys Ala Val Ala
            100                 105                 110

Asp Arg Glu Met Leu Lys Gln Leu Lys Pro Lys Leu Asp Ser Ala Val
        115                 120                 125

Glu Glu Val Ile Lys Lys Gly Ala Phe Asp Leu Val Phe Glu Arg Gly
    130                 135                 140

Ala Val Ile Asp Val Lys Pro Gln Tyr Asp Ile Thr Arg Gln Val Ile
145                 150                 155                 160

Glu Arg Met Asn Gln Leu Lys
                165


<210> SEQ ID NO 60
<211> LENGTH: 504
<212> TYPE: DNA
<213> ORGANISM: Pseudomonas fluorescens

<400> SEQUENCE: 60

gtgcgtaagt tgactcaatt ggtcttgctg gccactgtgc tggtcaccac cccggccttc      60

gccgaaatga aaatcgccgt tctgaactat cagatggccc tgctggaatc cgatgcggcc     120

aagcgatacg ccgtggatgc cgagaagaag ttcggtccgc aactgaccaa gctcaagaca     180

ctggaaagca gcgccaaagg catccaggac cgcctggtag ccggtggcga caagatgcag     240

caaggcgagc gcgagcgtct ggagcttgaa ttcaagcaaa aggcccgtga ctaccagttc     300

caatccaagg agctgaacga agccaaggct gtggccgacc gcgaaatgct caagcagctc     360

aagcctaaat tggacagcgc tgtggaagaa gtcatcaaga agggtgcctt tgacctggtg     420

ttcgagcgtg gcgccgtgat cgacgtcaag cctcaatacg acatcacccg ccaggtgatc     480

gagcgcatga accagctgaa gtga                                            504


<210> SEQ ID NO 61
<211> LENGTH: 325
<212> TYPE: PRT
<213> ORGANISM: Pseudomonas fluorescens

<400> SEQUENCE: 61

Met Gln Ser Ala Asn Asn Val Met Val Leu Tyr Thr Gly Gly Thr Ile
```

-continued

```
1               5                   10                  15

Gly Met Gln Ala Ser Ala Asn Gly Leu Ala Pro Ala Ser Gly Phe Glu
            20                  25                  30

Val Arg Met Arg Glu Gln Phe Ala Gly Ala Asp Leu Pro Ala Trp Arg
        35                  40                  45

Phe Gln Glu Met Ser Pro Leu Ile Asp Ser Ala Asn Met Asn Pro Ala
    50                  55                  60

Tyr Trp Gln Arg Leu Arg Ser Ala Val Val Glu Ala Val Asp Ala Gly
65                  70                  75                  80

Cys Asp Ala Val Leu Ile Leu His Gly Thr Asp Thr Leu Ala Tyr Ser
                85                  90                  95

Ala Ala Ala Met Ser Phe Gln Leu Leu Gly Leu Pro Ala Pro Val Val
            100                 105                 110

Phe Thr Gly Ser Met Leu Pro Ala Gly Val Pro Asp Ser Asp Ala Trp
        115                 120                 125

Glu Asn Val Ser Gly Ala Leu Thr Ala Leu Gly Glu Gly Leu Lys Pro
    130                 135                 140

Gly Val His Leu Tyr Phe His Gly Ala Leu Met Ala Pro Thr Arg Cys
145                 150                 155                 160

Ala Lys Ile Arg Ser Phe Gly Arg Asn Pro Phe Ala Ala Leu Gln Arg
                165                 170                 175

Asn Gly Gly Val Ala Leu Ala Asp Lys Leu Pro Ala Ala Leu Ala Tyr
            180                 185                 190

Arg Asn Asp Lys Ala Pro Ala Asn Val Gly Val Leu Pro Leu Val Pro
        195                 200                 205

Gly Ile Ala Ala Ala Gln Leu Asp Ala Leu Ile Asp Ser Gly Ile Gln
    210                 215                 220

Ala Leu Val Leu Glu Cys Phe Gly Ser Gly Thr Gly Pro Ser Asp Asn
225                 230                 235                 240

Pro Ala Phe Leu Ala Ser Leu Lys Arg Ala Gln Asp Gln Glu Val Val
                245                 250                 255

Val Val Ala Ile Thr Gln Cys His Glu Gly Gly Val Glu Leu Asp Val
            260                 265                 270

Tyr Glu Ala Gly Ser Arg Leu Arg Ser Val Gly Val Leu Ser Gly Gly
        275                 280                 285

Gly Met Thr Arg Glu Ala Ala Phe Gly Lys Leu Asn Ala Leu Ile Gly
    290                 295                 300

Ala Gly Leu Asp Ser Ala Glu Ile Arg Arg Leu Val Glu Leu Asp Leu
305                 310                 315                 320

Cys Gly Glu Leu Ser
                325


<210> SEQ ID NO 62
<211> LENGTH: 362
<212> TYPE: PRT
<213> ORGANISM: Pseudomonas fluorescens

<400> SEQUENCE: 62

Met Lys Ser Ala Leu Lys Asn Val Ile Pro Gly Ala Leu Ala Leu Leu
1               5                   10                  15

Leu Leu Phe Pro Val Ala Ala Gln Ala Lys Glu Val Glu Ser Lys Thr
            20                  25                  30

Lys Leu Ser Asn Val Val Ile Leu Ala Thr Gly Gly Thr Ile Ala Gly
        35                  40                  45
```

```
Ala Gly Ala Ser Ala Ala Asn Ser Ala Thr Tyr Gln Ala Ala Lys Val
    50                  55                  60

Gly Ile Glu Gln Leu Ile Ala Gly Val Pro Glu Leu Ser Gln Ile Ala
65                  70                  75                  80

Asn Val Arg Gly Glu Gln Val Met Gln Ile Ala Ser Glu Ser Ile Asn
                85                  90                  95

Asn Glu Asn Leu Leu Gln Leu Gly Arg Arg Val Ala Glu Leu Ala Asp
            100                 105                 110

Asn Lys Asp Val Asp Gly Ile Val Ile Thr His Gly Thr Asp Thr Leu
        115                 120                 125

Glu Glu Thr Ala Tyr Phe Leu Asn Leu Val Glu Lys Thr Asp Lys Pro
    130                 135                 140

Ile Val Val Val Gly Ser Met Arg Pro Gly Thr Ala Met Ser Ala Asp
145                 150                 155                 160

Gly Met Leu Asn Leu Tyr Asn Ala Val Ala Val Ala Gly Ser Lys Glu
                165                 170                 175

Ala Arg Gly Lys Gly Val Leu Val Thr Met Asn Asp Glu Ile Gln Ser
            180                 185                 190

Gly Arg Asp Val Ser Lys Met Ile Asn Ile Lys Thr Glu Ala Phe Lys
        195                 200                 205

Ser Pro Trp Gly Pro Met Gly Met Val Val Glu Gly Lys Ser Tyr Trp
    210                 215                 220

Phe Arg Leu Pro Ala Lys Arg His Thr Met Asp Ser Glu Phe Asp Ile
225                 230                 235                 240

Lys Thr Ile Lys Ser Leu Pro Asp Val Glu Ile Ala Tyr Gly Tyr Gly
                245                 250                 255

Asn Val Ser Asp Thr Ala Tyr Lys Ala Leu Ala Gln Ala Gly Ala Lys
            260                 265                 270

Ala Ile Ile His Ala Gly Thr Gly Asn Gly Ser Val Ser Ser Lys Val
        275                 280                 285

Val Pro Ala Leu Val Glu Leu Arg Lys Gln Gly Val Gln Ile Ile Arg
    290                 295                 300

Ser Ser His Val Asn Ala Gly Gly Met Val Leu Arg Asn Ala Glu Gln
305                 310                 315                 320

Pro Asp Asp Lys Tyr Asp Trp Val Ala Ala Leu Asp Leu Asn Pro Gln
                325                 330                 335

Lys Ala Arg Ile Leu Ala Met Val Ala Leu Thr Lys Thr Gln Asp Ser
            340                 345                 350

Lys Glu Leu Gln Arg Ile Phe Trp Glu Tyr
        355                 360
```

```
<210> SEQ ID NO 63
<211> LENGTH: 1020
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

atatgctctt cagccgcaga caaactccct aacatcgtaa tcctcgcaac tggtggtacc      60

atcgcaggca gcgccgccac cggcacgcag accactggct acaaggccgg cgcgctgggc     120

gtagacacgc tgatcaacgc cgtcccggaa gtgaagaaac tggccaacgt caagggtgag     180

caattctcca acatggccag cgagaacatg actggcgatg tggtactgaa gctctcgcag     240
```

-continued

```
cgcgtgaacg aactgctcgc ccgcgacgac gtggacggcg tggtgatcac ccacggcact    300

gataccgtcg aagagtcggc gtactttctc cacctgaccg tgaagtccga taagcccgtg    360

gtgtttgtcg ccgcgatgcg cccggcgacc gccatcagcg ccgacgggcc gatgaatctg    420

ttggaagccg tgcgcgtggc gggtgacaag caaagccgcg gtcggggcgt aatggtcgtc    480

ctgaacgatc ggatcggtag cgcgcggtac atcaccaaga cgaacgcctc cacgctggac    540

accttcaagg cgaacgaaga ggggtacctg gggtgatca ttggcaatcg tatctattac    600

cagaaccgca tcgacaagct gcacaccacc cgctcggtgt tcgacgtgcg cggtctgact    660

agcctgccca aggtcgacat cctgtacggc taccaagacg acccggagta cctctacgac    720

gcggcgatcc agcatggcgt gaagggcatc gtctacgccg gtatgggtgc cggctcggtg    780

tcggtccgcg gcatcgcggg tatgcgcaag gccatggaga aaggcgtggt cgtgattcgc    840

tcgacccgga ctggcaatgg catcgtaccg cccgatgaag aactcccggg gctcgtgagc    900

gatagcctca accccgcgca cgcccggatc ctgctgatgc tggcgctcac gcggaccagc    960

gaccccaagg tcattcaaga gtacttccac acctactgat aatagttcag aagagcatat   1020
```

METHOD FOR PRODUCTION OF RECOMBINANT *ERWINIA ASPARAGINASE*

CROSS-REFERENCE TO RELATED APPLICATIONS

This application claims benefit of U.S. Provisional Application No. 62/578,305, filed Oct. 27, 2017, which is incorporated herein by reference.

SEQUENCE LISTING

The instant application contains a Sequence Listing which has been submitted electronically in ASCII format and is hereby incorporated by reference in its entirety. Said ASCII copy, created on Oct. 16, 2018, is named 38194-749_201_SL.txt and is 71,227 bytes in size.

BACKGROUND OF THE INVENTION

L-asparaginase type II from the bacterium *Erwinia chrysanthemi*, also called crisantaspase, is indicated in combination with other chemotherapeutic agents for treatment of patients with acute lymphoblastic leukemia (ALL) who have developed hypersensitivity or silent inactivation to native or pegylated asparaginase derived from *E. coli*. It may also be used to treat other neoplastic conditions. Crisantaspase is manufactured by fermentation of *Erwinia chrysanthemi* to produce cell paste which is processed to yield an enzyme preparation which is further purified through a series of chromatography and other methods to yield a drug substance. When expressed in *Erwinia*, crisantaspase pre-protein uses its native secretory signal sequence present at the N-terminus for secretion to the periplasmic space of the cells. Once localized within the periplasmic space, the signal sequence is cleaved off to yield the mature monomer that is capable of spontaneously merging into the tetrameric, or active, form of crisantaspase. Recombinant crisantaspase, in some cases, is expressed in *E. coli* using fusions with various secretion signal peptides from heterologous sources.

SUMMARY OF THE INVENTION

Provided herein are methods for producing a recombinant type II asparaginase. In some embodiments, the method comprises: culturing a Pseudomonadales host cell in a culture medium and expressing the recombinant asparaginase in the cytoplasm of the Pseudomonadales host cell from an expression construct comprising a nucleic acid encoding the recombinant asparaginase, wherein the recombinant asparaginase is produced in the cytoplasm at a yield of about 20% TCP to about 40% TCP soluble asparaginase. In some embodiments, the recombinant asparaginase is produced in the cytoplasm at a yield of about 10 g/L to about 25 g/L. In some embodiments, the method further comprises measuring the activity of an amount of the soluble recombinant type II asparaginase produced, using an activity assay. In some embodiments, the nucleic acid encoding the recombinant asparaginase is optimized for expression in the host cell. In some embodiments, the recombinant asparaginase is an *Erwinia chrysanthemi* L-asparaginase type II (crisantaspase). In some embodiments, the nucleic acid encoding the recombinant asparaginase comprises a sequence at least 85% homologous to SEQ ID NO: 1. In some embodiments, the recombinant asparaginase has an amino acid sequence at least 85% homologous to SEQ ID NO: 2. In some embodiments, expression of the recombinant asparaginase is induced by addition of IPTG to the culture medium. In some embodiments, the IPTG is at a concentration in the culture medium of about 0.05 mM to about 2.5 mM. In some embodiments, expression of the recombinant asparaginase is induced when the Pseudomonad host cell has grown to a wet cell weight of about 0.1 g/g to about 0.5 g/g. In some embodiments, the Pseudomonadales host cell is cultured at a pH of about 5.0 to about 8.0. In some embodiments, the Pseudomonadales host cell is cultured at a temperature of about 22° C. to about 33° C. In any embodiment herein, the Pseudomonadales host cell is a *Pseudomonas fluorescens* cell. In some embodiments, the Pseudomonadales host cell is deficient in the expression of one or more asparaginases. In some embodiments, the Pseudomonadales host cell is deficient in the expression of one or more native asparaginases. In some embodiments, the deficiently expressed native asparaginase is a type I asparaginase. In some embodiments, the deficiently expressed native asparaginase is a type II asparaginase. In some embodiments, the Pseudomonadales host cell is deficient in the expression of one or more proteases. In some embodiments, the Pseudomonadales host cell overexpresses one or more folding modulators. In some embodiments, the Pseudomonadales host cell is deficient in the expression of one or more native asparaginases, is deficient in the expression of one or more proteases and/or overexpresses one or more folding modulators.

In embodiments, the method comprises: culturing a Pseudomonadales host cell in a culture medium and expressing the recombinant asparaginase in the periplasm of the Pseudomonadales host cell from an expression construct comprising a nucleic acid encoding the recombinant asparaginase; wherein the recombinant asparaginase is produced in the periplasm at a yield of about 20% to about 40% TCP soluble asparaginase, e.g., monomeric asparaginase. In some embodiments, the recombinant asparaginase is produced in the periplasm at a yield of about 5 g/L to about 20 g/L. In some embodiments, the method further comprises measuring the activity of an amount of the recombinant type II asparaginase produced, using an activity assay. In some embodiments, the nucleic acid encoding the recombinant asparaginase is optimized for expression in the host cell. In some embodiments, the recombinant asparaginase is an *Erwinia chrysanthemi* L-asparaginase type II (crisantaspase). In some embodiments, the nucleic acid encoding the recombinant asparaginase comprises a sequence at least 85% homologous to SEQ ID NO: 1. In some embodiments, the recombinant asparaginase has an amino acid sequence at least 85% homologous to SEQ ID NO: 2. In some embodiments, expression of the recombinant asparaginase is induced by addition of IPTG to the culture medium. In some embodiments, he IPTG is at a concentration in the culture medium of about 0.05 mM to about 2.5 mM. In some embodiments, expression of the recombinant asparaginase is induced when the Pseudomonadales host cell has grown to a wet weight of about 0.05 g/g to about 0.5 g/g. In some embodiments, the Pseudomonadales host cell is cultured at a pH of about 5.0 to about 8.0. In some embodiments, the Pseudomonadales host cell is cultured at a temperature of about 22° C. to about 33° C. In some embodiments, the Pseudomonadales host cell is a *Pseudomonas fluorescens* cell. In some embodiments, the Pseudomonadales host cell is deficient in the expression of one or more native asparaginases. In some embodiments, the deficiently expressed native asparaginase is a type I asparaginase. In some embodiments, the deficiently expressed native asparaginase is a type II asparaginase. In some embodiments, the Pseudomonadales host cell is deficient in the expression of one or more proteases. In some embodiments, the Pseudomonadales host cell overexpresses one or more folding modulators. In some embodiments, the expression construct comprises a secretion leader. In some embodiments, the secretion leader is selected from the group comprising the Pseudmonadales secretion leaders FlgI, Ibps31A, PbpA20V, DsbC, 8484, and 5193. In some embodiments, the secretion leader directs transfer of the recombinant asparaginase produced to the periplasm of the Pseudomonad host cell. In some embodiments, the method further comprises comparing the measured activity of the recombinant type II asparaginase produced, with an activity measured in the same amount of a control type II asparaginase using the same activity assay. In some embodiments, the control type II asparaginase comprises an *Erwinia* type II asparaginase that has been commercially approved for use in patients in at least one country. In some embodiments, the recombinant type II asparaginase produced is selected for use in patients when it has about 80% to about 120% of the activity of the type II asparaginase control sample. In some embodiments, the recombinant type II asparaginase is modified to increase half-life in patients. In embodiments, the host cell is selected from at least one of: a host cell that is deficient in HslUV protease, a host cell that is deficient in PrtB protease, a host cell that is deficient in Prc protease, a host cell that is deficient in DegP protease, a host cell that is deficient in AprA protease, a host cell that is deficient in Lon protease, a host cell that is deficient in La protease, a host cell that is deficient in Deg P1, a host cell that is deficient in Deg P2, and a host cell that overexpresses DegP2 S219A.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2. Crisantaspase Example Sequences. An exemplary nucleic acid sequence encoding crisantaspase (SEQ ID NO: 2) is shown with the corresponding amino acid sequence (SEQ ID NO: 1). The full nucleic acid sequence, including SapI restriction sites, is also shown (SEQ ID NO: 63).

DETAILED DESCRIPTION OF THE INVENTION

Overview

Figure 1:
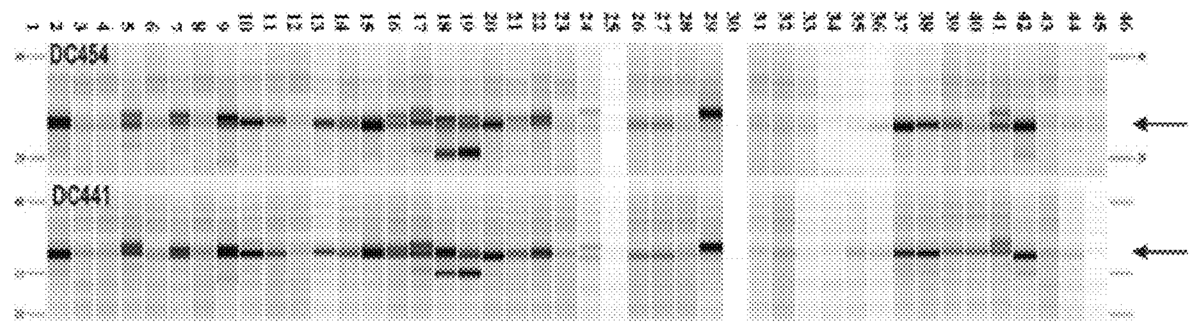
FIG. 1. SDS-CGE Gel-like Images—Tier 1 Expression Plasmid Screen. Crisantaspase small scale growth whole broth sonicate soluble samples from DC454 (upper panel) and DC441 (lower panel) were analyzed by reduced SDS-CGE. The lane at the far left shows molecular weight marker ladder 1 (upper panel MW ladder 48 KD, 29 KD; lower panel MW ladder 48 KD, 29 KD, 21 KD), and the lane at the far right shows the same ladders. From left to right (lanes 1 to 46), beginning immediately to the right of ladder 1 are lanes showing the expression patterns observed when the following secretion leader peptides were fused to the N-terminus of crisantaspase protein (high RBS except as otherwise indicated): no leader; DsbD; Leader A; DsbA; DsbA-Medium RBS; Azu; Azu-Medium RBS; Lao; Ibp-S31A; TolB; DC432 null (wild type host strain carrying vector only plasmid); Tpr; Ttg2C; FlgI; CupC2; CupB2; Pbp; PbpA20V; DsbC; Leader B; Leader C; DC432 null; Leader D; Leader E; Leader F; Leader G; Leader H; PorE; Leader I; Leader J; Leader K; Leader L; DC432 null; Leader M; Leader N; Leader O; 5193; Leader P; Leader Q; Leader R; 8484; Leader S; Leader T; DC432 null. The arrows to the right of the gel image indicate migration of the crisantaspase target protein (35 kDa).

Disclosed herein are methods for producing soluble recombinant L-asparaginase type II from *Erwinia chrysanthemi*, also known as crisantaspase, in a *Pseudomonas* host cell. High levels of crisantaspase production as a percentage of total cell protein are described herein, for example up to 40% TCP crisantaspase, e.g., crisantaspase monomer, with no detectable degradation, capable of forming active tetramer. High titers of crisantaspase production are obtained using the methods of the invention, for example, up to 20 grams per liter of crisantaspase, e.g., crisantaspase monomer, with no detectable degradation, capable of forming active tetramer. Host cells for producing crisantaspase include but are not limited to *Pseudomonas*, for example

*Pseudomonas fluorescens*. The crisantaspase expression construct can be codon-optimized according to the selected host strain.

Nucleic acid constructs useful in the methods of the invention can encode a crisantaspase gene operably linked to a nucleic acid sequence encoding a secretion signal (secretion leader), e.g., a periplasmic secretion leader native to *P. fluorescens*, resulting in expression of a secretion leader-crisantaspase fusion protein. In some embodiments, a periplasmic secretion leader comprises one or more of FlgI, 8484, DsbC, Ibp-S31A, or 5193. In embodiments, the host cell has a mutation in one or more protease-encoding genes, resulting in the inactivation of the protease. It is understood that a mutation resulting in inactivation of a protease or any other gene product can be any type of mutation known in the art to cause protein inactivation or prevent protein expression including but not limited to a substitution, insertion, or deletion mutation in either the coding sequence or a regulatory sequence of the gene. It is understood that overexpression of a folding modulator can be achieved using any method known in the art, e.g., by plasmid expression or chromosomal integration of the folding modulator gene. In embodiments, the host cell has at least one protease inactivation and overexpresses at least one folding modulator.

As known to those of skill in the art, an amino acid sequence can be encoded by different nucleotide sequences due to the redundancy in the genetic code. The present invention thus includes the use of peptides or proteins that have the same amino acid sequences but are encoded by different nucleotide sequences.

In embodiments, the secretion leader transports soluble crisantaspase to the periplasm of the host cell. In other embodiments, the crisantaspase is retained in the cytoplasm. In embodiments, the crisantaspase purification process does not require crisantaspase solubilization and subsequent refolding. In embodiments, at least a portion of crisantaspase is not expressed in inclusion bodies. In embodiments, recombinant crisantaspase is expressed devoid of any peptide tag for purification and does not require additional processing upon purification. In embodiments wherein a secretion leader is fused to the asparaginase protein, the secretion leader is efficiently processed from the solubly expressed crisantaspase. In other embodiments, an expression plasmid for periplasmic production of crisantaspase does not utilize any antibiotic resistance marker gene for selection and maintenance, thus eliminating complicated processes for subsequent removal of plasmid DNA required for production of biopharmaceuticals. In other embodiments, fermentation conditions are scalable for large-volume production. The methods provided herein yield high levels of soluble and/or active crisantaspase.

In embodiments, the present invention provides methods for cytoplasmic production of a recombinant protein in soluble form at high yields, wherein the recombinant protein is periplasmically produced at lower yields in its native host. In its native host, *Erwinia chrysanthemi*, crisantaspase is produced in the periplasm. The present invention provides methods that allow production of high levels of soluble and/or active crisantaspase in the cytoplasm of the host cell. In embodiments, methods provided herein yield high levels of soluble and/or active crisantaspase in the cytoplasm of a Pseudomonadales, Pseudomonad, *Pseudomonas*, or *Pseudomonas fluorescens* host cell.

Cytoplasmic production of a recombinant protein can facilitate purification. For larger proteins (the crisantaspase tetramer is 35KD×4, i.e., a 140KD complex), a lower percent recovery from the periplasmic space using a periplasmic release is expected compared to a total release from the cytoplasm. Furthermore, incomplete or improper processing of the secretion leader in a periplasmically expressed protein can result in unwanted product-related impurities that must be separated from the target protein, resulting in overall lower process yield.

Asparaginases

Asparaginases, including type II L-asparaginases, are enzymes that catalyze the hydrolysis of L-asparagine to L-aspartate and ammonia (L-asparagine+$H_2O$=L-aspartate+$NH_3$). Type II L-asparaginases are used as a part of a multi-agent chemotherapeutic regimen to treat ALL and some other cancers. Certain cancer cells are unable to synthesize the asparagine due to a lack of asparagine synthetase, while normal cells can to synthesize asparagine. Therefore, administration of asparaginase to a patient results in hydrolysis of soluble asparagine and a reduction in circulating asparagine. This can lead to death of the cancer cells with a lesser effect on normal cells. Asparaginases are described in, e.g., Pritsa and Kyriakidis, 2002, "L-Asparaginase: Structure, Properties, and Anti-Tumor Activity," in "Drug Discovery and Design: Medical Aspects," IOS Press, Matsoukas, J., and Mavromoustakos, T., eds., incorporated herein by reference.

Erwinaze® (Biologic License Application 125359) is an *Erwinia chrisanthemi* L-asparaginase type II product commercially approved in the United States for treatment of ALL in patients. Its active ingredient is *Erwinia chrysanthemi* L-asparaginase type II (see Erwinaze® package insert, incorporated herein by reference).

In embodiments, the *Erwinia chrysanthemi* asparaginase type II (e.g., amino acid sequence set forth in SEQ ID NO: 1 herein, or any of SEQ ID NOS: 35-49, which include secretion leader sequences) is produced using the methods of the invention. In some embodiments, the *Erwinia chrysanthemi* asparaginase type II has an amino acid sequence that is at least about 70%, 75%, 80%, 85%, 90%, 95%, 96%, 97%, 98%, or 99% identical to SEQ ID NO: 1. This asparaginase is described, e.g., in U.S. Pat. Appl. No. U.S. 2016/0060613, "Pegylated L-asparaginase" incorporated by reference in its entirety, including common structural features of known L-asparaginases from bacterial sources. According to US 2016/0060613, all are homotetramers with four active sites between the N- and C-terminal domains of two adjacent monomers, all have a high degree of similarity in their tertiary and quaternary structures, and the sequences of the catalytic sites of L-asparaginases are highly conserved between *Erwinia chrysanthemi, Erwinia carotovora*, and *E. coli* L-asparaginase II. In embodiments, the protein is the L-asparaginase of *Erwinia chrysanthemi* having the sequence of SEQ ID NO: 1. This L-asparaginase is disclosed as *Erwinia chrysanthemi* NCPPB 1066 (Genbank Accession No. CAA32884, described by, e.g., Minton, et al., 1986, "Nucleotide sequence of the *Erwinia chrysanthemi* NCPPB 1066 L-asparaginase gene," Gene 46(1), 25-35, each incorporated herein by reference in its entirety), either with or without signal peptides and/or leader sequences.

In embodiments, a crisantaspase produced using the methods of the invention is a variant of the *Erwinia chrysanthemi* asparaginase L-asparaginase type II enzyme, wherein the variant has about 80% to about 120%, or greater, about 85% to about 120%, about 90% to about 120%, about 95% to about 120%, about 98% to about 120%, about 100% to about 120%, about 80% to about 100%, about 80% to about 90%, about 85% to about 115%, about 90% to about 110%, about 95% to about 155%, at least about 80%, at least about 85%, at least about 90%, at least about 95%, at least about 98%, or at least about 100%, of the L-asparaginase type II activity of the *Erwinia chrysanthemi* L-asparaginase type II enzyme.

In embodiments, the *Erwinia chrysanthemi* asparaginase type II is encoded by a nucleic acid having a sequence wherein the codons are optimized for expression in the host cell as desired. In some embodiments, the *Erwinia chrysanthemi* asparaginase type II is encoded by a nucleic acid having a sequence of SEQ ID NO: 2. In some embodiments, the *Erwinia chrysanthemi* asparaginase type II is encoded by a nucleic acid having a sequence at least about 70%, 75%, 80%, 85%, 90%, 95%, 96%, 97%, 98%, or 99% identical to SEQ ID NO: 2.

In embodiments, a type II asparaginase produced using the methods of the invention is encoded by a nucleic acid sequence that is at least about 70% identical to a wild type *Erwinia chrysanthemi* asparaginase gene. In embodiments, the asparaginase has an amino acid sequence that is at least about 70% identical to a wild type *Erwinia chrysanthemi* asparaginase. In some embodiments, a recombinant asparaginase has a nucleic acid sequence that is at least about 70%, 75%, 80%, 85%, 90%, 95%, 96%, 97%, 98%, or 99% identical to a wild type *Erwinia chrysanthemi* asparaginase nucleic acid sequence. In some embodiments, a recombinant asparaginase has an amino acid sequence encoded by a nucleic acid that is at least about 70%, 75%, 80%, 85%, 90%, 95%, 96%, 97%, 98%, or 99% identical to a wild type *Erwinia chrysanthemi* asparaginase nucleic acid sequence. "Identity" or "homology" expressed as a percentage herein describes a measure of similarity between two sequences. The extent of identity between two sequences, in some embodiments, is ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., J. Mol. Biol. 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981)).

Recombinant type II asparaginase from *Erwinia chrysanthemi*, crisantaspase, is also known as Erwinase® and Erwinaze®. Recombinant asparaginase derived from *E. coli* is known by the names Colaspase®, Elspar®, Kidrolase®, Leunase®, and Spectrila®. Pegaspargase® is the name for a pegylated version of *E. coli* asparaginase. Crisantaspase is administered to patients with acute lymphoblastic leukemia, acute myeloid leukemia, and non-Hodgkin's lymphoma via intravenous, intramuscular, or subcutaneous injection.

Asparaginase type II products commercially approved for patient use can be identified by accessing product information for asparaginase products available from respective countries' drug approval agencies. For example, product information and approval records are publicly available in the United States for, e.g., Elspar (*E. coli* L-asparagine amidohydrolase, type EC-2; BLA #101063) and Erwinaze® (asparaginase *Erwinia chrysanthemi*, BLA #125359) from the U.S. Food and Drug Administration and are incorporated herein by reference (10903 New Hampshire Avenue, Silver Spring, Md. 20993, and online at the FDA website). Product information in Europe is available from the European Medicines Agency (30 Churchill Place, Canary Wharf, London E14 5EU, United Kingdom, and online at the EMA website) (see, e.g., Oncaspar: EPAR product information, first published 19 Jan. 2016, relating to pegylated *E. coli* L-asparaginase; Spectrila: EPAR product information, first published 28 Jan. 2016; and List of nationally authorised medicinal products, 27 Apr. 2016, European Medicines Agency, each incorporated herein by reference).

In some embodiments, modified versions of crisantaspase are generated. In general, with respect to an amino acid sequence, the term "modification" includes substitutions, insertions, elongations, deletions, and derivatizations alone or in combination. In certain embodiments, modified versions of crisantaspase have enhanced properties, such as increased half-life when administered to a patient. In some embodiments, modified versions of crisantaspase with increased half-life are pegylated. In some embodiments, the crisantaspase may include one or more modifications of a "non-essential" amino acid residue. In this context, a "non-essential" amino acid residue is a residue that can be altered, e.g., deleted, substituted, or derivatized, in the novel amino acid sequence without abolishing or substantially reducing the activity (e.g., the enzymatic activity) of the crisantaspase (e.g., the analog crisantaspase). In some embodiments, the crisantaspase may include one or more modifications of an "essential" amino acid residue. In this context, an "essential" amino acid residue is a residue that when altered, e.g., deleted, substituted, or derivatized, in the novel amino acid sequence the activity of the reference crisantaspase is substantially reduced or abolished. In such embodiments where an essential amino acid residue is altered, the modified crisantaspase may possess an activity of crisantaspase of interest in the methods provided. The substitutions, insertions and deletions may be at the N-terminal or C-terminal end, or may be at internal portions of the protein. By way of example, the protein may include 1, 2, 3, 4, 5, 6, 7, 8, 9, 10, or more substitutions, both in a consecutive manner or spaced throughout the peptide molecule. Alone or in combination with the substitutions, the peptide may include 1, 2, 3, 4, 5, 6, 7, 8, 9, 10, or more insertions, again either in consecutive manner or spaced throughout the peptide molecule. The peptide, alone or in combination with the substitutions and/or insertions, may also include 1, 2, 3, 4, 5, 6, 7, 8, 9, 10, or more deletions, again either in consecutive manner or spaced throughout the peptide molecule. The peptide, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or unnatural. Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

Expression Systems

Methods herein, in some cases, comprise expressing recombinant crisantaspase from an expression construct in a *Pseudomonas* host cell. The expression construct, in some cases, is a plasmid. In some embodiments, a plasmid encoding crisantaspase sequence comprises a selection marker, and host cells maintaining the plasmid are grown under selective conditions. In some embodiments, the plasmid does not comprise a selection marker. In some embodiments, the expression construct is integrated into the host cell genome. In some embodiments, the expression construct encodes crisantaspase fused to a secretion signal that directs crisantaspase to the periplasm. In some embodiments, the secretion signal is cleaved in the host cell. In some embodiments, the expression construct does not encode a secretion signal and the crisantaspase is directed to the cytoplasm.

Methods for expressing heterologous proteins, including regulatory sequences (e.g., promoters, secretion leaders, and ribosome binding sites) useful in the methods of the invention in host strains, including *Pseudomonas* host strains, are described, e.g., in U.S. Pat. No. 7,618,799, "Bacterial leader sequences for increased expression," in U.S. Pat. No. 7,985,564, "Expression systems with Sec-system secretion," in U.S. Pat. Nos. 9,394,571 and 9,580,719, both titled "Method for Rapidly Screening Microbial Hosts to Identify Certain Strains with Improved Yield and/or Quality in the Expression of Heterologous Proteins," U.S. Pat. No. 9,453,251, "Expression of Mammalian Proteins in *Pseudomonas fluorescens*," U.S. Pat. No. 8,603,824, "Process for Improved Protein Expression by Strain Engineering," and U.S. Pat. No. 8,530,171, "High Level Expression of Recombinant Toxin Proteins," each incorporated herein by reference in its entirety. In embodiments, a secretion leader used in the context of the present invention is a secretion leader as disclosed in any of U.S. Pat. Nos. 7,618,799, 7,985,564, 9,394,571, 9,580,719, 9,453,251, 8,603,824, and 8,530,171. These patents also describe bacterial host strains useful in practicing the methods herein, that have been engineered to overexpress folding modulators or wherein protease mutations have been introduced, in order to increase heterologous protein expression.

Promoters

The promoters used in accordance with the methods herein may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences are used to regulate expression of crisantaspase in accordance with the methods herein. In embodiments, inducible promoters useful in the methods herein include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism. In some embodiments, a lac promoter is used to regulate expression of crisantaspase from a plasmid. In the case of the lac promoter derivatives or family members, e.g., the tac promoter, an inducer is IPTG (isopropyl-β-D-1-thiogalactopyranoside, also called "isopropylthiogalactoside"). In certain embodiments, IPTG is added to culture to induce expression of crisantaspase from a lac promoter in a *Pseudomonas* host cell.

Common examples of non-lac-type promoters useful in expression systems according to the methods herein include, e.g., those listed in Table 1.

TABLE 1

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |
| $P_{BAD}$ | Arabinose |

See, e.g.: J. Sanchez-Romero & V. De Lorenzo, 1999, Manual of Industrial Microbiology and Biotechnology (A. Demain & J. Davies, eds.) pp. 460-74 (ASM Press, Washington, D.C.); H. Schweizer, 2001, Current Opinion in Biotechnology, 12:439-445; R. Slater & R. Williams, 2000, Molecular Biology and Biotechnology (J. Walker & R. Rapley, eds.) pp. 125-54 (The Royal Society of Chemistry, Cambridge, UK), and L.-M. Guzman, et al., 1995, J. Bacteriol. 177(14): 4121-4130, all incorporated by reference herein. A promoter having the nucleotide sequence of a promoter native to the selected bacterial host cell also may be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to methods herein. Examples of promoter regulatory proteins include: activator proteins, e.g., *E. coli* catabolite activator protein, MalT protein; AraC family transcriptional activators; repressor proteins, e.g., *E. coli* Lad proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although, in some cases, an effector compound is used throughout the cell culture or fermentation, in one embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lad gene is sometimes present in the system. The lad gene, which is normally a constitutively expressed gene, encodes the Lac repressor protein Lad protein, which binds to the lac operator of lac family promoters. Thus, where a lac family promoter is utilized, the lad gene is sometimes also included and expressed in the expression system.

Promoter systems useful in *Pseudomonas* are described in the literature, e.g., in U.S. Pat. App. Pub. No. 2008/0269070, also referenced above.

Other Regulatory Elements

In embodiments, soluble recombinant crisantaspase is present in either the cytoplasm or periplasm of the cell during production. Secretion leaders useful for targeting proteins, e.g., crisantaspase, are described elsewhere herein, and in U.S. Pat. App. Pub. No. 2008/0193974, U.S. Pat. App. Pub. No. 2006/0008877, and in U.S. patent application Ser. No. 12/610,207, referenced above. In some embodiments, expression constructs are provided that encode crisantaspase fused to a secretion leader that transport crisantaspase to the periplasm of a Pseudomonad or *Pseudomonas* cell. In some embodiments, the secretion leader the secretion leader is cleaved from the crisantaspase protein. In some embodiments, the secretion leader facilitates production of soluble crisantaspase.

In embodiments, the expression vector contains an optimal ribosome binding sequence. Modulating translation strength by altering the translation initiation region of a protein of interest can be used to improve the production of heterologous cytoplasmic proteins that accumulate mainly as inclusion bodies due to a translation rate that is too rapid. Secretion of heterologous proteins into the periplasmic space of bacterial cells can also be enhanced by optimizing rather than maximizing protein translation levels such that the translation rate is in sync with the protein secretion rate.

The translation initiation region has been defined as the sequence extending immediately upstream of the ribosomal binding site (RBS) to approximately 20 nucleotides downstream of the initiation codon (McCarthy et al. (1990) Trends in Genetics 6:78-85, herein incorporated by reference in its entirety). In prokaryotes, alternative RBS sequences can be utilized to optimize translation levels of heterologous proteins by providing translation rates that are decreased with respect to the translation levels using the canonical, or consensus, RBS sequence (AGGAGG; SEQ ID NO: 50) described by Shine and Dalgarno (Proc. Natl. Acad. Sci. USA 71:1342-1346, 1974). By "translation rate" or "translation efficiency" is intended the rate of mRNA translation into proteins within cells. In most prokaryotes, the Shine-Dalgarno sequence assists with the binding and positioning of the 30S ribosome component relative to the start codon on the mRNA through interaction with a pyrimidine-rich region of the 16S ribosomal RNA. The RBS (also referred to herein as the Shine-Dalgarno sequence) is located on the mRNA downstream from the start of transcription and upstream from the start of translation, typically from 4 to 14 nucleotides upstream of the start codon, and more typically from 8 to 10 nucleotides upstream of the start codon. Because of the role of the RBS sequence in translation, there is a direct relationship between the efficiency of translation and the efficiency (or strength) of the RBS sequence.

In some embodiments, modification of the RBS sequence results in a decrease in the translation rate of the heterologous protein. This decrease in translation rate may correspond to an increase in the level of properly processed protein or polypeptide per gram of protein produced, or per gram of host protein. The decreased translation rate can also correlate with an increased level of recoverable protein or polypeptide produced per gram of recombinant or per gram of host cell protein. The decreased translation rate can also correspond to any combination of an increased expression, increased activity, increased solubility, or increased translocation (e.g., to a periplasmic compartment or secreted into the extracellular space). In this embodiment, the term "increased" is relative to the level of protein or polypeptide that is produced, properly processed, soluble, and/or recoverable when the protein or polypeptide of interest is expressed under the same conditions, or substantially the same conditions, and wherein the nucleotide sequence encoding the polypeptide comprises the canonical RBS sequence. Similarly, the term "decreased" is relative to the translation rate of the protein or polypeptide of interest wherein the gene encoding the protein or polypeptide comprises the canonical RBS sequence. The translation rate can be decreased by at least about 5%, at least about 10%, at least about 15%, at least about 20%, about 25%, about 30%, about 35%, about 40%, about 45%, about 50%, about 55%, about 60%, about 65%, about 70, at least about 75% or more, or at least about 2-fold, about 3-fold, about 4-fold, about 5-fold, about 6-fold, about 7-fold, or greater.

In some embodiments, the RBS sequence variants described herein can be classified as resulting in high, medium, or low translation efficiency. In one embodiment, the sequences are ranked according to the level of translational activity compared to translational activity of the canonical RBS sequence. A high RBS sequence has about 60% to about 100% of the activity of the canonical sequence. A medium RBS sequence has about 40% to about 60% of the activity of the canonical sequence. A low RBS sequence has less than about 40% of the activity of the canonical sequence.

Examples of RBS sequences are shown in Table 2. The sequences were screened for translational strength using COP-GFP as a reporter gene and ranked according to percentage of consensus RBS fluorescence. Each RBS variant was placed into one of three general fluorescence ranks: High ("Hi"—100% Consensus RBS fluorescence), Medium ("Med"—46-51% of Consensus RBS fluorescence), and Low ("Lo"-16-29% Consensus RBS fluorescence).

TABLE 2

RBS Sequences

| RBS | Sequence | Binding Strength | SEQ ID NO: |
|---|---|---|---|
| Consensus | AGGAGG | High | 50 |
| RBS2 | GGAGCG | Med | 51 |
| RBS34 | GGAGCG | Med | 52 |
| RBS41 | AGGAGT | Med | 53 |
| RBS43 | GGAGTG | Med | 54 |
| RBS48 | GAGTAA | Low | 55 |

TABLE 2-continued

| RBS Sequences | | | |
|---|---|---|---|
| RBS | Sequence | Binding Strength | SEQ ID NO: |
| RBS1 | AGAGAG | Low | 56 |
| RBS35 | AAGGCA | Low | 57 |
| RBS49 | CCGAAC | Low | 58 |

An expression construct useful in practicing the methods herein include, in addition to the protein coding sequence, the following regulatory elements operably linked thereto: a promoter, a ribosome binding site (RBS), a transcription terminator, and translational start and stop signals. Useful RBSs are obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989). Further examples of methods, vectors, and translation and transcription elements, and other elements useful in the methods herein are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Host Strains

Bacterial hosts, including Pseudomonads, and closely related bacterial organisms are contemplated for use in practicing the methods herein. In certain embodiments, the Pseudomonad host cell is *Pseudomonas fluorescens*. In some cases, the host cell is an *E. coli* cell.

Host cells and constructs useful in practicing the methods herein are identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lacI gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U. S. Pat. App. Pub. No. 2009/0325230, "Protein Expression Systems," and in Schneider, et al., 2005, "Auxotrophic markers pyrF and proC, in some cases, replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that complements the pyrF deletion to restore prototrophy. In particular embodiments, a dual pyrF-proC dual auxotrophic selection marker system in a *P. fluorescens* host cell is used. A pyrF deleted production host strain as described is often used as the background for introducing other desired genomic changes, including those described herein as useful in practicing the methods herein.

In embodiments, a host cell useful in the methods of the present invention is deficient in the expression of at least one protease, overexpresses at least one folding modulator, or both. In embodiments, the host cell is not deficient in the expression of a protease and does not overexpress a folding modulator, and therefore is wild-type with respect to protease and folding modulator expression. In any of these embodiments, the host cell is additionally deficient in a native L-asparaginase. In embodiments, the deficiency in the native L-asparaginase is generated by deleting or otherwise inactivating the native L-asparaginase gene using any suitable method known in the art. In embodiments, the host cell is deficient in a native Type I L-asparaginase, a native Type II L-asparaginase, or both. In embodiments, the host cell is wild-type with respect to protease and folding modulator expression, and deficient in a native Type I L-asparaginase and a native Type II L-asparaginase. For example, a host cell useful in the methods of the invention can be generated by one of skill in the art from MB101, using known methods. In embodiments, the host cell is generated by deleting or otherwise inactivating the native Type I L-asparaginase gene, the native Type II L-asparaginase gene, or both, in MB101.

It would be understood by one of skill in the art that a production host strain useful in the methods of the present invention can be generated using a publicly available host cell, for example, *P. fluorescens* MB101, e.g., by inactivating the pyrF gene, and/or the native Type I L-asparaginase gene, and/or the native Type II L-asparaginase gene, using any of many appropriate methods known in the art and described in the literature. It is also understood that a prototrophy restoring plasmid can be transformed into the strain, e.g., a plasmid carrying the pyrF gene from strain MB214 using any of many appropriate methods known in the art and described in the literature. Additionally, in such strains proteases can be inactivated, and folding modulator overexpression constructs introduced, using methods well known in the art.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*. Host cells of the order Pseudomonadales, of the family Pseudomonadaceae, or of the genus *Pseudomonas* are identifiable by one of skill in the art and are described in the literature (e.g., Bergey's Manual of Systematics of Archaea and Bacteria (online publication, 2015)).

Other *Pseudomonas* organisms may also be useful. Pseudomonads and closely related species include Gram-negative Proteobacteria Subgroup 1, which include the group of Proteobacteria belonging to the families and/or genera described in Bergey's Manual of Systematics of Archaea and Bacteria (online publication, 2015). Table 3 presents these families and genera of organisms.

TABLE 3

Families and Genera Listed in the Part, "Gram-Negative Aerobic Rods and Cocci" (in Bergey's Manual of Systematics of Archaea and Bacteria (online publication, 2015))

| Family | Genera |
|---|---|
| Family I. Pseudomonaceae | *Gluconobacter* |
| | *Pseudomonas* |
| | *Xanthomonas* |
| | *Zoogloea* |
| Family II. Azotobacteraceae | *Azomonas* |
| | *Azotobacter* |
| | *Beijerinckia* |
| | *Derxia* |
| Family III. Rhizobiaceae | *Agrobacterium* |
| | *Rhizobium* |
| Family IV. Methylomonadaceae | *Methylococcus* |
| | *Methylomonas* |
| Family V. Halobacteriaceae | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

*Pseudomonas* and closely related bacteria are generally part of the group defined as "Gram(−) Proteobacteria Subgroup 1" or "Gram-Negative Aerobic Rods and Cocci" (Bergey's Manual of Systematics of Archaea and Bacteria (online publication, 2015)). *Pseudomonas* host strains are described in the literature, e.g., in U.S. Pat. App. Pub. No. 2006/0040352, cited above.

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey's Manual of Systematics of Archaea and Bacteria (online publication, 2015). In addition hosts include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina*, and *Methylosphaera.*

The host cell, in some cases, is selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoakaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas* alginovora; *Pseudomonas andersonii; Pseudomonas asplenii* (ATCC 23835); *Pseudomonas azelaica* (ATCC 27162); *Pseudomonas* beyerinckii (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas*

*cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*. In one embodiment, the host cell for expression of crisantaspase is *Pseudomonas fluorescens.*

The host cell, in some cases, is selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas* cedrella; *Pseudomonas cedrina; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii.*

Proteases

In one embodiment, the methods provided herein comprise using a *Pseudomonas* host cell, comprising one or more mutations (e.g., a partial or complete deletion) in one or more protease genes, to produce recombinant crisantaspase protein. In some embodiments, a mutation in a protease gene facilitates generation of recombinant crisantaspase protein.

Exemplary target protease genes include those proteases classified as Aminopeptidases; Dipeptidases; Dipeptidylpeptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component c1r55, complement component c1s55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor c, limulus clotting factor, limulus clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases have both protease and chaperone-like activity. When these proteases are negatively affecting protein yield and/or quality it is often useful to specifically delete their protease activity, and they are overexpressed when their chaperone activity may positively affect protein yield and/or quality. These proteases include, but are not limited to: Hsp100(Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

In embodiments a host strain useful for expressing a crisantaspase, in the methods of the invention is a *Pseudomonas* host strain, e.g., *P. fluorescens*, having a protease deficiency or inactivation (resulting from, e.g., a deletion, partial deletion, or knockout) and/or overexpressing a folding modulator, e.g., from a plasmid or the bacterial chromosome. In embodiments, the host strain is deficient in at least one protease selected from Lon, HslUV, DegP1, DegP2, Prc, AprA, DegP2 S219A, Prc1, and AprA. In embodiments, the host strain overexpresses a folding modulator selected from LepB, Tig, and DsbAC-Skp, (i.e., the combination of DsbA, DsbC and Skp; Skp is OmpH RXF4702.1, set forth as SEQ ID NO: 59 herein, with an example of a coding sequence set forth as SEQ ID NO: 60). In a DsbAC-Skp overexpressor host, folding modulators DsbA, DsbC and Skp (SEQ ID NOS: 25 and 26 of U.S. Pat. No. 9,394,571 and SEQ ID NO: 60 herein, respectively) can be expressed from an operon. In embodiments, the host strain is deficient in at least one protease selected from Lon, HslUV, DegP1, DegP2, Prc, AprA, DegP2 S219A, Prc1, and AprA, and overexpresses a folding modulator selected from LepB, Tig, and DsbAC-Skp. In any of the above embodiments, the host strain expresses the auxotrophic markers pyrF and proC, and has a protease deficiency and/or overexpresses a folding modulator. In embodiments, the host strain expresses any other suitable selection marker known in the art. In any of the above embodiments, an asparaginase, e.g., a native Type I and/or Type II asparaginase, is inactivated in the host strain. In embodiments, the host strain is a Pseudomonadales host cell is: deficient in Lon and HslU/V; deficient in Lon, DegP1, DegP2, Prc, and AprA; deficient in Lon, DegP1, DegP2 S219A, Prc1, and AprA, and overexpresses DsbAC-Skp; deficient in AspG1 and/or AspG2; deficient in AspG1 and/or AspG2, and overexpresses Tig; deficient in AspG1 and/or AspG2, and overexpresses LepB; deficient in AspG1 and/or AspG2, and deficient in Lon and HslU/V; a host cell that is deficient in AspG1 and/or AspG2, and deficient in Lon, DegP1, DegP2, Prc, and AprA; or a host cell that is deficient in AspG1 and/or AspG2, Lon, DegP1, DegP2, Prc1, and AprA, and overexpresses DsbAC-Skp.

These and other proteases and folding modulators are known in the art and described in the literature, e.g., in U.S. Pat. No. 8,603,824. For example, Table D of the patent describes Tig (tig, Trigger factor, FKBP type ppiase (ec 5.2.1.8) RXF04655, UniProtKB—P0A850 (TIG_ECOLI)). WO 2008/134461 and U.S. Pat. No. 9,394,571, titled "Method for Rapidly Screening Microbial Hosts to Identify Certain Strains with Improved Yield and/or Quality in the Expression of Heterologous Proteins," and incorporated by reference in its entirety herein, describe Tig (RXF04655.2, SEQ ID NO: 34 therein), LepB (RXF01181.1, SEQ ID NO: 56 therein), DegP1 (RXF01250, SEQ ID NO: 57 therein), AprA (RXF04304.1, SEQ ID NO: 86 therein), Prc1 (RXF06586.1, SEQ ID NO: 120 therein), DegP2, (RXF07210.1, SEQ ID NO: 124 therein), Lon (RXF04653, SEQ ID NO: 92 therein); DsbA (RXF01002.1, SEQ ID NO: 25 therein), and DsbC (RXF03307.1, SEQ ID NO: 26 therein). These sequences and those for other proteases and folding modulators also are set forth in U.S. Pat. No. 9,580,719 (Table of SEQ ID NOS in columns 93-98 therein). For example, U.S. Pat. No. 9,580,719 provides the sequence encoding HslU (RXF01957.2) and HslV (RXF01961.2) as SEQ ID NOS 18 and 19, respectively.

Codon Optimization

In one embodiment, the methods herein comprise expression of recombinant crisantaspase from a construct that has been optimized for codon usage in a strain of interest. In embodiments, the strain is a *Pseudomonas* host cell, e.g., *Pseudomonas fluorescens*. Methods for optimizing codons to improve expression in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. Methods for optimizing the nucleic acid sequence of to improve expression of a heterologous protein in a bacterial host are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Optimization addresses any of a number of sequence features of the heterologous gene. As a specific example, a rare codon-induced translational pause often results in reduced heterologous protein expression. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which sometimes results in rare host codons being removed from the synthetic polynucleotide sequence.

Alternate translational initiation also sometimes results in reduced heterologous protein expression. Alternate translational initiation include a synthetic polynucleotide sequence inadvertently containing motifs capable of functioning as a ribosome binding site (RBS). These sites, in some cases, result in initiating translation of a truncated protein from a gene-internal site. One method of reducing the possibility of producing a truncated protein, which are often difficult to remove during purification, includes eliminating putative internal RBS sequences from an optimized polynucleotide sequence.

Repeat-induced polymerase slippage often results in reduced heterologous protein expression. Repeat-induced polymerase slippage involves nucleotide sequence repeats that have been shown to cause slippage or stuttering of DNA polymerase which sometimes results in frameshift mutations. Such repeats also often cause slippage of RNA polymerase. In an organism with a high G+C content bias, there is sometimes a higher degree of repeats composed of G or C nucleotide repeats. Therefore, one method of reducing the possibility of inducing RNA polymerase slippage, includes altering extended repeats of G or C nucleotides.

Interfering secondary structures also sometimes result in reduced heterologous protein expression. Secondary structures often sequester the RBS sequence or initiation codon and have been correlated to a reduction in protein expression. Stem loop structures are also often involved in transcriptional pausing and attenuation. An optimized polynucleotide sequence usually contains minimal secondary structures in the RBS and gene coding regions of the nucleotide sequence to allow for improved transcription and translation.

Another feature that sometimes effect heterologous protein expression is the presence of restriction sites. By removing restriction sites that could interfere with subsequent sub-cloning of transcription units into host expression vectors a polynucleotide sequence is optimized.

For example, the optimization process often begins by identifying the desired amino acid sequence to be heterologously expressed by the host. From the amino acid sequence a candidate polynucleotide or DNA is designed. During the design of the synthetic DNA sequence, the frequency of codon usage is often compared to the codon usage of the host expression organism and rare host codons are removed from the synthetic sequence. Additionally, the synthetic candidate DNA sequence is sometimes modified in order to remove undesirable enzyme restriction sites and add or remove any desired signal sequences, linkers or untranslated regions. The synthetic DNA sequence is often analyzed for the presence of secondary structure that may interfere with the translation process, such as G/C repeats and stem-loop structures. Before the candidate DNA sequence is synthesized, the optimized sequence design is often be checked to verify that the sequence correctly encodes the desired amino acid sequence. Finally, the candidate DNA sequence is synthesized using DNA synthesis techniques, such as those known in the art.

In another embodiment herein, the general codon usage in a host organism, such as *P. fluorescens*, is often utilized to optimize the expression of the heterologous polynucleotide sequence. The percentage and distribution of codons that rarely would be considered as preferred for a particular amino acid in the host expression system is evaluated. Values of 5% and 10% usage is often used as cutoff values for the determination of rare codons. For example, the codons listed in Table 4 have a calculated occurrence of less than 5% in the *P. fluorescens* MB214 genome and would be generally avoided in an optimized gene expressed in a *P. fluorescens* host.

TABLE 4.

Codons occurring at less than 5% in *P. fluorescens* MB214

| Amino Acid(s) | Codon(s) Used | % Occurrence |
|---|---|---|
| G Gly | GGA | 3.26 |
| I Ile | ATA | 3.05 |
| L Leu | CTA | 1.78 |
| | CTT | 4.57 |
| | TTA | 1.89 |
| R Arg | AGA | 1.39 |
| | AGG | 2.72 |
| | CGA | 4.99 |
| S Ser | TCT | 4.28 |

The present disclosure contemplates the use of any crisantaspase coding sequence, including any sequence that has been optimized for expression in the *Pseudomonas* host cell being used. Sequences contemplated for use are often optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods provided herein is encoded by any appropriate nucleic acid sequence. Codon optimization for expression in *E. coli* is described, e.g., by Welch, et al., 2009, PLoS One, "Design Parameters to Control Synthetic Gene Expression in *Escherichia coli,*" 4(9): e7002, Ghane, et al., 2008, Krishna R. et al., (2008) Mol Biotechnology "Optimization of the AT-content of Codons Immediately Downstream of the Initiation Codon and Evaluation of Culture Conditions for High-level Expression of Recombinant Human G-CSF in *Escherichia coli,*" 38:221-232.

High Throughput Screens

In some embodiments, a high throughput screen is often conducted to determine optimal conditions for expressing soluble recombinant crisantaspase. The conditions that be varied in the screen include, for example, the host cell, genetic background of the host cell (e.g., deletions of different proteases), type of promoter in an expression construct, type of secretion leader fused to encoded crisantaspase, temperature of growth, OD of induction when an inducible promoter is used, amount of inducer added (e.g. amount of IPTG used for induction when a lacZ promoter or derivative thereof is used), duration of protein induction, temperature of growth following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" is often identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, whether the protein is sequestered (e.g., in inclusion bodies) or secreted, protein folding, and the like. For example, the optimal host strain or optimal expression system produces a yield, characterized by the amount of soluble heterologous protein, the amount of recoverable heterologous protein, the amount of properly processed heterologous protein, the amount of properly folded heterologous protein, the amount of active heterologous protein, and/or the total amount of heterologous protein, of a certain absolute level or a certain level relative to that produced by an indicator strain, i.e., a strain used for comparison.

Methods of screening microbial hosts to identify strains with improved yield and/or quality in the expression of heterologous proteins are described, for example, in U.S. Patent Application Publication No. 20080269070.

Bacterial Growth Conditions

Growth conditions useful in the methods herein often comprise a temperature of about 4° C. to about 42° C. and a pH of about 5.7 to about 8.8. When an expression construct with a lacZ promoter or derivative thereof is used, expression is often induced by adding IPTG to a culture at a final concentration of about 0.01 mM to about 1.0 mM.

The pH of the culture is sometimes maintained using pH buffers and methods known to those of skill in the art. Control of pH during culturing also is often achieved using aqueous ammonia. In embodiments, the pH of the culture is about 5.7 to about 8.8. In certain embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8 In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8. In yet other embodiments, the pH is about 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25. In some embodiments, the pH is about 5.0 to about 8.0.

In embodiments, the growth temperature is maintained at about 4° C. to about 42° C. In certain embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 30° C. to about 33° C., or about 32° C. to about 33° C. In embodiments, the growth temperature is maintained at about 22° C. to about 33° C. In other embodiments, the temperature is changed during culturing. In certain embodiments, the temperature is maintained at about 30° C. to about 32° C. before an agent to induce expression from the construct encoding the polypeptide or protein of interest is added to the culture, and the temperature is dropped to about 25° C. to about 27° C. after adding an agent to induce expression, e.g., IPTG is added to the culture. In one embodiment, the temperature is maintained at about 30° C. before an agent to induce expression from the construct encoding the polypeptide or protein of interest is added to the culture, and the temperature is dropped to about 25° C. after adding an agent to induce expression is added to the culture.

Induction

As described elsewhere herein, inducible promoters are often used in the expression construct to control expression of the recombinant crisantaspase, e.g., a lac promoter. In the case of the lac promoter derivatives or family members, e.g., the tac promoter, the effector compound is an inducer, such as a gratuitous inducer like IPTG (isopropyl-β-D-1-thiogalactopyranoside, also called "isopropylthiogalactoside"). In embodiments, a lac promoter derivative is used, and crisantaspase expression is induced by the addition of IPTG to a final concentration of about 0.01 mM to about 1.0 mM, when the cell density has reached a level identified by an OD575 of about 25 to about 160. In embodiments, the OD575 at the time of culture induction for crisantaspase is about 25, about 50, about 55, about 60, about 65, about 70, about 80, about 90, about 100, about 110, about 120, about 130, about 140, about 150, about 160, about 170 about 180. In other embodiments, the OD575 is about 80 to about 100, about 100 to about 120, about 120 to about 140, about 140 to about 160. In other embodiments, the OD575 is about 80 to about 120, about 100 to about 140, or about 120 to about 160. In other embodiments, the OD575 is about 80 to about 140, or about 100 to 160. The cell density is often measured by other methods and expressed in other units, e.g., in cells per unit volume. For example, an OD575 of about 25 to about 160 of a *Pseudomonas fluorescens* culture is equivalent to approximately $2.5\times10^{10}$ to about $1.6\times10^{11}$ colony forming units per mL or 11 to 70 g/L dry cell weight, or about 0.05 g/g to about 0.4 g/g wet cell weight. In embodiments, a measurement of cell density of OD575 is converted to a measurement of CFU with a conversion of an OD575 of 1 equal to $1\times10^{9}$; is converted to a measurement of wet cell weight with a conversion of OD575 of 1 equal to 0.002 g/g; is converted to a measurement of dry cell weight with a conversion of OD575 of 1 equal to 0.44 g/L. In embodiments, crisantaspase expression is induced by the addition of IPTG to a final concentration of about 0.01 mM to about 1.0 mM, when the cell density has reached a wet weight of about 0.05 g/g to about 0.4 g/g. In embodiments the wet cell weight is about 0.05 g/g, about 0.1 g/g, about 0.15 g/g, about 0.2 g/g, about 0.25 g/g, about 0.30 g/g, about 0.35 g/g, about 0.40 g/g, about 0.05 g/g to about 0.1 g/g, about 0.05 g/g to about 0.15 g/g, about 0.05 g/g to about 0.20 g/g, about 0.05 g/g to about 0.25 g/g, about 0.05 g/g to about 0.30 g/g, about 0.05 g/g to about 0.35 g/g, about 0.1 g/g to about 0.40 g/g, about 0.15 g/g to about 0.40 g/g, about 0.20 g/g to about 0.40 g/g, about 0.25 g/g to about 0.40 g/g, about 0.30 g/g to about 0.40 g/g, or about 0.35 g/g to about 0.40 g/g. In embodiments, the wet cell weight is about 0.1 g/g to about 0.5 g/g. In embodiments, the cell density at the time of culture induction is equivalent to the cell density as specified herein by the absorbance at OD575, regardless of the method used for determining cell density or the units of measurement. One of skill in the art will know how to make the appropriate conversion for any cell culture.

In embodiments, the final IPTG concentration of the culture is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, or about 1 mM. In other embodiments, the final IPTG concentration of the culture is about 0.08 mM to about 0.1 mM, about 0.1 mM to about 0.2 mM, about 0.2 mM to about 0.3 mM, about 0.3 mM to about 0.4 mM, about 0.2 mM to about 0.4 mM, about 0.08 to about 0.2 mM, or about 0.1 to 1 mM. In embodiments, IPTG is at a concentration in the culture medium of about 0.05 mM to about 2.5 mM.

In embodiments wherein a non-lac type promoter is used, as described herein and in the literature, other inducers or effectors are often used. In one embodiment, the promoter is a constitutive promoter.

After adding an inducing agent, cultures are often grown for a period of time, for example about 24 hours, during which time the recombinant crisantaspase is expressed. After adding an inducing agent, a culture is often grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture is grown for about 1 to 48 hrs, about 1 to 24 hrs, about 10 to 24 hrs, about 15 to 24 hrs, or about 20 to 24 hrs. Cell cultures are often concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Microfluidizer, Constant Cell Disruptor, Niro-Soavi homogenizer or APV-Gaulin homogenizer). Cells expressing crisantaspase are often disrupted, for example, using sonication. Any appropriate method known in the art for lysing cells are often used to release the soluble fraction. For example, in embodiments, chemical and/or enzymatic cell lysis reagents, such as cell-wall lytic enzyme and EDTA, are often used. Use of frozen or previously stored cultures is also contemplated in the methods herein. Cultures are sometimes OD-normalized prior to lysis. For example, cells are often normalized to an OD600 of about 10, about 11, about 12, about 13, about 14, about 15, about 16, about 17, about 18, about 19, or about 20.

Centrifugation is performed using any appropriate equipment and method. Centrifugation of cell culture or lysate for the purposes of separating a soluble fraction from an insoluble fraction is well-known in the art. For example, lysed cells are sometimes centrifuged at 20,800×g for 20 minutes (at 4° C.), and the supernatants removed using manual or automated liquid handling. The pellet (insoluble) fraction is resuspended in a buffered solution, e.g., phosphate buffered saline (PBS), pH 7.4. Resuspension is often carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures.

Fermentation Format

In one embodiment, fermentation is used in the methods of producing recombinant crisantaspase. The expression system according to the present disclosure is cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media often contains mineral salts and a carbon source, but is often supplemented with, e.g., low levels of amino acids, vitamins, peptones, or other ingredients, though these are added at very minimal levels. Media is often prepared using the methods described in the art, e.g., in U.S. Pat. App. Pub. No. 2006/0040352, referenced and incorporated by reference above. Details of cultivation procedures and mineral salts media useful in the methods herein are described by Riesenberg, D et al., 1991, "High cell density cultivation of *Escherichia coli* at controlled specific growth rate," J. Biotechnol. 20 (1):17-27.

Fermentation may be performed at any scale. The expression systems according to the present disclosure are useful for recombinant protein expression at any scale. Thus, e.g., microliter-scale, milliliter scale, centiliter scale, and deciliter scale fermentation volumes may be used, and 1 Liter scale and larger fermentation volumes are often used.

In embodiments, the fermentation volume is at or above about 1 Liter. In embodiments, the fermentation volume is about 0.5 liters to about 100 liters. In embodiments, the fermentation volume is about 0.5 liters, about 1 liter, about 2 liters, about 3 liters, about 4 liters, about 5 liters, about 6 liters, about 7 liters, about 8 liters, about 9 liters, or about 10 liters. In embodiments, the fermentation volume is about 0.5 liters to about 2 liters, about 0.5 liters to about 5 liters, about 0.5 liters to about 10 liters, about 0.5 liters to about 25 liters, about 0.5 liters to about 50 liters, about 0.5 liters to about 75 liters, about 10 liters to about 25 liters, about 25 liters to about 50 liters, or about 50 liters to about 100 liters. In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

Protein Analysis

In embodiments, recombinant crisantaspase protein produced by the methods of the provided herein is analyzed. Recombinant crisantaspase is sometimes analyzed, for example, by biolayer interferometry, SDS-PAGE, Western blot, Far Western blot, ELISA, absorbance, or mass spectrometry (e.g., tandem mass spectrometry).

In some embodiments, the concentration and/or amounts of recombinant crisantaspase protein generated are determined, for example, by Bradford assay, absorbance, Coomassie staining, mass spectrometry, etc.

Protein yield in the insoluble and soluble fractions as described herein are often determined by methods known to those of skill in the art, for example, by capillary gel electrophoresis (CGE), and Western blot analysis. Soluble fractions are often evaluated, for example, using biolayer interferometry.

The asparaginase monomer is capable of forming active tetramer, e.g., in cell lysate, cell sonicate, and upon further purification. Following expression of the recombinant asparaginase in a bacterial expression system, e.g., in a *E. coli* or *Pseudomonas* host strain, the recombinant protein can be purified using any suitable method known in the art, e.g., to remove host cell proteins. Purification methods can include, e.g., cation exchange chromatography, anion exchange chromatography, size exclusion chromatography, high performance liquid chromatography (HPLC), or a combination of these and/or other known methods. Asparaginase protein purification is described in the literature, e.g., in U.S. Pat. No. 5,310,670, “Method for the purification of *Erwinia* L-asparaginase,” and U.S. Pat. No. 8,323,948, “Asparaginases and uses thereof,” each incorporated by reference herein in its entirety. Based on our expression experiments, a type II asparaginase expressed in *P. fluorescens* is present as active, tetrameric asparaginase enzyme in sonicates.

In embodiments, a measurable characteristic (e.g., activity, size, length, or other characteristic indicative of active and/or intact protein) of an amount of an unpurified or purified asparaginase sample is compared with the same measurable characteristic of the same amount of an asparaginase standard sample (e.g., a commercially obtained asparaginase). It is understood that the amount of asparaginase protein in a sample can be determined by any suitable assay known in the art for protein measurement, and the activity by any suitable assay, e.g., as described herein.

Useful measures of protein yield include, e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of soluble recombinant protein, percent or fraction of active protein (e.g., amount of active protein/amount protein used in the assay), percent or fraction of total cell protein (tcp), amount of protein/cell, and percent dry biomass.

In embodiments, the methods herein are used to obtain a yield of soluble recombinant crisantaspase protein, e.g., monomer or tetramer, of about 20% to about 90% total cell protein. In certain embodiments, the yield of soluble recombinant crisantaspase is about 20% total cell protein, about 25% total cell protein, about 30% total cell protein, about 31% total cell protein, about 32% total cell protein, about 33% total cell protein, about 34% total cell protein, about 35% total cell protein, about 36% total cell protein, about 37% total cell protein, about 38% total cell protein, about 39% total cell protein, about 40% total cell protein, about 41% total cell protein, about 42% total cell protein, about 43% total cell protein, about 44% total cell protein, about 45% total cell protein, about 46% total cell protein, about 47% total cell protein, about 48% total cell protein, about 49% total cell protein, about 50% total cell protein, about 51% total cell protein, about 52% total cell protein, about 53% total cell protein, about 54% total cell protein, about 55% total cell protein, about 56% total cell protein, about 57% total cell protein, about 58% total cell protein, about 59% total cell protein, about 60% total cell protein, about 65% total cell protein, about 70% total cell protein, about 75% total cell protein, about 80% total cell protein, about 85% total cell protein, or about 90% total cell protein. In some embodiments, the yield of soluble recombinant crisantaspase is about 20% to about 25% total cell protein, about 20% to about 30% total cell protein, about 20% to about 35% total cell protein, about 20% to about 40% total cell protein, about 20% to about 45% total cell protein, about 20% to about 50% total cell protein, about 20% to about 55% total cell protein, about 20% to about 60% total cell protein, about 20% to about 65% total cell protein, about 20% to about 70% total cell protein, about 20% to about 75% total cell protein, about 20% to about 80% total cell protein, about 20% to about 85% total cell protein, about 20% to about 90% total cell protein, about 25% to about 90% total cell protein, about 30% to about 90% total cell protein, about 35% to about 90% total cell protein, about 40% to about 90% total cell protein, about 45% to about 90% total cell protein, about 50% to about 90% total cell protein, about 55% to about 90% total cell protein, about 60% to about 90% total cell protein, about 65% to about 90% total cell protein, about 70% to about 90% total cell protein, about 75% to about 90% total cell protein, about 80% to about 90% total cell protein, about 85% to about 90% total cell protein, about 20% to about 40% total cell protein, about 25% to about 40% total cell protein, about 35% to about 40% total cell protein, about 20% to about 35% total cell protein, about 20% to about 30% total cell protein, or about 20% to about 25% total cell protein. In some embodiments, the yield of soluble recombinant crisantaspase is about 20% to about 40% total cell protein.

In embodiments, the methods herein are used to obtain a yield of soluble recombinant crisantaspase protein, e.g., monomer or tetramer, of about 1 gram per liter to about 50 grams per liter. In certain embodiments, the yield of soluble recombinant crisantaspase is about 1 gram per liter, about 2 grams per liter, about 3 grams per liter, about 4 grams per liter, about 5 grams per liter, about 6 grams per liter, about 7 grams per liter, about 8 grams per liter, about 9 grams per liter, about 10 gram per liter, about 11 grams per liter, about 12 grams per liter, about 13 grams per liter, about 14 grams per liter, about 15 grams per liter, about 16 grams per liter, about 17 grams per liter, about 18 grams per liter, about 19 grams per liter, about 20 grams per liter, about 21 grams per liter, about 22 grams per liter, about 23 grams per liter about 24 grams per liter, about 25 grams per liter, about 26 grams per liter, about 27 grams per liter, about 28 grams per liter, about 30 grams per liter, about 35 grams per liter, about 40 grams per liter, about 45 grams per liter about 50 grams per liter about 1 gram per liter to about 5 grams per liter, about 1 gram to about 10 grams per liter, about 10 gram per liter to about 12 grams per liter, about 10 grams per liter to about 13 grams per liter, about 10 grams per liter to about 14 grams per liter, about 10 grams per liter to about 15 grams per liter, about 10 grams per liter to about 16 grams per liter, about 10 grams per liter to about 17 grams per liter, about 10 grams per liter to about 18 grams per liter, about 10 grams per liter to about 19 grams per liter, about 10 grams per liter to about 20 grams per liter, about 10 grams per liter to about 21 grams per liter, about 10 grams per liter to about 22 grams per liter, about 10 grams per liter to about 23 grams per liter, about 10 grams per liter to about 24 grams per liter, about 10 grams per liter to about 25 grams per liter, about 10 grams per liter to about 30 grams per liter, about 10 grams per liter to about 40 grams per liter, about 10 grams per liter to about 50 grams per liter, about 10 gram per liter to about 12 grams per liter, about 12 grams per liter to about 14 grams per liter, about 14 grams per liter to about 16 grams per liter, about 16 grams per liter to about 18 grams per liter, about 18 grams per liter to about 20 grams per liter, about 20 grams per liter to about 22 grams per liter, about 22 grams per liter to about 24 grams per liter, about 23 grams per liter to about 25 grams per liter, about 10 grams per liter to about 25 grams per liter, about 11 grams per liter to about 25 grams per liter, about 12 grams per liter to about 25 grams per liter, about 13 grams per liter to about 25 grams per liter, about 14 grams per liter to about 25 grams per liter, about 15 grams per liter to about 25 grams per liter, about 16 grams per liter to about 25 grams per liter, about 17 grams per liter to about 25 grams per liter, about 18 grams per liter to about 25 grams per liter, about 19 grams per liter to about 25 grams per liter, about 20 grams per liter to about 25 grams per liter, about 21 grams per liter to about 25 grams per liter, about 22 grams per liter to about 25 grams per liter, about 23 grams per liter to about 25 grams per liter, or about 24 grams per liter to about 25 grams per liter. In embodiments, the soluble recombinant protein yield is about 10 gram per liter to about 13 grams per liter, about 12 grams per liter to about 14 grams per liter, about 13 grams per liter to about 15 grams per liter, about 14 grams per liter to about 16 grams per liter, about 15 grams per liter to about 17 grams per liter, about 16 grams per liter to about 18 grams per liter, about 17 grams per liter to about 19 grams per liter, about 18 grams per liter to about 20 grams per liter, about 20 grams per liter to about 22 grams per liter, about 22 grams per liter to about 24 grams per liter, or about 23 grams per liter to about 25 grams per liter. In embodiments, the soluble recombinant protein yield is about 10 grams per liter to about 25 grams per liter, about 12 gram per liter to about 24 grams per liter, about 14 grams per liter to about 22 grams per liter, about 16 grams per liter to about 20 grams per liter, or about 18 grams per liter to about 20 grams per liter. In embodiments, the extracted protein yield is about 5 grams per liter to about 15 grams per liter, about 5 gram per liter to about 25 grams per liter, about 10 grams per liter to about 15 grams per liter, about 10 grams per liter to about 25 grams per liter, about 15 grams per liter to about 20 grams per liter, about 15 grams per liter to about 25 grams per liter, or about 18 grams per liter to about 25 grams per liter. In certain embodiments, the yield of soluble recombinant crisantaspase is about 10 grams per liter to about 25 grams per liter.

In embodiments, the amount of recombinant crisantaspase, e.g., monomer or tetramer, detected in the soluble fraction is about 10% to about 100% of the amount of the total recombinant crisantaspase produced. In embodiments, this amount is about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%, or about 100% of the amount of the total recombinant crisantaspase produced. In embodiments, this amount is about 10% to about 20%, 20% to about 50%, about 25% to about 50%, about 25% to about 50%, about 25% to about 95%, about 30% to about 50%, about 30% to about 40%, about 30% to about 60%, about 30% to about 70%, about 35% to about 50%, about 35% to about 70%, about 35% to about 75%, about 35% to about 95%, about 40% to about 50%, about 40% to about 95%, about 50% to about 75%, about 50% to about 95%, about 70% to about 95%, or about 80 to about 100% of the amount of the total recombinant crisantaspase produced.

In some embodiments, the amount of soluble recombinant asparaginase is expressed as a percentage of the total soluble protein produced in a culture. Data expressed in terms of recombinant asparaginase protein weight/volume of cell culture at a given cell density can be converted to data expressed as percent recombinant protein of total cell protein. It is within the capabilities of a skilled artisan to convert volumetric protein yield to % total cell protein, for example, knowing the amount of total cell protein per volume of cell culture at the given cell density. This number can be determined if one knows 1) the cell weight/volume of culture at the given cell density, and 2) the percent of cell weight comprised by total protein. For example, at an OD550 of 1.0, the dry cell weight of *E. coli* is reported to be 0.5 grams/liter ("Production of Heterologous Proteins from Recombinant DNA *Escherichia coli* in Bench Fermentors," Lin, N. S., and Swartz, J. R., 1992, METHODS: A Companion to Methods in Enzymology 4: 159-168). A bacterial cell is comprised of polysaccharides, lipids, and nucleic acids, as well as proteins. An *E. coli* cell is reported to be about 52.4 to 55% protein by references including, but not limited to, Da Silva, N. A., et al., 1986, "Theoretical Growth Yield Estimates for Recombinant Cells," Biotechnology and Bioengineering, Vol. XXVIII: 741-746, estimating protein to make up 52.4% by weight of *E. coli* cells, and "*Escherichia coli* and *Salmonella typhimurium* Cellular and Molecular Biology," 1987, Ed. in Chief Frederick C. Neidhardt, Vol. 1, pp. 3-6, reporting protein content in *E. coli* as 55% dry cell weight. Using the measurements above (i.e., a dry cell weight of 0.5 grams/liter, and protein as 55% cell weight), the amount of total cell protein per volume of cell culture at an A550 of 1.0 for *E. coli* is calculated as 275 μg total cell protein/ml/A550. A calculation of total cell protein per volume of cell culture based on wet cell weight can use, e.g., the determination by Glazyrina, et al. (Microbial Cell Factories 2010, 9:42, incorporated herein by reference) that an A600 of 1.0 for *E. coli* resulted in a wet cell weight of 1.7 grams/liter and a dry cell weight of 0.39 grams/liter. For example, using this wet cell weight to dry cell weight comparison, and protein as 55% dry cell weight as described above, the amount of total cell protein per volume of cell culture at an A600 of 1.0 for *E. coli* can be calculated as 215 μg total cell protein/ml/A600. For *Pseudomonas fluorescens*, the amount of total cell protein per volume of cell culture at a given cell density is similar to that found for *E. coli. P. fluorescens*, like *E. coli*, is a gram-negative, rod-shaped bacterium. The dry cell weight of *P. fluorescens* ATCC 11150 as reported by Edwards, et al., 1972, "Continuous Culture of *Pseudomonas fluorescens* with Sodium Maleate as a Carbon Source," Biotechnology and Bioengineering, Vol. XIV, pages 123-147, is 0.5 grams/liter/A500. This is the same weight reported by Lin, et al., for *E. coli* at an A550 of 1.0. Light scattering measurements made at 500 nm and at 550 nm are expected to be very similar. The percent of cell weight comprised by total cell protein for *P. fluorescens* HK44 is described as 55% by, e.g., Yarwood, et al., July 2002, "Noninvasive Quantitative Measurement of Bacterial Growth in Porous Media under Unsaturated-Flow Conditions," Applied and Environmental Microbiology 68(7): 3597-3605. This percentage is similar to or the same as those given for *E. coli* by the references described above.

In embodiments, the amount of soluble recombinant crisantaspase, e.g., monomer or tetramer, produced is about 0.1% to about 95% of the total soluble protein produced in a culture. In embodiments, this amount is more than about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total soluble protein produced in a culture. In embodiments, this amount is about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total soluble protein produced in a culture. In embodiments, this amount is about 5% to about 95%, about 10% to about 85%, about 20% to about 75%, about 30% to about 65%, about 40% to about 55%, about 1% to about 95%, about 5% to about 30%, about 1% to about 10%, about 10% to about 20%, about 20% to about 30%, about 30% to about 40%, about 40% to about 50%, about 50 to about 60%, about 60% to about 70%, or about 80% to about 90% of the total soluble protein produced in a culture.

In embodiments, the amount of soluble recombinant crisantaspase, e.g., monomer or tetramer, produced is about 0.1% to about 50% of the dry cell weight (DCW). In embodiments, this amount is more than about 0.1%, 0.5%, 1%, 5%, 10%, 15%, 20%, 25%, 30%, 40%, 45%, or 50% of DCW. In embodiments, this amount is about 0.1%, 0.5%, 1%, 5%, 10%, 15%, 20%, 25%, 30%, 40%, 45%, or 50% of DCW. In embodiments, this amount is about 5% to about 50%, about 10% to about 40%, about 20% to about 30%, about 1% to about 20%, about 5% to about 25%, about 1% to about 10%, about 10% to about 20%, about 20% to about 30%, about 30% to about 40%, or about 40% to about 50% of the total soluble protein produced in a culture.

In embodiments, the yield or amount of cytoplasmically produced soluble recombinant crisantaspase, as described in terms of any of these protein measures (e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of soluble recombinant protein, percent or fraction of active protein (e.g., amount of active protein/amount protein used in the assay), percent or fraction of total cell protein (tcp), amount of protein/cell, and percent dry biomass), is equivalent to or increased relative to the amount of periplasmically produced soluble recombinant crisantaspase obtained under similar or substantially similar conditions (conditions include, e.g., the host cell, genetic background of the host cell (e.g., deletions of different proteases), type of promoter in an expression construct, temperature of growth, OD of induction when an inducible promoter is used, amount of inducer added (e.g. amount of IPTG used for induction when a lacZ promoter or derivative thereof is used), duration of protein induction, temperature of growth following addition of an inducing agent to a culture, rate of agitation of culture, method of selection for plasmid maintenance, volume of culture in a vessel, and method of cell lysing). In embodiments, the yield ratio of cytoplasmically produced soluble recombinant crisantaspase to periplasmically produced soluble recombinant crisantaspase obtained under similar or substantially similar conditions is about 1:1 (i.e., 1) to about 5:1 (i.e., 5). In embodiments, the yield ratio of cytoplasmically produced soluble recombinant crisantaspase to periplasmically produced soluble recombinant crisantaspase obtained under similar or substantially similar conditions is about 1 to about 5. In embodiments, the yield ratio of cytoplasmically produced soluble recombinant crisantaspase to periplasmically produced soluble recombinant crisantaspase obtained under similar or substantially similar conditions is at least about 1. In embodiments, the yield ratio of cytoplasmically produced soluble recombinant crisantaspase to periplasmically produced soluble recombinant crisantaspase obtained under similar or substantially similar conditions is at most about 5. In embodiments, the yield ratio of cytoplasmically produced soluble recombinant crisantaspase to periplasmically produced soluble recombinant crisantaspase obtained under similar or substantially similar conditions is about 1 to about 1.25, about 1 to about 1.5, about 1 to about 1.75, about 1 to about 2, about 1 to about 2.5, about 1 to about 3, about 1 to about 3.5, about 1 to about 4, about 1 to about 4.5, about 1 to about 5, about 1.25 to about 1.5, about 1.25 to about 1.75, about 1.25 to about 2, about 1.25 to about 2.5, about 1.25 to about 3, about 1.25 to about 3.5, about 1.25 to about 4, about 1.25 to about 4.5, about 1.25 to about 5, about 1.5 to about 1.75, about 1.5 to about 2, about 1.5 to about 2.5, about 1.5 to about 3, about 1.5 to about 3.5, about 1.5 to about 4, about 1.5 to about 4.5, about 1.5 to about 5, about 1.75 to about 2, about 1.75 to about 2.5, about 1.75 to about 3, about 1.75 to about 3.5, about 1.75 to about 4, about 1.75 to about 4.5, about 1.75 to about 5, about 2 to about 2.5, about 2 to about 3, about 2 to about 3.5, about 2 to about 4, about 2 to about 4.5, about 2 to about 5, about 2.5 to about 3, about 2.5 to about 3.5, about 2.5 to about 4, about 2.5 to about 4.5, about 2.5 to about 5, about 3 to about 3.5, about 3 to about 4, about 3 to about 4.5, about 3 to about 5, about 3.5 to about 4, about 3.5 to about 4.5, about 3.5 to about 5, about 4 to about 4.5, about 4 to about 5, or about 4.5 to about 5. In embodiments, the yield ratio of cytoplasmically produced soluble recombinant crisantaspase to periplasmically produced soluble recombinant crisantaspase obtained under similar or substantially similar conditions is about 1, about 1.25, about 1.5, about 1.75, about 2, about 2.5, about 3, about 3.5, about 4, about 4.5, or about 5.

Solubility and Activity

The "solubility" and "activity" of a protein, though related qualities, are generally determined by different means. Solubility of a protein, particularly a hydrophobic protein, indicates that hydrophobic amino acid residues are improperly located on the outside of the folded protein. Protein activity, which is often evaluated using different methods, e.g., as described below, is another indicator of proper protein conformation. "Soluble, active, or both" as used herein, refers to protein that is determined to be soluble, active, or both soluble and active, by methods known to those of skill in the art.

Activity Assay

Assays for evaluating crisantaspase activity are known in the art and include but are not limited to fluorometric, colorometric, chemiluminescent, spectrophotometric, and other enzyme assays available to one of skill in the art. These assays can be used to compare activity or potency of a crisantaspase preparation to a commercial or other crisantaspase preparation.

In embodiments, activity or potency is represented by the percent active protein in the extract supernatant as compared with the total amount assayed. This is based on the amount of protein determined to be active by the assay relative to the total amount of protein used in assay. In other embodiments, activity or potency is represented by the % activity or potency level of the protein compared to a standard or control protein. This is based on the amount of active protein in supernatant extract sample relative to the amount of active protein in a standard sample (where the same amount of protein from each sample is used in assay).

In embodiments, the standard or control protein used in the activity or potency assay for comparison to a produced crisantaspase is the active ingredient in Erwinaze®, or the active ingredient in any crisantaspase product approved for clinical use and known in the art. In embodiments, the measured activity or potency of the crisantaspase produced is compared with an activity or potency measured in the same amount of the standard or control crisantaspase using the same method for measuring crisantaspase activity or potency.

In embodiments, methods herein further comprise measuring the activity or potency of an amount of the recombinant crisantaspase protein using an activity or potency assay. In embodiments, about 40% to about 100% of the recombinant crisantaspase protein, is determined to be active, soluble, or both. In embodiments, about 40%, about 50%, about 60%, about 70%, about 80%, about 90%, or about 100% of the recombinant crisantaspase protein is determined to be active, soluble, or both. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the recombinant crisantaspase protein is determined to be active, soluble, or both.

In other embodiments, about 75% to about 100% of the recombinant crisantaspase is determined to be active, soluble, or both. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the recombinant crisantaspase is determined to be active, soluble or both.

In embodiments, a method of producing or expressing a recombinant type II asparaginase as described herein further comprises measuring the activity or potency of the recombinant type II asparaginase produced and comparing the measured activity or potency of the recombinant type II asparaginase produced with an activity or potency measured in the same amount of a control type II asparaginase using the same assay, wherein the measured activity or potency of the recombinant type II asparaginase produced is comparable to the activity or potency of the control type II asparaginase. In embodiments, comparable activity or potency is defined as 100% (which also can be expressed as 1.0), that is, when the activity or potency of the recombinant type II asparaginase produced and the control type II asparaginase are equal. In embodiments, the activity or potency of the recombinant type II asparaginase produced compared to the control type II asparaginase is about 80% to about 120%. In embodiments, the activity or potency is about 85% to about 115%. In embodiments, the activity or potency is about 90% to about 110%. In embodiments, the activity or potency is about 70% to about 130%. In embodiments, the activity or potency is about 65% to about 135%. In embodiments, the activity or potency of the recombinant type II asparaginase produced compared to the control type II asparaginase is about or at least about 65%, about or at least about 66%, about or at least about 67%, about or at least about 68%, about or at least about 69%, about or at least about 70%, about or at least about 71%, about or at least about 72%, about or at least about 73%, about or at least about 74%, about or at least about 75%, about or at least about 75%, about or at least about 76%, about or at least about 77%, about or at least about 78%, about or at least about 79%, about or at least about 80%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98%, about or at least about 99%, about or at least about 100%, about or at least about 101%, about or at least about 102%, about or at least about 103%, about or at least about 104%, about or at least about 105%, about or at least about 106%, about or at least about 107%, about or at least about 108%, about or at least about 109%, about or at least about 110%, about or at least about 111%, about or at least about 112%, about or at least about 113%, about or at least about 114%, about or at least about 115%, about or at least about 116%, about or at least about 117%, about or at least about 118%, about or at least about 119%, about or at least about 120%, about or at least about 121%, about or at least about 122%, about or at least about 123%, about or at least about 124%, about or at least about 125%, about or at least about 126%, about or at least about 127%, about or at least about 128%, about or at least about 129%, about or at least about 130%, about or at least about 131%, about or at least about 132%, about or at least about 133%, about or at least about 134%, or about or at least about 135%. In embodiments, the activity or potency of the recombinant type II asparaginase produced compared to the control type II asparaginase is about 68% to about 132%, about 70% to about 130%, about 72% to about 128%, about 75% to about 125%, about 80% to about 120%, about 85% to about 115%, about 65% to about 110%, about 68% to about 110%, about 70% to about 110%, about 72% to about 110%, about 78% to about 110%, about 80% to about 110%, about 90% to about 110%, about 95% to about 105%, about 85% to about 110%, about 90% to about 110%, about 95% to about 110%, about 96% to about 110%, about 97% to about 110%, about 98% to about 110%, about 99% to about 110%, about 100% to about 110%, about 65% to about 105%, about 68% to about 105%, about 70% to about 105%, about 72% to about 105%, about 80% to about 105%, about 85% to about 105%, about 90% to about 105%, about 95% to about 105%, about 96% to about 105%, about 97% to about 105%, about 98% to about 105%, about 99% to about 105%, about 100% to about 105%, about 65% to about 100%, about 68% to about 100%, about 70% to about 100%, about 72% to about 100%, about 75% to about 100%, about 78% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, about 95% to about 99%, about 96% to about 99%, about 97% to about 99%, about 70% to about 135%, about 75% to about 135%, about 80% to about 135%, about 85% to about 135%, about 90% to about 135%, about 75% to about 130%, about 80% to about 130%, about 85% to about 130%, about 90% to about 130%, about 80% to about 125%, about 85% to about 125%, about 90% to about 125%, about 85% to about 120%, about 90% to about 120%, or about 95% to about 120%.

EXAMPLES

The following examples are given for the purpose of illustrating various embodiments of the disclosure and are not meant to limit the present disclosure in any fashion. The present examples, along with the methods described herein are presently representative embodiments, are exemplary, and are not intended as limitations on the scope. Changes therein and other uses which are encompassed within the spirit of the disclosure as defined by the scope of the claims will occur to those skilled in the art.

Example 1: Project Summary

The project was initiated by constructing the expression strains. The gene encoding crisantaspase protein was optimized for expression in *P. fluorescens*, then synthesized and ligated into each of 40 expression vectors to facilitate one cytoplasmic and 39 periplasmic crisantaspase protein expression strategies. The plasmids were transformed into twenty-four *P. fluorescens* host strains (consisting of protease deletion (PD) strains, folding modulator over-expressing (FMO) strains, protease deletion plus folding modulator over-expressing (PD/FMO) strains, and the wild-type (WT) strain), resulting in 240 unique expression strains.

Each strain was grown and induced in duplicate in a 96-well format according to high throughput (HTP) growth and expression protocols. Initial screening of the 240 expression strains at 96-well scale demonstrated that high expression of soluble crisantaspase protein monomer was achieved. Based upon SDS-CGE analysis of samples from the top 15 strains identified in the 96-well screening, estimated titers of soluble crisantaspase monomer ranged from approximately 0.7 to 1.9 g/L when compared to an *E. coli* L-asparaginase (Sigma) standard curve. Shake flask growth samples from selected expression strains were further analyzed to confirm activity (using a commercially available activity assay kit) as well as intact mass (by LC-MS). An expression strain, STR55978, was chosen for fermentation assessment at 2 L scale based on high titers of monomeric crisantaspase protein and no detectable degradation as determined by SDS-CGE analyses.

At the 2 L fermentation scale, the selected STR55978 expression strain was cultivated under eight different induction conditions. Induction variables included wet cell weight, IPTG concentration, pH and temperature at induction. Capture chromatography was performed on lysate samples from selected fermentation pastes and the capture eluates generated were then analyzed using multiple methods to assess protein identity, activity and purity.

Example 2: Materials and Methods

Design of a Synthetic Crisantaspase Gene for Optimal Expression

A DNA coding for the crisantaspase peptide sequence (FIG. 2, SEQ ID NO: 2) was designed to reflect appropriate codon usage for *P. fluorescens*. A DNA region containing a unique restriction enzyme site (SapI or LguI) was added upstream of the crisantaspase coding sequence designed for direct fusion in frame with the secretion leader coding sequence present in the expression vector. A DNA region containing 3 stop codons and a unique restriction enzyme site (SapI) was added downstream of the coding sequence. The synthetic gene, designated pJ201:226734, was produced by DNA2.0 Inc.

Construction of Crisantaspase Protein Expression Plasmids

Standard cloning methods were used in the construction of expression plasmids used for the HTP Tier 1 expression strategy (or plasmid) screen. Plasmid pJ201-226734 containing the optimized crisantaspase protein coding sequence was obtained from DNA2.0. The pJ201-226734 plasmid was digested with restriction enzyme SapI and the 993 bp fragment containing the optimized crisantaspase gene was subcloned into 40 total expression vectors to facilitate one cytoplasmic and 39 periplasmic expression strategies. The periplasmic expression vectors included 37 different periplasmic leaders and two ribosome binding-site (RBS) affinities. Insert and vectors were ligated overnight with T4 DNA ligase (New England Biolabs, M0202S) and electroporated in 96-well format into competent *P. fluorescens* host strains. The resulting plasmids were named p743-001 through p743-040 as described in Table 5. Two additional plasmids, p743-041 and p743-042, were included in the host strain screening. The p743-042 plasmid, like the p743-001 plasmid, was designed for expression of cytoplasmic crisantaspase protein. However, the p743-042 plasmid was constructed later using a PCR-based method to remove an extra alanine codon that is present immediately following the initiator methionine codon in the crisantaspase coding sequence of plasmid p743-001.

TABLE 5

Expression Plasmids

| Plasmid ID | RBS Strength | Secretion Leader | RpC Vector |
|---|---|---|---|
| p743-001 | High | None-extra Ala | pDOW5277-ala |
| p743-002 | High | DsbD | pDOW3949 |
| p743-003 | High | Leader A | pFNX3952 |
| p743-004 | High | DsbA | pDOW5206 |
| p743-005 | Med | DsbA | pDOW5207 |
| p743-006 | High | Azu | pDOW5209 |
| p743-007 | Med | Azu | pDOW5210 |
| p743-008 | High | Lao | pDOW5217 |
| p743-009 | High | Ibp-S31A | pDOW5220 |
| p743-010 | High | TolB | pDOW5223 |
| p743-011 | High | Tpr | pDOW5226 |
| p743-012 | High | Ttg2C | pDOW5232 |
| p743-013 | High | FlgI | pDOW5235 |
| p743-014 | High | CupC2 | pDOW5238 |
| p743-015 | High | CupB2 | pDOW5241 |
| p743-016 | High | Pbp | pDOW5201 |
| p743-017 | High | PbpA20V | pDOW5259 |
| p743-018 | High | DsbC | pDOW5262 |
| p743-019 | High | Leader B | pFNX3941 |
| p743-020 | High | Leader C | pFNX3942 |
| p743-021 | High | Leader D | pFNX3943 |
| p743-022 | High | Leader E | pFNX3944 |
| p743-023 | High | Leader F | pFNX3947 |
| p743-024 | High | Leader G | pFNX3948 |
| p743-025 | High | Leader H | pFNX3950 |
| p743-026 | High | PorE | pDOW5256 |
| p743-027 | High | Leader I | pFNX3959 |
| p743-028 | High | Leader J | pFNX3957 |
| p743-029 | High | Leader K | pFNX3958 |
| p743-030 | High | Leader L | pFNX4202 |
| p743-031 | High | Leader M | pFNX4203 |
| p743-032 | High | Leader N | pFNX4204 |
| p743-033 | High | Leader O | pFNX4205 |
| p743-034 | High | 5193 | pFNX4206 |
| p743-035 | High | Leader P | pFNX4207 |
| p743-036 | High | Leader Q | pFNX4208 |
| p743-037 | High | Leader R | pFNX4209 |
| p743-038 | High | 8484 | pFNX4210 |
| p743-039 | High | Leader S | pFNX4211 |

TABLE 5-continued

| Expression Plasmids | | | |
|---|---|---|---|
| Plasmid ID | RBS Strength | Secretion Leader | RpC Vector |
| p743-040 | High | Leader T | pFNX4212 |
| p743-041 | High | AnsB | pFNX3968 |
| p743-042 | High | None | pDOW5271 |

Growth and Expression in 96-Well Format

For the expression plasmid screening (HTP Tier 1), ligation mixtures for each of the crisantaspase expression plasmids (Table 5) were transformed into *P. fluorescens* host strains DC454 (PyrF deficient, wild-type for proteases (WT)) and DC441 (pyrF, Lon, and HslUV deficient (PD)) cells. Twenty-five microliters of competent cells were thawed and transferred into a 96-multiwell Nucleovette® plate (Lonza VHNP-1001), and ligation mixture was added to each well. Cells were electroporated using the Nucleofector™ 96-well Shuttle™ system (Lonza AG). Cells were then transferred to 96-well deep well plates with 400 μl M9 salts 1% glucose medium and trace elements (Teknova). The 96-well plates (seed plates) were incubated at 30° C. with shaking for 48 hours. Ten microliters of seed culture were transferred in duplicate into 96-well deep well plates, each well containing 500 μl of HTP medium (Teknova), supplemented with trace elements and 5% glycerol, and incubated as before, for 24 hours. Isopropyl-β-D-1-thiogalactopyranoside (IPTG) was added at the 24-hour time point to each well for a final concentration of 0.3 mM, to induce the expression of target proteins Mannitol (Sigma, M1902) was added to each well for a final concentration of 1% to induce the expression of folding modulators in folding modulator overexpressing strains. Cell density was measured by optical density at 600 nm (OD600) at 24 hours after induction to monitor growth. Twenty-four hours after induction, cells were harvested, diluted 1:3 in 1×PBS for a final volume of 400 μl, then frozen.

For the host strain screening (HTP Tier 2), DNA from 10 HTP Tier 1 selected expression plasmids (Table 6) was transformed into 24 *P. fluorescens* host strains (Table 7) including the wild-type (parent) DC454 (WT) strain, protease deletion (PD) strains, folding modulator overexpressing (FMO) strains and protease deletion plus folding modulator overexpressor (PD/FMO) strains. Folding modulators, when present, were encoded on a second plasmid and expression was driven by a *P. fluorescens*-native mannitol inducible promoter. The 240 host strain screen transformations were performed as follows: twenty-five microliters of *P. fluorescens* host strain competent cells were thawed and transferred into a 96-multi-well Nucleovette® plate, and 10 μl plasmid DNA (10 ng) was added to each well. The cells were electroporated, cultured, induced in HTP format and harvested as described for the plasmid expression screening above.

TABLE 6

| Expression Plasmids Selected for Strain Screening | | |
|---|---|---|
| Plasmid ID | RBS Strength | Secretion Leader |
| p743-042 | High | None |
| p743-009 | High | Ibp-S31A |
| p743-017 | High | Pbp-A20V |
| p743-013 | High | FlgI |
| p743-018 | High | DsbC |

TABLE 6-continued

| Expression Plasmids Selected for Strain Screening | | |
|---|---|---|
| Plasmid ID | RBS Strength | Secretion Leader |
| p743-020 | High | Leader C |
| p743-033 | High | Leader O |
| p743-034 | High | 5193 |
| p743-038 | High | 8484 |
| p743-041 | High | AnsB |

TABLE 7

| Host Strains Used in Strain Screening (WT = Wild Type; PD = protease deletion; FMO = folding modulator overexpressor) | |
|---|---|
| Host Strain ID | Phenotype |
| DC454 | WT |
| DC488 | PD |
| DC489 | PD |
| DC496 | PD |
| DC510 | PD |
| DC1029 | PD |
| DC1084 | PD |
| DC977 | PD |
| DC441 | PD |
| DC549 | FMO |
| PF1201.14 | PD/FMO |
| DC1051 | PD |
| DC1102 | PD/FMO |
| DC1103 | PD/FMO |
| PF1202.11 | PD/FMO |
| PF1345.1 | PD/FMO |
| PF1345.5 | PD/FMO |
| DC1100 | PD/FMO |
| DC1101 | PD/FMO |
| PF1285 | PD |
| PF1332 | PD |
| DC544 | FMO |
| DC974 | FMO |
| DC542 | FMO |

Construction of *P. fluorescens* Asparaginase Deficient Host Strains/Construction of Gene Knock-Out Plasmids A BLAST search of the *P. fluorescens* MB214 genome sequence using the crisantaspase protein amino acid sequence (FIG. 2) as input resulted in output of two protein encoding genes (pegs) showing significant alignment: peg.3886 (L-asparaginase EC 3.5.1.1 type II, SEQ ID NO: 62); E value 5e-85 and peg.5048 (L-asparaginase EC 3.5.1.1, SEQ ID NO: 61); E value 3e-05. A cloned deletion construct for each native L-asparaginase gene was initiated by synthesizing DNA sequence fragments that contain a fusion of upstream and downstream flanking regions for each gene leaving only the start and stop codons of the gene targeted for deletion. Genewiz Inc. (South Plainfield, N.J.) completed synthesis of sequence fragments delPEG3886 (1,107 bp) and delPEG5048 (801 bp) which were subsequently blunt-end ligated into the SrfI site of vector pDOW1261-24 to produce deletion plasmids pFNX3970 and pFNX3969, respectively.

Construction of Native L-Asparaginase-Deficient Host Strains

Chromosomal deletion of each gene was performed sequentially in the selected host strains using the following method: the deletion plasmid was electroporated into a *P. fluorescens* host strain which contains a chromosomal deletion in the pyrF gene involved in uracil (pyrimidine) biosynthesis. The deletion plasmid contains the PyrF coding sequence but is unable to replicate in *P. fluorescens* cells. The electroporated cells were plated onto M9 salts agar plates supplemented with 1% glucose and 250 ug/mL proline (if the host strain is a proline auxotroph). The resulting clones are able to synthesize uracil due to an integration event that recombines the entire deletion plasmid into the chromosome at one of the two homologous regions within the genome. To select for cells that have carried out a second homologous recombination between the integrated plasmid and the chromosome and thereby leave a deletion, plasmid integrant strains were grown to stationary phase in 3 mL LB medium supplemented with 250 ug/mL uracil and 250 ug/mL proline (if the host strain is a proline auxotroph). Cells were then plated on to LB uracil (250 ug/mL) plus 250 ug/mL proline (if the host strain is a proline auxotroph) agar plates that also contained 500 ug/mL 5-fluoroorotic acid (5-FOA) (Zymo Research). Cells that lose the integrated plasmid by recombination also lose the pyrF gene and are therefore expected to be resistant to 5-FOA, which would otherwise be converted into a toxic compound preventing cell growth. Single colonies exhibiting good growth in the presence of 5-FOA (500 ug/mL) were then picked and grown in 3 mL liquid M9 minimal medium containing 1% glucose supplemented with 250 μg/mL uracil and 250 μg/mL proline (if the host strain is a proline auxotroph) to generate culture for storage as glycerol stocks and as template for diagnostic PCR and sequencing reactions.

Confirmation of the Chromosomal Deletion of Native L-Asparaginase Genes

Diagnostic PCR reactions were used to screen for the desired native L-asparginase gene chromosomal deletion utilizing primers annealing to chromosomal regions outside the synthesized gene deletion sequence cloned into the knock-out plasmid. DNA sequencing of the PCR product generated was used to determine that the desired native L-asparaginase gene deletion had occurred as expected without undesired mutations or DNA rearrangements.

Growth and Expression of Crisantaspase Expression Strains in Shake Flasks

Three crisantaspase expression strains and two null strains (*P. fluorescens* wild-type strain DC454 null and *P. fluorescens* native L-asparaginase types 1 and 2 deficient strain PF1433 null) were selected for a shake flask expression scale-up experiment. The null strains harbored expression vectors devoid of the protein crisantaspase coding sequence. PF1433 (PyrF, AspG1, and AspG2 deficient), was constructed by sequential deletion of the aspG2 and aspG1 genes in the host strain DC454 (PyrF deficient).

Each expression strain was inoculated into 2 mL of M9 salts 1% glucose (Teknova). The cultures were incubated at 30° C. with shaking for 24 hours. A 2% inoculum of overnight grown culture for each expression strain was subcultured in 2×200 mL HTP-YE medium supplemented with Trace Elements (Teknova). The flasks were incubated at 30° C. with shaking for 24 hours. Before induction, OD600 of the flasks were recorded by diluting 20 μL into 980 μL of water. Isopropyl-β-D-1 thiogalactopyranoside (IPTG) was added to each flask for a final concentration of 0.3 mM to induce the expression of crisantaspase protein. The flasks were incubated at 30° C. with shaking for 24 hours. For each strain, 2 culture flasks were combined to harvest, and the OD600 of the flasks were recorded. After induction, 400 μL were diluted 1:3 in 1×PBS and then frozen for reduced SDS-CGE and additional analyses. For each strain, ~400 mL of culture was centrifuged (15,900×g for 30 min at 4° C.). The pellet was frozen at ~80° C. after the wet weight was recorded.

2 L Scale Fermentation and Sampling

The inocula for the 2 L scale fermentations (approximately 1 L final fermentation volume) were generated by inoculating a shake flask containing 600 mL of a chemically defined medium supplemented with yeast extract and glycerol with a frozen culture stock of the selected strain. After 16 to 24 h incubation with shaking at 30° C., equal portions of each shake flask culture were then aseptically transferred to each of the 8-unit multiplex fermentation system containing a chemically defined medium designed to support a high biomass. In the 2 L fermentors, cultures were operated under controlled conditions for pH, temperature, and dissolved oxygen in a glycerol fed-batch mode. The fed-batch high cell density fermentation process consisted of a growth phase followed by an induction phase, initiated by the addition of IPTG once the culture reached the target biomass (wet cell weight). The conditions during the induction phase were varied according to the experimental design. The induction phase of the fermentation was allowed to proceed for approximately 24 hours. Analytical samples were withdrawn from the fermentor to determine cell density (optical density at 575 nm) and were then frozen for subsequent analyses to determine the level of target gene expression. At the final time point of 24 hours post-induction, the whole fermentation broth of each vessel was harvested by centrifugation at 15,900×g for 60 to 90 minutes. The cell paste and supernatant were separated and the paste retained and frozen at −80° C.

Sample Preparation

Soluble fractions were prepared by sonication followed by centrifugation. Culture broth samples (400 μL) were sonicated with the Cell Lysis Automated Sonication System (CLASS, Scinomix) with a 24 probe tip horn under the following settings: 20 pulses per well at 10 seconds per pulse, and 60% power with 10 seconds between each pulse (Sonics Ultra-Cell). The lysates were centrifuged at 5,500×g for 15 minutes (4° C.) and the supernatants collected (soluble fraction).

SDS-CGE Analysis

Protein samples were analyzed by microchip SDS capillary gel electrophoresis using a LabChip GXII instrument (PerkinElmer) with a HT Protein Express chip and corresponding reagents (part numbers 760528 and CLS760675, respectively, PerkinElmer). Samples were prepared following the manufacturer's protocol (Protein User Guide Document No. 450589, Rev. 3). Briefly, in a 96-well polypropylene conical well PCR plate, 4 μL of sample were mixed with 14 μL of sample buffer, with 70 mM DTT reducing agent, heated at 95° C. for 5 min and diluted by the addition of 70 μL DI water. Null-strain lysates were run in parallel with test samples. LabChip GX v. 4.0.1425.0 was used to analyze data and generate gel-like images.

SDS-PAGE Analysis

SDS-PAGE analysis was used to determine the identity and purity of the asparaginase. Test samples were diluted with PBS and loading buffer plus 25 mM DTT, prior to heating at 70° C. for 10 minutes. Samples were loaded at 2 or 4 μg/well onto 12% Bis-Tris gels. The samples were resolved under a constant voltage of 200V with 1×MOPS running buffer until the dye front migrates down the length of the gel (approximately 1 hour). After electrophoresis, gels with 1 or 2 μg/well were stained with Oriole fluorescent gel stain (Bio-Rad) for an hour, and gels with 4 μg/well load were stained with GelCode Blue (ThermoFisher) overnight. After staining, the fluorescent-stained gel was transferred into water and then imaged using GelDoc EZ system (Bio-Rad). The blue stained gel was transferred into water for destain approximately 1.5 to 2 hours and then was imaged using the GelDoc EZ.

Western Blot

Western blot was used to determine the identity of the asparaginase. Test samples were diluted with PBS and loading buffer with reducing agent, DTT, prior to heating at 70° C. for 10 minutes. The samples were then loaded at 1 μg/well and resolved on a 12% Bis-Tris gel, same as the SDS-PAGE running conditions. Following electrophoresis, proteins were transferred to a nitrocellulose membrane at 25V, 125 mA for 90 minutes. Blocker Casein (Thermo) was used to block overnight at 2-8° C., followed by three washes with PBST (Sigma). The membrane was then incubated one hour at room temperature at 50 rpm with a rabbit anti-crisantaspase polyclonal antibody diluted 1:5000 in nine parts PBST and one-part Blocker Casein. Following three PBST washes, a goat anti-rabbit IgG coupled to Horseradish Peroxidase (HRP) was diluted 1:5000 in the 9:1 PBST: casein solution and incubated at room temperature at 50 rpm for one hour. Following three more washes, the antigen-antibody complex was revealed by addition of DAB substrate (Thermofisher). After the bands were clearly visible, the reaction was stopped by transferring the membrane in water, and the membrane was imaged using GelDoc EZ imaging system (Bio-Rad).

SE-HPLC

SE-HPLC for samples was carried out on an Agilent Technologies 1100 HPLC system equipped with a DAD UV detector. The mobile phase was 50 mM sodium phosphate, 200 mM NaCl pH 7.0. Dilution of stock drug product in 1×PBS to 1 mg/mL allowed 50 μg of each sample to be loaded onto a Phenomenex BioSep SEC s4000 (7.8 mm ID×300 mm, 5 μm) HPLC analytical column with a Phenomenex SEC-s4000 HPLC guard cartridge. UV absorbance was monitored at 215 nm with a flow rate of 1.0 mL/min. The column and sample temperature was not controlled with a total run time of 18 min. OpenLab software was used to calculate area % purity. Peak integration was performed with Standard tangent skim mode and zero values for all skim integration events. Baseline correction was set to No Penetration with a peak to valley ratio of 500. Initial integration events include a slope sensitivity of 1, peak width of 0.25, an area reject of 1, a height reject of 10, and shoulder integration set to DROP. Integration was inhibited from 0 to 7 minutes and from 11.15 minutes to the end of the run. The baseline was also set to Baseline Hold at 9 minutes.

Intact Mass Analysis of Target Protein

Soluble lysate samples were filtered/desalted into PBS prior to intact mass analysis by liquid chromatography coupled to mass spectrometry (LC-MS). Samples that had been purified by one or two column steps were run neat.

Samples were subjected to LC-MS analysis using an interconnected autosampler, column heater, UV detector, and HPLC (Waters Acquity) coupled to a Q-Tof micro mass spectrometer (Waters Xevo) with an electrospray interface. A CN column (Zorbax 5 μm, 300SB-CN, 2.1×150 mm, Agilent) fitted with a guard column (Zorbax 5 μm, 300SB-CN, 4.6×12.5 mm, Agilent) was used for separation at 50° C. The HPLC buffers used were buffer A (0.1% formic acid) and buffer B (100% acetonitrile 0.1% formic acid). A generic gradient was used. After loading at 5% B and 95% buffer A, the protein sample was subjected to the following reversed phase gradient at 0.2 mL/min: the column was subjected to a gradient from 5-60% B for 45 minutes, followed by a 2-minute gradient from 60% to 95% B, followed by 95% B for 3 minutes, and ending with 5% B for 5 minutes (60-minute total method time).

UV absorbance was collected from 180-500 nm, prior to MS. The MS source was used in positive. MS scans were carried out using a range of 600-2600 m/z at 2 scans per second. MS and UV data were analyzed using MassLynx software (Waters). UV chromatograms of MS total ion current (TIC) chromatograms were generated. The MS spectra of the target peaks were summed. These spectra were deconvoluted using MaxEnt 1 (Waters) scanning for a molecular weight range of 30,000-40,000 at a resolution of 1 Da per channel.

Example 3: Crisantaspase Tier 1 Expression Plasmid Screening in 96 Well Format

Figure 3:
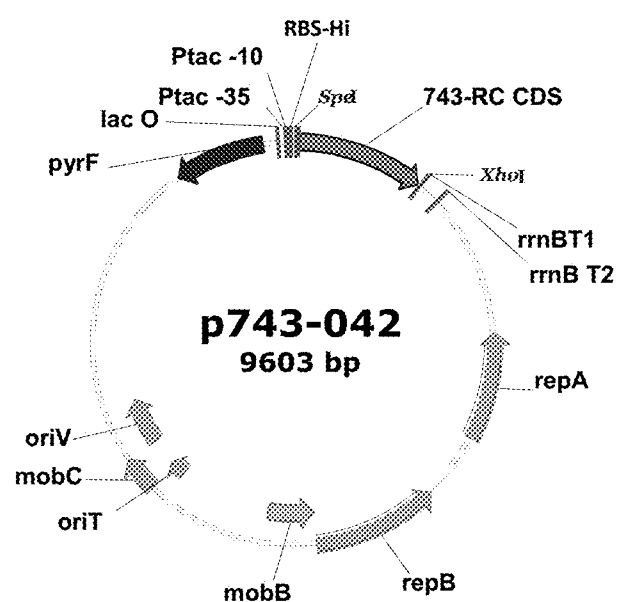
FIG. 3. Expression Plasmid Map. The map shows an example of a plasmid for expressing crisantaspase in *P. fluorescens*.

For the expression plasmid screening, an optimized crisantaspase protein coding sequence was designed and synthesized for expression in *P. fluorescens* as described in Example 2 (FIG. 2). Plasmids were constructed carrying the optimized crisantaspase gene fused to 37 different *P. fluorescens* secretion leaders and two ribosome binding-site (RBS) affinities (Table 5). An additional plasmid was constructed to express crisantaspase protein without a periplasmic leader in order to localize crisantaspase protein within the cell cytoplasm. A representative plasmid map (p743-042) is shown in FIG. 3. Expression of the target was driven from the Ptac promoter, and translation initiated from a high activity ribosome binding site (RBS). The resulting 40 plasmids were transformed into two *P. fluorescens* host strains, DC454 (WT) and DC441 (PD), to produce 80 expression strains for the Tier 1 (expression strategy) screening. The ranking of the expression strategies was based on SDS-CGE estimated titers of crisantaspase monomer.

The resulting cultures from the 80 transformations (40 expression strategies×2 host strains) were grown in 96-well plates as described in Example 2. Sonicate fraction samples from whole broth culture harvested 24 hours after induction were analyzed by SDS-CGE. Expression of induced protein consistent with the expected molecular weight for crisantaspase monomer (35 kDa), which also co-migrated with *E. coli* L-Asp (Sigma Product), was quantified. SDS-CGE quantitation of reduced samples was completed by comparing the induced bands to an *E. coli* L-Asp standard curve. The 20 highest yielding samples from both the DC454 and DC441 host strains were ranked (Table 8) based on estimated soluble crisantaspase monomer titers. FIG. 1 shows SDS-CGE gel-like figures generated from the analysis of the 96-well culture soluble sonicate samples. Table 8 shows 24 hours post-induction (I24) titers as estimated by SDS-CGE analysis of reduced soluble sonicates (single rep) and quantified by Labchip® internal ladder for plasmids expressed in the DC454 (table on left) and DC441 (table on right) host strains. Also shown is the secretion leader fusion produced from each p743 expression plasmid.

TABLE 8

Top 20 Expression Strains from Tier 1 Screening

| Strain ID (DC454 Host) | Plasmid | Secretion Leader | I24 Soluble (ug/mL) | Strain ID (DC441 Host) | Plasmid | Secretion Leader | I24 Soluble (ug/mL) |
|---|---|---|---|---|---|---|---|
| STR55337 | p743-001 | None | 1482 | STR55429 | p743-013 | FlgI** | 1523 |
| STR55349 | p743-013 | FlgI** | 1314 | STR55417 | p743-001 | None | 1369 |
| STR55369 | p743-033 | Leader O | 969 | STR55424 | p743-008 | Lao | 1329 |
| STR55374 | p743-038 | 8484** | 966 | STR55442 | p743-026 | PorE | 1136 |
| STR55356 | p743-020 | Leader C** | 852 | STR55434 | p743-018 | DsbC** | 946 |
| STR55354 | p743-018 | DsbC** | 832 | STR55436 | p743-020 | Leader C** | 727 |
| STR55345 | p743-009 | Ibp-S31A** | 810 | STR55454 | p743-038 | 8484** | 639 |
| STR55370 | p743-034 | 5193** | 674 | STR55425 | p743-009 | Ibp-S31A** | 600 |
| STR55347 | p743-011 | Tpr | 657 | STR55450 | p743-034 | 5193** | 532 |
| STR55348 | p743-012 | Ttg2C | 567 | STR55432 | p743-016 | Pbp | 525 |
| STR55371 | p743-035 | Leader P | 439 | STR55427 | p743-011 | Tpr | 492 |
| STR55351 | p743-015 | CupB2 | 433 | STR55449 | p743-033 | Leader O | 477 |
| STR55346 | p743-010 | TolB | 431 | STR55428 | p743-012 | Ttg2C | 384 |
| STR55360 | p743-024 | Leader G | 279 | STR55426 | p743-010 | TolB | 363 |
| STR55359 | p743-023 | Leader F | 273 | STR55435 | p743-019 | Leader B | 342 |
| STR55340 | p743-004 | DsbA | 270 | STR55431 | p743-015 | CupB2 | 248 |
| STR55355 | p743-019 | Leader B | 249 | STR55433 | p743-017 | PbpA20V | 225 |
| STR55353 | p743-017 | PbpA20V | 239 | STR55451 | p743-035 | Leader P | 223 |
| STR55373 | p743-037 | Leader R | 223 | STR55420 | p743-004 | DsbA | 222 |
| STR55350 | p743-014 | CupC2 | 220 | STR55452 | p743-036 | Leader Q | 190 |

(**Six secretion leaders observed in the top 10 highest yielding plasmids from both host strains.)

The six plasmids and incorporated secretion leaders (p743-013 (FlgI leader), p743-038 (8484), p743-020 (LolA), p743-018 (DsbC), p743-009 (Ibp-S31A) and p743-034 (5193)) observed in the top 10 highest yielding expression strains derived from both the DC454 and DC441 host strains are marked with  in Table 8. Additionally, the p743-001 expression plasmid, designed for cytoplasmic expression of crisantaspase protein, ranked in the top two highest soluble yields for both hosts. From both host strains combined, the top ten highest soluble titers ranged from 525 to 1,523 μg/mL. Insoluble yield was low for all the expressions observed with the highest insoluble yield achieving 230 μg/mL using the p743-013 plasmid. Observation of the SDS-CGE banding patterns (FIG. 1**) showed that the most complete secretion leader processing (removal upon export to the periplasm) occurred using the p743-013, p743-033 (Leader O), p743-038, p743-009 and p743-018 expression plasmids while the p743-016 and p743-017 plasmids were observed to produce a prominent lower molecular weight truncation product. The 10 expression plasmids shown in Table 6, were chosen for the subsequent host strain screening at 96-well HTP scale based on SDS-CGE estimated high soluble titer. The ten selected expression strategies were then combined with 24 unique host strains which could further influence crisantaspase protein titer and quality.

Example 4: Crisantaspase Tier 2 Host Strain Screening in 96 Well Format

The 10 selected crisantaspase expression strategies, or plasmids, identified in the Tier 1 expression strategy screening were each transformed into 24 *P. fluorescens* host strains (Table 7), including 11 protease deletion (PD) strains, 8 protease deletion plus folding modulator overexpressor (PD/FMO) strains, 4 FMO strains and one wild type strain to produce 240 expression strains. Folding modulators, when present, were encoded on a second plasmid and expression was driven by a *P. fluorescens*-native mannitol inducible promoter. The collection of 24 host strains was selected to reduce proteolytic degradation and/or promote protein solubility. The DC454 (WT) and DC441 (PD) strains used as the two host strains in the expression strategy screening were also included in the 24 host strain screen.

The 24 host strains carrying each of the 10 selected crisantaspase expression plasmids (240 expression strains in total) were grown in duplicate in 96-well format (HTP) as described in Example 2. Samples harvested 24 hours after induction were analyzed by SDS-CGE to detect and quantify soluble and insoluble crisantaspase protein expression. Screening of reduced soluble and insoluble fractions by SDS-CGE was carried out on a single replicate from all 240 strains. SDS-CGE detected induced bands co-migrating with the *E. coli* L-Asp standard (Sigma) and relative titers were interpolated from the *E. coli* L-Asp standard curve. Table 9 lists the 15 samples showing the highest estimated crisantaspase whole cell (soluble plus insoluble) monomer titers which ranged from 1,453 to 2,362 μg/mL.

Results from the SDS-CGE screening of a single HTP growth replicate are shown in Table 9. Each row identifies the crisantaspase expression strain ID, host strain used, host strain phenotype (PD=protease deletion; FMO=folding modulator overexpressor) and expression plasmid used. Reported titers are based on comparison to an *E. coli* L-Asp (Sigma) standard curve and are sorted based on Whole Cell (soluble plus insoluble) crisantaspase protein estimated titers.

TABLE 9

Top 15 Expression Strains from Tier 2 Screening

| | | | | SDS-CGE of Reduced HTP Sonicates | | |
|---|---|---|---|---|---|---|
| Strain ID | Host Strain | Phenotype | Plasmid | Soluble I24 (ug/mL) | Insoluble I24 (ug/mL) | Whole Cell I24 (ug/mL) |
| STR55876 | DC1100 | PD/FMO | p743-038 | 1903 | 459 | 2362 |
| STR55880 | DC1101 | PD/FMO | p743-017 | 1746 | 383 | 2130 |
| STR55871 | DC1100 | PD/FMO | p743-013 | 1723 | 367 | 2090 |
| STR55978 | PF1433 | WT | p743-042 | 1723 | 361 | 2084 |
| STR55901 | PF1332 | PD | p743-013 | 1432 | 588 | 2020 |
| STR55891 | PF1285 | PD | p743-013 | 1504 | 451 | 1955 |

TABLE 9-continued

| Top 15 Expression Strains from Tier 2 Screening | | | | | | |
|---|---|---|---|---|---|---|
| | | | | SDS-CGE of Reduced HTP Sonicates | | |
| Strain ID | Host Strain | Phenotype | Plasmid | Soluble I24 (ug/mL) | Insoluble I24 (ug/mL) | Whole Cell I24 (ug/mL) |
| STR55896 | PF1285 | PD | p743-038 | 1092 | 680 | 1772 |
| STR55906 | PF1332 | PD | p743-038 | 1290 | 464 | 1754 |
| STR55881 | DC1101 | PD/FMO | p743-013 | 1391 | 355 | 1746 |
| STR55872 | DC1100 | PD/FMO | p743-018 | 1233 | 380 | 1613 |
| STR55895 | PF1285 | PD | p743-034 | 934 | 595 | 1529 |
| STR55905 | PF1332 | PD | p743-034 | 824 | 677 | 1501 |
| STR55869 | DC1100 | PD/FMO | p743-009 | 1480 | 0 | 1480 |
| STR55736 | DC496 | PD | p743-038 | 1071 | 391 | 1461 |
| STR55892 | PF1285 | PD | p743-018 | 749 | 704 | 1453 |

Strain STR55978 harbors the cytoplasmic crisantaspase expression plasmid p743-042 in the wild-type *P. fluorescens* host strain background containing chromosomal deletions of native L-asparaginase type 1 and type 2 (PF1433 host strain). Strains STR55901, STR55891, STR55896 and STR55906 were constructed from either the PF1285 (PD) or PF1332 (PD) host strains harboring either the p743-013 or p743-038 expression plasmids. Based on the high soluble and total crisantaspase titers observed, these four strains were rebuilt as native L-asparaginase deficient versions. The STR55978 crisantaspase expression strain, which expresses a wild type crisantaspase in plasmid p743-042 in L-asparaginase deficient host strain PF1433, was selected for screening induction conditions at the 2 L fermentation scale.

Example 5: Crisantaspase Shake Flask Expression

Shake flask expression (200 mL) was performed after transforming selected expression plasmids, p743-042, p743-033 and p743-038, into asparaginase deficient host strain PF1433 to produce expression strains STR55978, STR55979 and STR55980, respectively. The shake flask expression work was completed in parallel to the construction of asparaginase deficient crisantaspase expression host strains (see Example 4) in order to evaluate whether deleting the endogenous asparaginase genes from the *P. fluorescens* chromosome produced observable growth penalties. Furthermore, lysate generated from shake flask samples were used for initial activity analysis and confirmation of intact mass by LC-MS analysis. Table 10 shows results from SDS-CGE analysis of reduced soluble and insoluble sonicates produced from the shake flask expression analysis.

TABLE 10

| Shake Flask Expression Results | | | | | |
|---|---|---|---|---|---|
| Strain | Plasmid | Avg Soluble Reduced (μg/ml) | % CV | Avg Insoluble Reduced (μg/ml) | % CV |
| STR55978 | p743-042 | 1464 | 7 | 181 | 30 |
| STR55979 | p743-033 | 743 | 13 | 195 | 42 |
| STR55980 | p743-038 | 908 | 2 | 180 | 48 |

Figure 4:
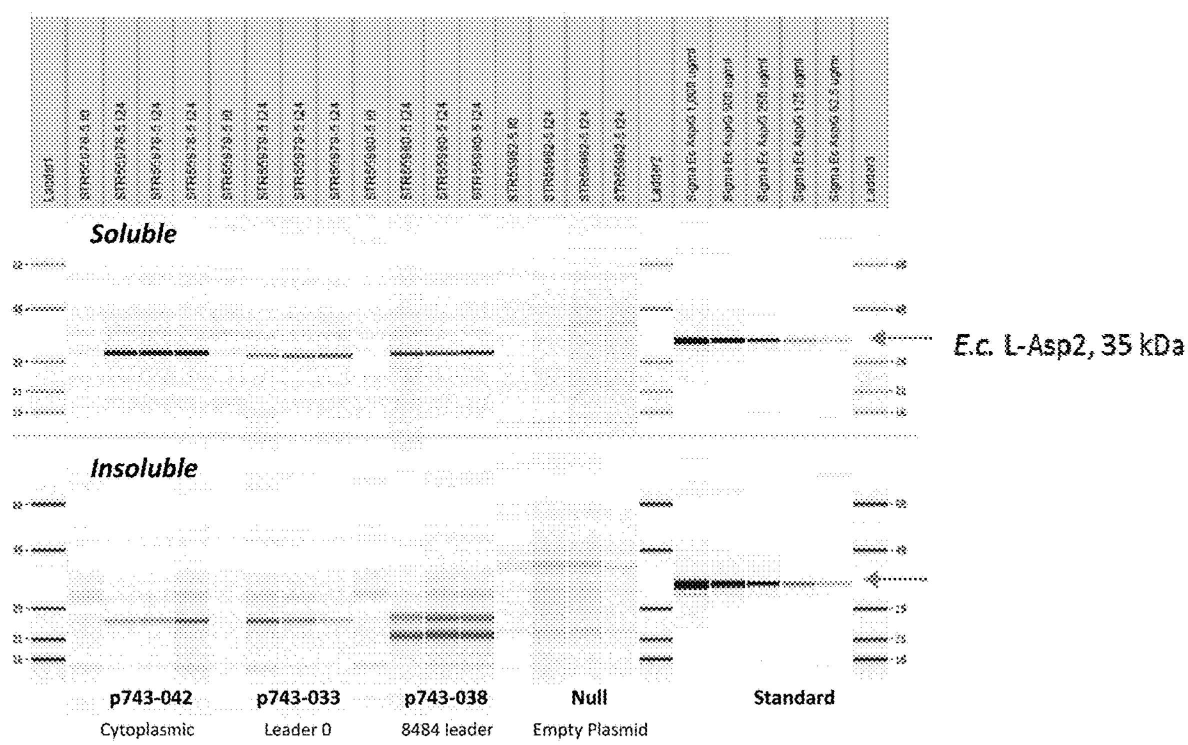
FIG. 4. SDS-CGE Gel-like Images—Shake Flask Expression Analysis. Expression under different growth conditions as measured by soluble, reduced capillary gel electrophoresis (SDS-CGE) is shown. From left to right are lanes showing the expression patterns observed in the following samples: Ladder 1 (molecular weight markers 68, 48, 29, 21, and 16 KD); STR55987 at I0 (cytoplasmic expression with no leader); STR55987 at I24 (cytoplasmic expression with no leader); STR55987 at I24 (cytoplasmic expression with no leader); STR55987 at I24 (cytoplasmic expression with no leader); STR55979 at I0 (Leader O); STR55979 at I24 (Leader O); STR55979 at I24 (Leader O); STR55979 at I24 (Leader O); STR55980 at I0 (8484 Leader); STR55980 at I24 (8484 Leader); STR55980 at I24 (8484 Leader); STR55980 at I24 (8484 Leader); STR55982 at I0 (Null plasmid); STR55982 at I24 (Null plasmid); STR55982 at I24 (Null plasmid); STR55982 at I24 (Null plasmid); Ladder 2 (same markers as in Ladder 1); Sigma *E. coli* AspG 1,000 ug/ml (standard *E. coli* Asp2); Sigma *E. coli* AspG 500 ug/ml; Sigma *E. coli* AspG 250 ug/ml; Sigma *E. coli* AspG 125 ug/ml; Sigma *E. coli* AspG 62.5 ug/ml; and Ladder 3 (same markers as in Ladder 1), where JO samples are taken at the time of induction and I24 samples are taken 24 hours post induction. The arrows at the right indicate migration of *E. coli* L-Asp2 (35 KD)

Table 10 shows the average estimated titers as determined by SDS-CGE analysis of soluble and insoluble sonicate fractions (ten different repetitions) of the three crisantaspase expression strains constructed using the PF1433 host strain (native asparaginase deficient, wild-type strain) analyzed at 200 mL working volume shake flask scale. SDS-CGE titers were estimated based on comparison to an *E. coli* L-Asp (Sigma) standard curve. The SDS-CGE gel-like images taken from both the soluble and insoluble sonicate analysis of each strain are shown in FIG. 4.

Included in the analysis were shake flask growth from two null strains: STR55982 and DC432. The DC432 strain harbors plasmid pDOW1169, which does not contain the crisantaspase coding region, in a wild-type *P. fluorescens* host strain. STR55982 harbors plasmid pDOW1169 in host strain PF1433 which contains chromosomal deletions of both the native asparaginase coding sequences. All three of the crisantaspase expression strains produced predominantly soluble crisantaspase protein expression with strain STR55978 achieving the highest soluble titers of up to 14 g/L. Furthermore, no growth penalty was observed as all three crisantaspase expression strains achieved a similar cell density (OD600=23.0, 27.0 and 27.8) at 24 hrs. post induction when compared to the STR55982 and DC432 null strains, which gave an $OD_{600}$ of 21.7 and 23.7, respectively, at 24 hours post induction.

Soluble sonicate samples generated from each of the five shake flask expression strains were analyzed for asparaginase activity using a commercial kit purchased from Sigma (Asparaginase Activity Assay Kit) according to the manufacturer's instructions. This kit measures activity using a coupled enzyme reaction which produces a colorimetric end product proportional to the aspartate generated. *E. coli* asparaginase type II obtained from Sigma was spiked into STR55982 null lysate as a positive control (last row Table 11).

The activity results are shown in Table 11.

TABLE 11

| Asparaginase Activity Assay of Shake Flask Culture Sonicate Samples | | | | | | |
|---|---|---|---|---|---|---|
| Sample Description | Plasmid ID | Sample ID | Asparaginase Titer (mg/ml)* | Sample Dilution Factor | Aspartate Generated (nmol) | Δ A570 (TF − T0) 20 min |
| Cytoplasmically expressed Crisantaspase | p743-042 | STR55978 | 0.29 | 25,000 | 0.89 | 0.04 |
| Leader O-Crisantaspase | p743-033 | STR55979 | 0.15 | 25,000 | 0.86 | 0.04 |
| 8484 leader-Crisantaspase | p743-038 | STR55980 | 0.18 | 25,000 | 0.88 | 0.04 |

TABLE 11-continued

Asparaginase Activity Assay of Shake Flask Culture Sonicate Samples

| Sample Description | Plasmid ID | Sample ID | Asparaginase Titer (mg/ml)* | Sample Dilution Factor | Aspartate Generated (nmol) | Δ A570 (TF − T0) 20 min |
|---|---|---|---|---|---|---|
| L-Asp − null | empty plasmid | STR55982 | 0.00 | 25,000 | 0.00 | 0.00 |
| L-asp + null | empty plasmid | DC432 | 0.00 | 25,000 | 0.00 | 0.00 |
| Null spike to 250 μg/ml** | N/A | L-Asp2 Sigma | 0.25 | 25,000 | 0.53 | 0.03 |

*Determined by SDS-CGE

**Sigma-A3809 *E. coli* AspG2 spiked into STR55982 (AspG deficient Null) lysate

While both of the null samples showed no measurable activity at the 1:25,000 dilution factor, soluble sonicate samples from strains STR55978, STR55979 and STR55980 diluted 1:25,000 showed activity comparable to similarly diluted STR55982 null strain sample spiked with 250 μg/mL *E. coli* L-asparaginase from Sigma. These activity results using a commercially available kit indicate that crisantaspase protein expressed in *P. fluorescens* can readily form active, tetrameric asparaginase enzyme within the generated sonicates.

Figure 7:
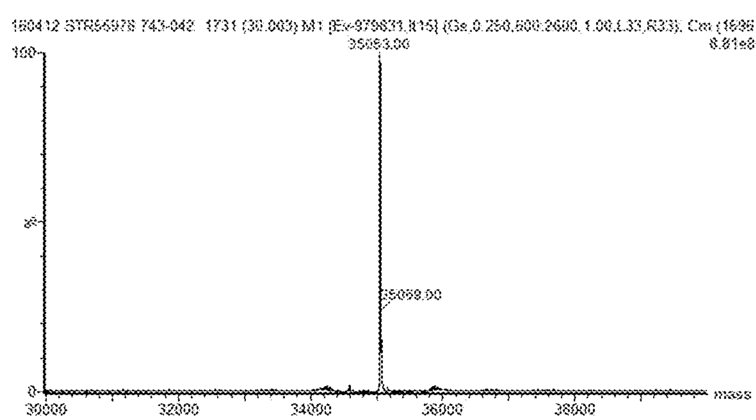
FIG. 7. Mass Spectrometry Data—Shake Flask Expression Analysis. Intact mass of expressed recombinant asparaginase is shown.

Table 12 shows the LC-MS intact mass results from the analysis of crisantaspase protein from soluble sonicates produced by strains STR55978, STR55979 and STR55980 in shake flasks. The observed molecular weight (35,053 Da) of the crisantaspase protein from each strain is consistent with the theoretical molecular weight (35054.2 Da) indicating that all three strains are generating the expected amino acid sequence and complete processing, or removal, of secretion leader if present. Sigma *E. coli* L-Asp was analyzed as a control. FIG. 7 shows a mass spectrometry readout for STR55978.

TABLE 12

LC-MS Analysis of Shake Flask Culture Sonicate Samples

| Sample Name | Theor. MW (Da) - signal | Observed MW (Da) | Obs. - Theor. MW (Da) |
|---|---|---|---|
| crisantaspase STR55978 | 35054.2 | 35053 | −1.2 |
| crisantaspase STR55979 | | 35053 | −1.2 |
| crisantaspase STR55980 | | 35053 | −1.2 |
| Sigma L-Asp A3809 | 34591.96 | 34591 | −0.96 |

Example 6: 2 L Fermentation Evaluations

Figure 5:
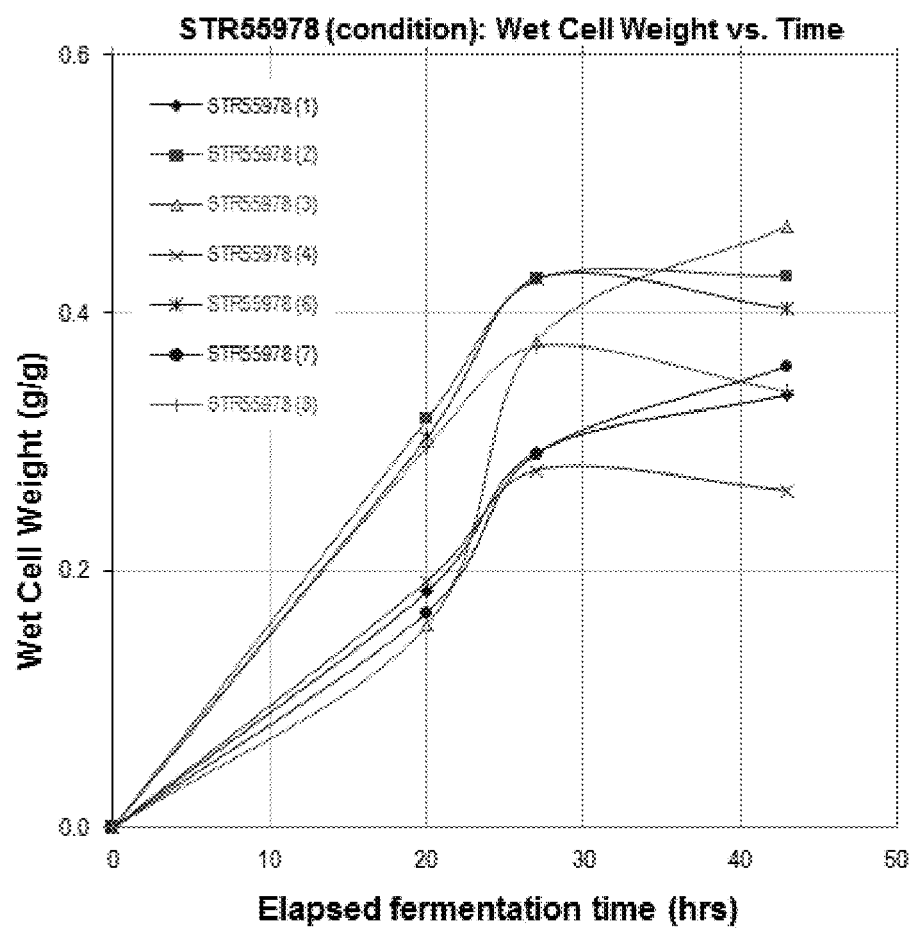
FIG. 5. Growth of STR55978—2 Liter Fermentations. Growth as measured by wet cell weight under different growth conditions (conditions 1-8) is shown as a function of fermentation time.
Figure 6:
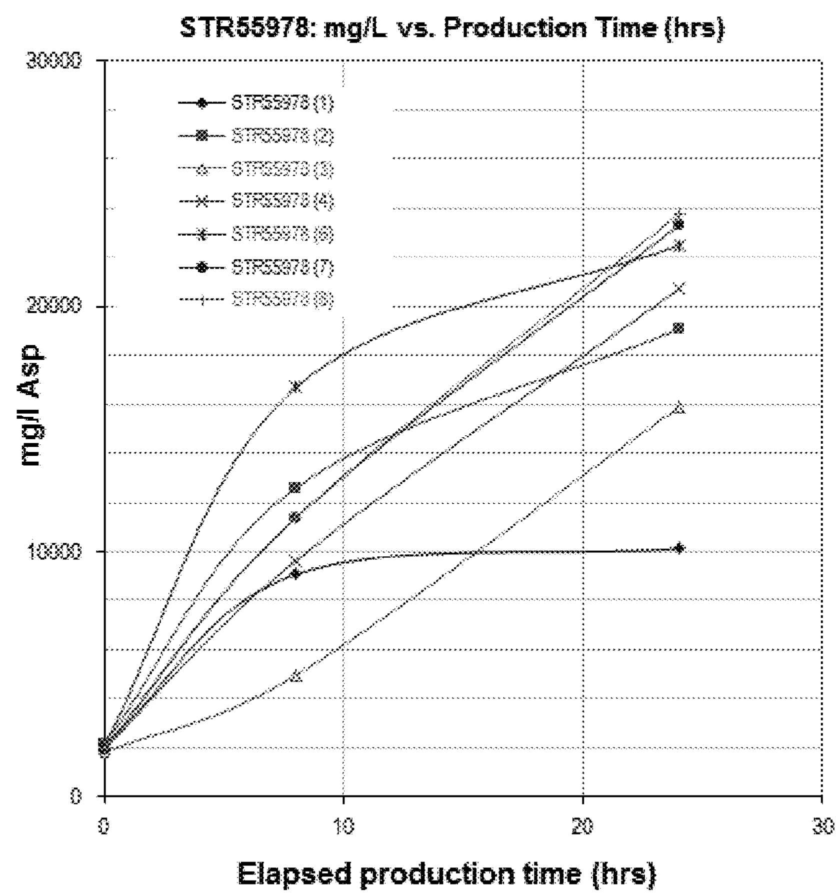
FIG. 6. STR55978 Protein Production—2 Liter Fermentations. Recombinant asparaginase titer as measured by reduced, soluble SDS-CGE, is shown.

Cytoplasmic expression strain STR55978, an endogenous asparaginase deficient strain, was evaluated under eight different fermentation induction conditions in a design-of-experiments (DOE) format. The conditions varied included WCW (g/g), IPTG concentration, pH and temperature at induction. Induction setpoints targeted in this fractional factorial DOE included cell density of 0.2-0.4 g/g wet cell weight, 0.08-0.2 mM IPTG, pH post-induction of 6.5-7.2, and post-induction culture temperature of 25-32° C. Growth as measured by wet cell weight for each condition is shown in FIG. 5. Titers of soluble crisantaspase ranged from 10-24 g/L or 20-40% total cell protein (Table 13). Recombinant crisantaspase expression as measured by reduced, soluble SDS-CGE, is shown in FIG. 6.

TABLE 13

Summary of Crisantaspase Protein Expression for STR55978 2 Liter Fermentations

| Expt Unit | Strain (Condition) | 8-hour induction titer (mg/L) | 24-hour induction titer (mg/L) | A575 at 24 hours post induction | Total Cell Protein at 24-hours post Induction (mg/L) | 24-hour induction Titer (% TCP) |
|---|---|---|---|---|---|---|
| 1 | STR55978 (1) | 9068 | 10116 | 176 | 48400 | 20.9 |
| 2 | STR55978 (2) | 12594 | 19072 | 230 | 63250 | 30.2 |
| 3 | STR55978 (3) | 4952 | 15895 | 234 | 64350 | 24.7 |
| 4 | STR55978 (4) | 9610 | 20703 | 272 | 74800 | 27.7 |
| 6 | STR55978 (6) | 16691 | 22488 | 220 | 60500 | 37.2 |
| 7 | STR55978 (7) | 11365 | 23301 | 230 | 63250 | 36.8 |
| 8 | STR55978 (8) | 11371 | 23756 | 222 | 61050 | 38.9 |

TABLE 14

| Table of Sequences Listed | | |
|---|---|---|
| Sequence | | SEQ ID NO: |
| *Erwinia* Crisantaspase amino acid | ADKLPNIVILATGGTIAGSAATGTQTTGYKAGALGVDTLINAVPEVKKLANVKGE<br>QFSNMASENMTGDVVLKLSQRVNELLARDDVDGVVITHGTDTVEESAYFLHLTVK<br>SDKPVVFVAAMRPATAISADGPMNLLEAVRVAGDKQSRGRGVMVVLNDRIGSARY<br>ITKTNASTLDTFKANEEGYLGVIIGNRIYYQNRIDKLHTTRSVFDVRGLTSLPKV<br>DILYGYQDDPEYLYDAAIQHGVKGIVYAGMGAGSVSVRGIAGMRKAMEKGVVVIR<br>STRTGNGIVPPDEELPGLVSDSLNPAHARILLMLALTRTSDPKVIQEYFHTY | 1 |
| A nucleic acid sequence optimized for *P. fluorescens*, encoding the *Erwinia* Crisantaspase of SEQ ID NO: 1 | GCAGACAAACTCCCTAACATCGTAATCCTCGCAACTGGTGGTACCATCGCAGGCA<br>GCGCCGCCACCGGCACGCAGACCACTGGCTACAAGGCCGGCGCGCTGGGCGTAGA<br>CACGCTGATCAACGCCGTCCCGGAAGTGAAGAAACTGGCCAACGTCAAGGGTGAG<br>CAATTCTCCAACATGGCCAGCGAGAACATGACTGGCGATGTGGTACTGAAGCTCT<br>CGCAGCGCGTGAACGAACTGCTCGCCCGCGACGACGTGGACGGCGTGGTGATCAC<br>CCACGGCACTGATACCGTCGAAGAGTCGGCGTACTTTCTCCACCTGACCGTGAAG<br>TCCGATAAGCCCGTGGTGTTTGTCGCCGCGATGCGCCCGGCGACCGCCATCAGCG<br>CCGACGGGCCGATGAATCTGTTGGAAGCCGTGCGCGTGGCGGGTGACAAGCAAAG<br>CCGCGGTCGGGGCGTAATGGTCGTCCTGAACGATCGGATCGGTAGCGCGCGGTAC<br>ATCACCAAGACGAACGCCTCCACGCTGGACACCTTCAAGGCGAACGAAGAGGGGT<br>ACCTGGGGGTGATCATTGGCAATCGTATCTATTACCAGAACCGCATCGACAAGCT<br>GCACACCACCCGCTCGGTGTTCGACGTGCGCGGTCTGACTAGCCTGCCCAAGGTC<br>GACATCCTGTACGGCTACCAAGACGACCCGGAGTACCTCTACGACGCGGCGATCC<br>AGCATGGCGTGAAGGGCATCGTCTACGCCGGTATGGGTGCCGGCTCGGTGTCGGT<br>CCGCGGCATCGCGGGTATGCGCAAGGCCATGGAGAAAGGCGTGGTCGTGATTCGC<br>TCGACCCGGACTGGCAATGGCATCGTACCGCCCGATGAAGAACTCCCGGGGCTCG<br>TGAGCGATAGCCTCAACCCCGCGCACGCCCGGATCCTGCTGATGCTGGCGCTCAC<br>GCGGACCAGCGACCCCAAGGTCATTCAAGAGTACTTCCACACCTAC | 2 |
| DsbA secretion leader amino acid sequence (*P. fluorescens*) | MRNLILSAALVTASLFGMTAQA | 3 |
| DsbA secretion leader nucleic acid sequence (*P. fluorescens*) | ATGCGTAATCTGATCCTCAGCGCCGCTCTCGTCACTGCCAGCCTCTTCGGCATGA<br>CCGCACAAGCT | 4 |
| Azurin secretion leader amino acid sequence (*P. fluorescens*) | MFAKLVAVSLLTLASGQLLA | 5 |
| Azurin secretion leader nucleic acid sequence (*P. fluorescens*) | ATGTTTGCCAAACTCGTTGCTGTTTCCCTGCTGACTCTGGCGAGCGGCCAGTTGC<br>TTGCT | 6 |
| LAO secretion leader amino acid sequence (*P. fluorescens*) | MQNYKKFLLAAAVSMAFSATAMA | 7 |
| LAO secretion leader nucleic acid sequence (*P. fluorescens*) | ATGCAGAACTATAAAAAATTCCTTCTGGCCGCGGCCGTCTCGATGGCGTTCAGCG<br>CCACGGCCATGGCA | 8 |
| Ibp-S31A secretion leader amino acid sequence (*P. fluorescens*) | MIRDNRLKTSLLRGLTLTLLSLTLLSPAAHA | 9 |
| Ibp-S31A secretion leader nucleic acid sequence (*P. fluorescens*) | ATGATCCGTGACAACCGACTCAAGACATCCCTTCTGCGCGGCCTGACCCTCACCC<br>TACTCAGCCTGACCCTGCTCTCGCCCGCGGCCCATGCC | 10 |
| TolB secretion leader amino acid sequence (*P. fluorescens*) | MRNLLRGMLVVICCMAGIAAA | 11 |
| TolB secretion leader nucleic acid sequence (*P. fluorescens*) | ATGAGAAACCTTCTTCGAGGAATGCTTGTCGTTATTTGCTGTATGGCAGGGATAG<br>CGGCGGCC | 12 |
| Tpr secretion leader amino acid sequence (*P. fluorescens*) | MNRSSALLLAFVFLSGCQAMA | 13 |

TABLE 14-continued

| Table of Sequences Listed | | |
|---|---|---|
| Sequence | | SEQ ID NO: |
| Tpr secretion leader nucleic acid sequence (*P. fluorescens*) | ATGAATAGATCTTCCGCGTTGCTCCTCGCTTTTGTCTTCCTCAGCGGCTGCCAGG CCATGGCC | 14 |
| Ttg2C secretion leader amino acid sequence (*P. fluorescens*) | MQNRTVEIGVGLFLLAGILALLLLALRVSGLSA | 15 |
| Ttg2C secretion leader nucleic acid sequence (*P. fluorescens*) | ATGCAAAACCGCACTGTGGAAATCGGTGTCGGCCTTTTCTTGCTGGCTGGCATCC TGGCTTTACTGTTGTTGGCCCTGCGAGTCAGCGGCCTTTCGGCC | 16 |
| FlgI secretion leader amino acid sequence (*P. fluorescens*) | MKFKQLMAMALLLALSAVAQA | 17 |
| FlgI secretion leader nucleic acid sequence (*P. fluorescens*) | ATGAAGTTCAAACAGCTGATGGCGATGGCGCTTTTGTTGGCCTTGAGCGCTGTGG CCCAGGCC | 18 |
| CupC2 secretion leader amino acid sequence (*P. fluorescens*) | MPPRSIAACLGLLGLLMATQAAA | 19 |
| CupC2 secretion leader nucleic acid sequence (*P. fluorescens*) | ATGCCGCCTCGTTCTATCGCCGCATGTCTGGGGCTGCTGGGCTTGCTCATGGCTA CCCAGGCCGCCGCC | 20 |
| CupB2 secretion leader amino acid sequence (*P. fluorescens*) | MLFRTLLASLTFAVIAGLPSTAHA | 21 |
| CupB2 secretion leader nucleic acid sequence (*P. fluorescens*) | ATGCTTTTTCGCACATTACTGGCGAGCCTTACCTTTGCTGTCATCGCCGGCTTAC CGTCCACGGCCCACGCG | 22 |
| Pbp secretion leader amino acid sequence (*P. fluorescens*) | MKLKRLMAAMTFVAAGVATANAVA | 23 |
| Pbp secretion leader nucleic acid sequence (*P. fluorescens*) | ATGAAACTGAAACGTTTGATGGCGGCAATGACTTTTGTCGCTGCTGGCGTTGCGA CCGCCAACGCGGTGGCC | 24 |
| PbpA20V secretion leader amino acid sequence (*P. fluorescens*) | MKLKRLMAAMTFVAAGVATVNAVA | 25 |
| PbpA20V secretion leader nucleic acid sequence (*P. fluorescens*) | ATGAAACTGAAACGTTTGATGGCGGCAATGACTTTTGTCGCTGCTGGCGTTGCGA CCGTCAACGCGGTGGCC | 26 |
| DsbC secretion leader amino acid sequence (*P. fluorescens*) | MRLTQIIAAAAIALVSTFALA | 27 |
| DsbC secretion leader nucleic acid sequence (*P. fluorescens*) | ATGCGCTTGACCCAGATTATTGCCGCCGCAGCCATTGCGTTGGTTTCCACCTTTG CGCTCGCC | 28 |
| PorE secretion leader amino acid sequence (*P. fluorescens*) | MKKSTLAVAVTLGAIAQQAGA | 29 |
| PorE secretion leader nucleic acid sequence (*P. fluorescens*) | ATGAAGAAGTCCACCTTGGCTGTGGCTGTAACGTTGGGCGCAATCGCCCAGCAAG CAGGCGCT | 30 |

TABLE 14-continued

| Table of Sequences Listed | | |
|---|---|---|
| Sequence | | SEQ ID NO: |
| 5193 secretion leader amino acid sequence (*P. fluorescens*) | MQSLPFSALRLLGVLAVMVCVLLTTPARA | 31 |
| 5193 secretion leader nucleic acid sequence (*P. fluorescens*) | ATGCAAAGCCTGCCGTTCTCTGCGTTACGCCTGCTCGGTGTGCTGGCAGTCATGG TCTGCGTGCTGTTGACGACGCCAGCCCGTGCC | 32 |
| 8484 secretion leader amino acid sequence (*P. fluorescens*) | MRQLFFCLMLMVSLTAHA | 33 |
| 8484 secretion leader nucleic acid sequence (*P. fluorescens*) | ATGCGACAACTATTTTTCTGTTTGATGCTGATGGTGTCGCTCACGGCGCACGCC | 34 |
| FlgI-Crisantaspase amino acid | MKFKQLMAMALLLALSAVAQAADKLPNIVILATGGTIAGSAATGTQTTGYKAGAL GVDTLINAVPEVKKLANVKGEQFSNMASENMTGDVVLKLSQRVNELLARDDVDGV VITHGTDTVEESAYFLHLTVKSDKPVVFVAAMRPATAISADGPMNLLEAVRVAGD KQSRGRGVMVVLNDRIGSARYITKTNASTLDTFKANEEGYLGVIIGNRIYYQNRI DKLHTTRSVFDVRGLTSLPKVDILYGYQDDPEYLYDAAIQHGVKGIVYAGMGAGS VSVRGIAGMRKAMEKGVVVIRSTRTGNGIVPPDEELPGLVSDSLNPAHARILLML ALTRTSDPKVIQEYFHTY | 35 |
| 8484-Crisantaspase amino acid | MRQLFFCLMLMVSLTAHAADKLPNIVILATGGTIAGSAATGTQTTGYKAGALGVD TLINAVPEVKKLANVKGEQFSNMASENMTGDVVLKLSQRVNELLARDDVDGVVIT HGTDTVEESAYFLHLTVKSDKPVVFVAAMRPATAISADGPMNLLEAVRVAGDKQS RGRGVMVVLNDRIGSARYITKTNASTLDTFKANEEGYLGVIIGNRIYYQNRIDKL HTTRSVFDVRGLTSLPKVDILYGYQDDPEYLYDAAIQHGVKGIVYAGMGAGSVSV RGIAGMRKAMEKGVVVIRSTRTGNGIVPPDEELPGLVSDSLNPAHARILLMLALT RTSDPKVIQEYFHTY | 36 |
| DsbC-Crisantaspase amino acid | MRLTQIIAAAAIALVSTFALAADKLPNIVILATGGTIAGSAATGTQTTGYKAGAL GVDTLINAVPEVKKLANVKGEQFSNMASENMTGDVVLKLSQRVNELLARDDVDGV VITHGTDTVEESAYFLHLTVKSDKPVVFVAAMRPATAISADGPMNLLEAVRVAGD KQSRGRGVMVVLNDRIGSARYITKTNASTLDTFKANEEGYLGVIIGNRIYYQNRI DKLHTTRSVFDVRGLTSLPKVDILYGYQDDPEYLYDAAIQHGVKGIVYAGMGAGS VSVRGIAGMRKAMEKGVVVIRSTRTGNGIVPPDEELPGLVSDSLNPAHARILLML ALTRTSDPKVIQEYFHTY | 37 |
| Ibp-S31A-Crisantaspase amino acid | MIRDNRLKTSLLRGLTLTLLSLTLLSPAAHAADKLPNIVILATGGTIAGSAATGT QTTGYKAGALGVDTLINAVPEVKKLANVKGEQFSNMASENMTGDVVLKLSQRVNE LLARDDVDGVVITHGTDTVEESAYFLHLTVKSDKPVVFVAAMRPATAISADGPMN LLEAVRVAGDKQSRGRGVMVVLNDRIGSARYITKTNASTLDTFKANEEGYLGVII GNRIYYQNRIDKLHTTRSVFDVRGLTSLPKVDILYGYQDDPEYLYDAAIQHGVKG IVYAGMGAGSVSVRGIAGMRKAMEKGVVVIRSTRTGNGIVPPDEELPGLVSDSLN PAHARILLMLALTRTSDPKVIQEYFHTY | 38 |
| 5193-Crisantaspase amino acid | MQSLPFSALRLLGVLAVMVCVLLTTPARAADKLPNIVILATGGTIAGSAATGTQT TGYKAGALGVDTLINAVPEVKKLANVKGEQFSNMASENMTGDVVLKLSQRVNELL ARDDVDGVVITHGTDTVEESAYFLHLTVKSDKPVVFVAAMRPATAISADGPMNLL EAVRVAGDKQSRGRGVMVVLNDRIGSARYITKTNASTLDTFKANEEGYLGVIIGN RIYYQNRIDKLHTTRSVFDVRGLTSLPKVDILYGYQDDPEYLYDAAIQHGVKGIV YAGMGAGSVSVRGIAGMRKAMEKGVVVIRSTRTGNGIVPPDEELPGLVSDSLNPA HARILLMLALTRTSDPKVIQEYFHTY | 39 |
| Tpr-Crisantaspase amino acid | MNRSSALLLAFVFLSGCQAMAADKLPNIVILATGGTIAGSAATGTQTTGYKAGAL GVDTLINAVPEVKKLANVKGEQFSNMASENMTGDVVLKLSQRVNELLARDDVDGV VITHGTDTVEESAYFLHLTVKSDKPVVFVAAMRPATAISADGPMNLLEAVRVAGD KQSRGRGVMVVLNDRIGSARYITKTNASTLDTFKANEEGYLGVIIGNRIYYQNRI DKLHTTRSVFDVRGLTSLPKVDILYGYQDDPEYLYDAAIQHGVKGIVYAGMGAGS VSVRGIAGMRKAMEKGVVVIRSTRTGNGIVPPDEELPGLVSDSLNPAHARILLML ALTRTSDPKVIQEYFHTY | 40 |
| Ttg2C-Crisantaspase amino acid | MQNRTVEIGVGLFLLAGILALLLLALRVSGLSAADKLPNIVILATGGTIAGSAAT GTQTTGYKAGALGVDTLINAVPEVKKLANVKGEQFSNMASENMTGDVVLKLSQRV NELLARDDVDGVVITHGTDTVEESAYFLHLTVKSDKPVVFVAAMRPATAISADGP MNLLEAVRVAGDKQSRGRGVMVVLNDRIGSARYITKTNASTLDTFKANEEGYLGV IIGNRIYYQNRIDKLHTTRSVFDVRGLTSLPKVDILYGYQDDPEYLYDAAIQHGV KGIVYAGMGAGSVSVRGIAGMRKAMEKGVVVIRSTRTGNGIVPPDEELPGLVSDS LNPAHARILLMLALTRTSDPKVIQEYFHTY | 41 |

TABLE 14-continued

| Table of Sequences Listed | | |
|---|---|---|
| Sequence | | SEQ ID NO: |
| CupB2-Crisantaspase amino acid | MLFRTLLASLTFAVIAGLPSTAHAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 42 |
| TolB-Crisantaspase amino acid | MRNLLRGMLVVICCMAGIAAAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 43 |
| DsbA-Crisantaspase amino acid | MRNLILSAALVTASLFGMTAQAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 44 |
| PbpA20V-Crisantaspase amino acid | MKLKRLMAAMTFVAAGVATVNAVAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 45 |
| CupC2-Crisantaspase amino acid | MPPRSIAACLGLLGLLMATQAAAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 46 |
| Lao-Crisantaspase amino acid | MQNYKKFLLAAAVSMAFSATAMAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 47 |
| PorE-Crisantaspase amino acid | MKKSTLAVAVTLGAIAQQAGAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 48 |
| Pbp-Crisantaspase amino acid | MKLKRLMAAMTFVAAGVATANAVAADKLPNIVILATGGTIAGSAATGTQTTGYKAGALGVDTLINAVPEVKKLANVKGEQFSNMASENMTGDVVLKLSQRVNELLARDDVDGVVITHGTDTVEESAYFLHLTVKSDKPVVFVAAMRPATAISADGPMNLLEAVRVAGDKQSRGRGVMVVLNDRIGSARYITKTNASTLDTFKANEEGYLGVIIGNRIYYQNRIDKLHTTRSVFDVRGLTSLPKVDILYGYQDDPEYLYDAAIQHGVKGIVYAGMGAGSVSVRGIAGMRKAMEKGVVVIRSTRTGNGIVPPDEELPGLVSDSLNPAHARILLMLALTRTSDPKVIQEYFHTY | 49 |
| Consensus RBS (high binding strength) | AGGAGG | 50 |
| RBS2 | GGAGCG | 51 |
| RBS34 | GGAGCG | 52 |
| RBS41 | AGGAGT | 53 |

TABLE 14-continued

| Table of Sequences Listed | | |
|---|---|---|
| Sequence | | SEQ ID NO: |
| RBS43 | GGAGTG | 54 |
| RBS48 | GAGTAA | 55 |
| RBS1 | AGAGAG | 56 |
| RBS35 | AAGGCA | 57 |
| RBS49 | CCGAAC | 58 |
| Skp (OmpH RXF4702.1) | MRKLTQLVLLATVLVTTPAFAEMKIAVLNYQMALLESDAAKRYAVDAEKKFGPQL TKLKTLESSAKGIQDRLVAGGDKMQQGERERLELEFKQKARDYQFQSKELNEAKA VADREMLKQLKPKLDSAVEEVIKKGAFDLVFERGAVIDVKPQYDITRQVIERMNQ LK | 59 |
| Skp (ompH) RXF04702.1 Nucleic acid sequence (*P. fluorescens*) | GTGCGTAAGTTGACTCAATTGGTCTTGCTGGCCACTGTGCTGGTCACCACCCCGG CCTTCGCCGAAATGAAAATCGCCGTTCTGAACTATCAGATGGCCCTGCTGGAATC CGATGCGGCCAAGCGATACGCCGTGGATGCCGAGAAGAAGTTCGGTCCGCAACTG ACCAAGCTCAAGACACTGGAAAGCAGCGCCAAAGGCATCCAGGACCGCCTGGTAG CCGGTGGCGACAAGATGCAGCAAGGCGAGCGCGAGCGTCTGGAGCTTGAATTCAA GCAAAAGGCCCGTGACTACCAGTTCCAATCCAAGGAGCTGAACGAAGCCAAGGCT GTGGCCGACCGCGAAATGCTCAAGCAGCTCAAGCCTAAATTGGACAGCGCTGTGG AAGAAGTCATCAAGAAGGGTGCCTTTGACCTGGTGTTCGAGCGTGGCGCCGTGAT CGACGTCAAGCCTCAATACGACATCACCCGCCAGGTGATCGAGCGCATGAACCAG CTGAAGTGA | 60 |
| AspG1 (*P. fluorescens*; RXF08567; peg5048) | MQSANNVMVLYTGGTIGMQASANGLAPASGFEVRMREQFAGADLPAWRFQEMSPL IDSANMNPAYWQRLRSAVVEAVDAGCDAVLILHGTDTLAYSAAAMSFQLLGLPAP VVFTGSMLPAGVPDSDAWENVSGALTALGEGLKPGVHLYFHGALMAPTRCAKIRS FGRNPFAALQRNGGVALADKLPAALAYRNDKAPANVGVLPLVPGIAAAQLDALID SGIQALVLECFGSGTGPSDNPAFLASLKRAQDQEVVVVAITQCHEGGVELDVYEA GSRLRSVGVLSGGGMTREAAFGKLNALIGAGLDSAEIRRLVELDLCGELS | 61 |
| AspG2 (*P. fluorescens*; RXF05674; peg3886) | MKSALKNVIPGALALLLLFPVAAQAKEVESKTKLSNVVILATGGTIAGAGASAAN SATYQAAKVGIEQLIAGVPELSQIANVRGEQVMQIASESINNENLLQLGRRVAEL ADNKDVDGIVITHGTDTLEETAYFLNLVEKTDKPIVVVGSMRPGTAMSADGMLNL YNAVAVAGSKEARGKGVLVTMNDEIQSGRDVSKMINIKTEAFKSPWGPMGMVVEG KSYWFRLPAKRHTMDSEFDIKTIKSLPDVEIAYGYGNVSDTAYKALAQAGAKAII HAGTGNGSVSSKVVPALVELRKQGVQIIRSSHVNAGGMVLRNAEQPDDKYDWVAA LDLNPQKARILAMVALTKTQDSKELQRIFWEY | 62 |
| A nucleic acid sequence optimized for *P. fluorescens*, encoding the *Erwinia* Crisantaspase of SEQ ID NO: 1, including restriction sites as shown in FIG. 2 | ATATGCTCTTCAGCCGCAGACAAACTCCCTAACATCGTAATCCTCGCAACTGGTG GTACCATCGCAGGCAGCGCCGCCACCGGCACGCAGACCACTGGCTACAAGGCCGG CGCGCTGGGCGTAGACACGCTGATCAACGCCGTCCCGGAAGTGAAGAAACTGGCC AACGTCAAGGGTGAGCAATTCTCCAACATGGCCAGCGAGAACATGACTGGCGATG TGGTACTGAAGCTCTCGCAGCGCGTGAACGAACTGCTCGCCCGCGACGACGTGGA CGGCGTGGTGATCACCCACGGCACTGATACCGTCGAAGAGTCGGCGTACTTTCTC CACCTGACCGTGAAGTCCGATAAGCCCGTGGTGTTTGTCGCCGCGATGCGCCCGG CGACCGCCATCAGCGCCGACGGGCCGATGAATCTGTTGGAAGCCGTGCGCGTGGC GGGTGACAAGCAAAGCCGCGGTCGGGGCGTAATGGTCGTCCTGAACGATCGGATC GGTAGCGCGCGGTACATCACCAAGACGAACGCCTCCACGCTGGACACCTTCAAGG CGAACGAAGAGGGGTACCTGGGGGTGATCATTGGCAATCGTATCTATTACCAGAA CCGCATCGACAAGCTGCACACCACCCGCTCGGTGTTCGACGTGCGCGGTCTGACT AGCCTGCCCAAGGTCGACATCCTGTACGGCTACCAAGACGACCCGGAGTACCTCT ACGACGCGGCGATCCAGCATGGCGTGAAGGGCATCGTCTACGCCGGTATGGGTGC CGGCTCGGTGTCGGTCCGCGGCATCGCGGGTATGCGCAAGGCCATGGAGAAAGGC GTGGTCGTGATTCGCTCGACCCGGACTGGCAATGGCATCGTACCGCCCGATGAAG AACTCCCGGGGCTCGTGAGCGATAGCCTCAACCCCGCGCACGCCCGGATCCTGCT GATGCTGGCGCTCACGCGGACCAGCGACCCCAAGGTCATTCAAGAGTACTTCCAC ACCTACTGATAATAGTTCAGAAGAGCATAT | 63 |

While preferred embodiments of the present disclosure have been shown and described herein, such embodiments are provided by way of example only. Numerous variations, changes, and substitutions will now occur to those skilled in the art without departing from the disclosure. It should be understood that various alternatives to the embodiments of the disclosure described herein may be employed in practicing the methods herein. It is intended that the following claims define the scope of the invention and that methods and structures within the scope of these claims and their equivalents be covered thereby.

What is claimed is:

1. A method for producing a recombinant type II asparaginase, the method comprising culturing a Pseudomonadales host cell in a culture medium and expressing the recombinant type II asparaginase in the cytoplasm of the Pseudomonadales host cell from an expression construct comprising a nucleic acid encoding the recombinant type II asparaginase, wherein the nucleic acid encoding the recombinant type II asparaginase comprises a sequence at least 85% homologous to SEQ ID NO: 1, and wherein the recombinant asparaginase is produced in the cytoplasm at a yield of about 20% to about 40% total cell protein (TCP) in soluble form.

2. The method of claim 1, wherein the recombinant type II asparaginase is produced in the cytoplasm at a yield of about 10 g/L to about 25 g/L.

3. The method of claim 1, further comprising measuring the activity of an amount of the soluble recombinant type II asparaginase produced, using an activity assay.

4. The method of claim 1, wherein the recombinant type II asparaginase is an *Erwinia chrysanthemi* L-asparaginase type II (crisantaspase).

5. The method of claim 1, wherein the nucleic acid encoding the recombinant type II asparaginase comprises a sequence at least 85% homologous to SEQ ID NO: 2.

6. The method of claim 1, wherein the recombinant type II asparaginase has an amino acid sequence as set forth in SEQ ID NO: 1.

7. The method of claim 1, wherein the Pseudomonadales host cell is a *Pseudomonas fluorescens* cell.

8. The method of claim 1, wherein the host cell is deficient in the expression of one or more native asparaginases.

9. The method of claim 8, wherein the one or more deficiently expressed native asparaginase is selected from: a type I asparaginase; a type II asparaginase; and a combination thereof.

10. The method of claim 1, wherein the host cell: is deficient in the expression of one or more proteases; overexpresses one or more folding modulators; or both.

11. A method for producing a recombinant type II asparaginase, the method comprising: culturing a Pseudomonadales host cell in a culture medium and expressing the recombinant type II asparaginase in the periplasm of the host cell from an expression construct comprising a nucleic acid encoding the recombinant type II asparaginase, wherein the nucleic acid encoding the recombinant type II asparaginase comprises a sequence at least 85% homologous to SEQ ID NO: 1, and wherein the recombinant type II asparaginase is produced in the periplasm at a yield of about 20% to about 40% total cell protein (TCP) in soluble form.

12. The method of claim 11, wherein the recombinant type II asparaginase is produced in the periplasm at a yield of about 5 g/L to about 30 g/L.

13. The method of claim 11, wherein the method further comprises measuring the activity of an amount of the recombinant type II asparaginase produced, using an activity assay.

14. The method of claim 11, wherein the recombinant type II asparaginase is an *Erwinia chrysanthemi* L-asparaginase type II (crisantaspase).

15. The method of claim 11, wherein the nucleic acid encoding the recombinant type II asparaginase comprises a sequence at least 85% homologous to SEQ ID NO: 2.

16. The method of claim 11, wherein the recombinant type II asparaginase has an amino acid sequence as set forth in SEQ ID NO: 1.

17. The method of claim 11, wherein the Pseudomonadales host cell is a *Pseudomonas fluorescens* cell.

18. The method of claim 11, wherein the host cell is deficient in the expression of one or more asparaginases.

19. The method of claim 18, wherein the deficiently expressed asparaginase is selected from: a type I asparaginase, a type II asparaginase, or both.

20. The method of claim 11, wherein the expression construct comprises a secretion leader that directs transfer of the recombinant type II asparaginase produced to the periplasm of the host cell.

21. The method of claim 20, wherein the secretion leader is selected from the group consisting of FlgI, Ibps31A, PbpA20V, DsbC, 8484, and 5193.

22. The method of claim 3, further comprising comparing the measured activity of the recombinant type II asparaginase produced with a measured activity of the same amount of a control type II asparaginase using the same activity assay, wherein the measured activity of the recombinant type II asparaginase produced is comparable to the activity of the control type II asparaginase.

23. The method of claim 13, further comprising comparing the measured activity of the recombinant type II asparaginase produced with a measured activity of the same amount of a control type II asparaginase using the same activity assay, wherein the measured activity of the recombinant type II asparaginase produced is comparable to the activity of the control type II asparaginase.

24. The method of claim 1, wherein the recombinant type II asparaginase is modified to increase half-life in patients.

25. The method of claim 1, wherein the host cell: is deficient in the expression of one or more proteases; overexpresses one or more folding modulators; or both.

26. The method of claim 25, wherein the host cell: is deficient in HslUV protease, is deficient in PrtB protease; is deficient in Prc protease; is deficient in DegP protease; is deficient in AprA protease; is deficient in Lon protease; is deficient in La protease; is deficient in DegP1; is deficient in DegP2; overexpresses DegP S219A; or a combination thereof.

27. The method of claim 11, wherein the recombinant type II asparaginase is modified to increase half-life in patients.

28. The method of claim 1, wherein the recombinant type II asparaginase produced is used in the treatment of patients with acute lymphoblastic leukemia.

29. The method of claim 11, wherein the recombinant type II asparaginase produced is used in the treatment of patients with acute lymphoblastic leukemia.

* * * * *

UNITED STATES PATENT AND TRADEMARK OFFICE

CERTIFICATE OF CORRECTION

PATENT NO. : 10,787,671 B2
APPLICATION NO. : 16/163382
DATED : September 29, 2020
INVENTOR(S) : Coleman et al.

It is certified that error appears in the above-identified patent and that said Letters Patent is hereby corrected as shown below:

In the Specification

Column 1,
Lines 62-66, delete "In some embodiments, the nucleic acid encoding the recombinant asparaginase comprises a sequence at least 85% homologous to SEQ ID NO: 1. In some embodiments, the recombinant asparaginase has an amino acid sequence at least 85% homologous to SEQ ID NO: 2" and insert -- In some embodiments, the nucleic acid encoding the recombinant asparaginase comprises a sequence at least 85% homologous to SEQ ID NO: 2. In some embodiments, the recombinant asparaginase has an amino acid sequence at least 85% homologous to SEQ ID NO: 1 --

Column 2,
Lines 45-49, delete "In some embodiments, the nucleic acid encoding the recombinant asparaginase comprises a sequence at least 85% homologous to SEQ ID NO: 1. In some embodiments, the recombinant asparaginase has an amino acid sequence at least 85% homologous to SEQ ID NO: 2" and insert -- In some embodiments, the nucleic acid encoding the recombinant asparaginase comprises a sequence at least 85% homologous to SEQ ID NO: 2. In some embodiments, the recombinant asparaginase has an amino acid sequence at least 85% homologous to SEQ ID NO: 1 --

In the Claims

Column 111, Claim 1
Lines 32-34, delete "wherein the nucleic acid encoding the recombinant type II asparaginase comprises a sequence at least 85% homologous to SEQ ID NO: 1" and insert -- wherein the recombinant type II asparaginase encoded by the nucleic acid comprises an amino acid sequence at least 85% homologous to SEQ ID NO: 1 --

Column 112, Claim 11
Lines 28-30, delete "wherein the nucleic acid encoding the recombinant type II asparaginase comprises a sequence at least 85% homologous to SEQ ID NO: 1" and insert -- wherein the Signed and Sealed this
Twenty-eighth Day of June, 2022

Katherine Kelly Vidal
*Director of the United States Patent and Trademark Office* recombinant type II asparaginase encoded by the nucleic acid comprises an amino acid sequence at least 85% homologous to SEQ ID NO: 1 --